United States Patent
Potts et al.

(10) Patent No.: US 7,276,530 B2
(45) Date of Patent: Oct. 2, 2007

(54) [3.2.0] HETEROCYCLIC COMPOUNDS AND METHODS OF USING THE SAME

(75) Inventors: Barbara Christine Potts, Escondido, CA (US); Venkat Macherla, San Diego, CA (US); Scott Sherman Mitchell, San Carlos, CA (US); Ram Rao Manam, San Diego, CA (US); Katherine Reed, San Diego, CA (US); Kin Sing Lam, San Diego, CA (US); Saskia Neuteboom, La Jolla, CA (US); Ta-Hsiang Chao, San Diego, CA (US); Benjamin Nicholson, San Diego, CA (US); Cheryl Billstrom, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 49 days.

(21) Appl. No.: 11/118,260

(22) Filed: Apr. 29, 2005

(65) Prior Publication Data
US 2005/0288352 A1 Dec. 29, 2005

Related U.S. Application Data

(60) Provisional application No. 60/659,385, filed on Mar. 4, 2005, provisional application No. 60/644,132, filed on Jan. 13, 2005, provisional application No. 60/627,462, filed on Nov. 12, 2004, provisional application No. 60/591,190, filed on Jul. 26, 2004, provisional application No. 60/580,838, filed on Jun. 18, 2004, provisional application No. 60/567,336, filed on Apr. 30, 2004.

(51) Int. Cl.
A61K 31/407 (2006.01)
C07D 491/044 (2006.01)

(52) U.S. Cl. ...................................... 514/421; 548/453

(58) Field of Classification Search ................ 548/453; 514/421
See application file for complete search history.

(56) References Cited

U.S. PATENT DOCUMENTS

| | | | |
|---|---|---|---|
| 5,445,829 A | 8/1995 | Paradissis et al. |
| 5,576,012 A | 11/1996 | Bauer et al. |
| 5,601,845 A | 2/1997 | Buxton et al. |
| 5,641,515 A | 6/1997 | Ramtoola |
| 5,653,987 A | 8/1997 | Modi et al. |
| 5,654,286 A | 8/1997 | Hostetler |
| 5,667,809 A | 9/1997 | Trevino et al. |
| 5,683,676 A | 11/1997 | Akehurst et al. |
| 5,688,529 A | 11/1997 | Lidgate et al. |
| 5,707,615 A | 1/1998 | Cardin et al. |
| 5,707,641 A | 1/1998 | Gertner et al. |
| 5,726,181 A | 3/1998 | Hausheer et al. |
| 5,733,888 A | 3/1998 | Carver et al. |
| 5,756,764 A | 5/1998 | Fenteany et al. |
| 5,874,443 A | 2/1999 | Kiely et al. |
| 5,886,210 A | 3/1999 | Rayle et al. |
| 5,922,683 A | 7/1999 | Or et al. |
| 6,133,308 A | 10/2000 | Soucy et al. |
| 6,147,223 A | 11/2000 | Fenteany et al. |
| 6,214,862 B1 | 4/2001 | Fenteany et al. |
| 6,294,560 B1 | 9/2001 | Soucy et al. |
| 6,335,358 B1 | 1/2002 | Fenteany et al. |
| 6,350,759 B1 | 2/2002 | Casara et al. |
| 6,458,825 B1 | 10/2002 | Fenteany et al. |
| 6,500,825 B2 | 12/2002 | Lan et al. |
| 6,506,787 B2 | 1/2003 | Fujishita et al. |
| 6,509,331 B1 | 1/2003 | Audia et al. |
| 6,566,553 B2 | 5/2003 | Soucy et al. |
| 6,645,999 B1 | 11/2003 | Schreiber et al. |
| 6,794,516 B2 | 9/2004 | Soucy et al. |
| 6,838,477 B2 | 1/2005 | Schreiber et al. |
| 6,849,743 B2 | 2/2005 | Soucy et al. |
| 2001/0002391 A1 | 5/2001 | Brand et al. |
| 2001/0051654 A1 | 12/2001 | Elliott et al. |
| 2003/0157695 A1 | 8/2003 | Fenical et al. |
| 2004/0138196 A1 | 7/2004 | Fenical et al. |
| 2004/0259856 A1 | 12/2004 | Fenical et al. |

(Continued)

FOREIGN PATENT DOCUMENTS

WO WO96/32105 10/1996

(Continued)

OTHER PUBLICATIONS

Sapi et al., Collection of Czechoslovak Chemical Communications 1999, 64(2), 190-202.*

(Continued)

*Primary Examiner*—Kamal A. Saeed
*Assistant Examiner*—Jason M. Nolan
(74) *Attorney, Agent, or Firm*—Knobbe Martens Olson & Bear LLP

(57) ABSTRACT

Compounds of Formulae I-VI and derivatives thereof having anti-cancer, anti-inflammatory, and anti-microbial properties and to compositions that include one or more of compounds and their derivatives or analogs having anti-cancer, anti-inflammatory and anti-microbial properties are disclosed. Pharmaceutical compositions comprising such compounds and methods of treating cancer, inflammatory conditions, and microbial infections with the disclosed compounds or the disclosed pharmaceutical compositions are also disclosed.

48 Claims, 17 Drawing Sheets

U.S. PATENT DOCUMENTS

| | | |
|---|---|---|
| 2005/0049294 A1 | 3/2005 | Palladino et al. |
| 2005/0203162 A1 | 9/2005 | Xiao et al. |
| 2005/0228186 A1 | 10/2005 | Corey |
| 2005/0239866 A1 | 10/2005 | Fenical et al. |
| 2006/0008852 A1 | 1/2006 | Fenical et al. |

FOREIGN PATENT DOCUMENTS

| | | |
|---|---|---|
| WO | WO99/09006 | 2/1999 |
| WO | WO99/15183 | 4/1999 |
| WO | WO 00/23614 | 4/2000 |
| WO | WO 02/47610 | 6/2002 |
| WO | WO 04/043374 A | 11/2003 |
| WO | WO 04/071382 | 8/2004 |
| WO | WO 2004071382 A2 * | 8/2004 |
| WO | WO 05/002572 | 1/2005 |
| WO | WO 05/003137 | 1/2005 |
| WO | 06/028525 | 3/2005 |
| WO | WO 2005099687 A2 * | 10/2005 |
| WO | 06/005551 | 1/2006 |
| WO | 06/060609 | 6/2006 |
| WO | WO 06/060809 | 6/2006 |

OTHER PUBLICATIONS

CAS Abstract attached.*
Adams, Julian. "Proteasome inhibitors as new anticancer drugs." *Curr. Opin. Oncol.* 14:628 (2002).
Adams, et al., "Proteasome Inhibitors: A Novel Class of Potent and Effective Antitumor Agents." *Cancer Res* 59:2615 (1999).
Adams, J., "The Development of novel targeted therapeutics for treatment of multiple myeloma research roundtable." *European Journal of Haematology* 70: 263-272. (2003).
Alessandri G, Raju K. & Bullino PM., "Mobilation of capillary endothelium in vitro induced by effectors of angiogenesis in vivo." *Cancer Res.* 43(4):1790-7. (1983).
Alm et al., "Effects of Topically Applied PGF2 and its Isopropylester on Normal and Glaucomatous Human Eyes." *Prog. Clin. Biol. Res.*, 312:447-58 (1989).
Beers, et al., *The Merck Research Laboratories*, Whitehouse Station N.J. XP002318189. 1157-1159.
Beers, et al., *The Merck Research Laboratories*, Whitehouse Station N.J. XP002318189. 1241-1252.
Bhalla, et al., "High-Dose Mitoxantrone Induces Programmed Cell Death or Apoptosis in Human Myeloid Leukemia Cells." *Blood* 82:10 pp. 3133-3140 (1993). Eds.
Bicknell, R. J., Claire E. Lewis & Napoleone FE, "Tumour Angiogenesis," Oxford University Press, New York (Sep. 1, 1997).
Blum, et al., "A New Anticancer Drug with Significant Clinical Activity." *Ann Intern Med* 80:249 (1974).
Bodart, et al., "Anthrax, MEK and Cancer." *Cell cycle* 1:10 (2002).
Bradley, et al., "Identification of the Cellular Receptor for Anthrax Toxin." *Nature* 414:225 (2001).
Bull, A.T. et al., "Search and Discovery Strategies for Biotechnology: the Paradigm Shift." *Microbiol Mol. Biol. Rev.* 64:573 (2000).
Carey, Francis. *Organic Chemistry*, 2d ed., Mcgraw Hill, Inc. New York. pp. 328-331. (1992).
Claverol, et al., "Mapping and Structural Dissection of Human 20 S Proteasome Using Proteomic Approaches." *Mol Cell Proteomics* 1:567 (2002).
Crane, et al., "A Novel Enantioselective Synthetic Route to Omuralide Analogues with the Potential for Species Selectivity in Proteasome Inhibition." *Organic Letters*, 1395-1397. (2001).
Cragg, et al. "Chemical Diversity: a function of biodiversity." *Trends Pharmacol Sci* 23:404 (2002).
Cusak, et al., "Enhanced Chemosensitivity to CPT-11 with Proteasome Inhibitor PS-341: Implications for Systemic Nuclear Factor-kB Inhibition." *Cancer Res* 61:3535 (2001).
Decker, et al., "Inhibition of Caspase-3-mediated Poly (ADP-ribose) Polymerase (PARP) Apoptotic Cleavage by Human PARP Autoantibodies and Effect on Cells Undergoing Apoptosis." *J Biol Chem.* 275:9043 (2000).
Dick, et al., "Mechanistic Studies on the Inactivation of the Proteasome by Lactacystin." *J Biol Chem.* 271:7273 (1996).
"DTP Human Tumor Cell Line Screen." *Screening Services.* DPI. Sep. 28, 2005 <http://dtp.nci.nih.gov/branches/btb/ivclsp.html>.
Duesberry, et al., "Proteolytic Inactivation of MAP-Kinase-Kinase by Anthrax Lethal Factor." *Science* 280:734 (1998).
Elliott, et al., "Proteasome inhibition: a new anti-inflammatory strategy." *J Mol Med*; 81:235-245. (2003).
Elliot, et al., "The Proteasome: A new target for novel drug therapies", *American Journal of Clinical Pathology.* 637-646. (2001).
Escuyer, et al., "Anthrax Protective Antigen Interacts with a Specific Receptor on the Surface of CHO-K1 Cells." *Infect Immun* 59:3381 (1991).
Faulkner, D.J. "Marine Natural Products." *Nat Prod Rep* 18:1-49 (2001).
Feling, et al. "Salinosporamide A: A Highly Cytotoxic Proteasome Inhibitor from a Novel Microbial Source, a Marine Bacterium of the New Genus Salinospora." *Angew. Chem. Int. Ed.* 42(3):355-357 (2003).
Fenical, et al. "Marine Microorganisms as a Developing Resource for Drug Discovery." *Pharmaceutical News*, 489-494 (2002).
Fenteany G. et al., "Inhibition of Proteasome Activities and Subunit-Specific Amino-Terminal Threonine modification by Lactacystin." *Science*, 268, 726-73 (1995).
Fingl, et al., The Pharmaceutical Basis of Therapeutics, 1975.
Folkman, J., "Tumor angiogenesis." *Adv Cancer Res.* 43:175-203. (1985).
Folkman, J., "Angiogenesis-dependent diseases." *Semin Oncol*, 28, 536-42. (2001).
Fukuchi, et al., "Direct Proteasome inhibition by clasto-lactacystin B-lactone permits the detection of ubiquitinated p21 in ML-1 Cells." *Biochem Biophys Acta* 1451:206 (1999).
Gale, et al., The Molecular Basis of Antibiotic Action $2^{nd}$ edition, John Wiley and Sons, London (1981).
Gantt, et al., "Proteasome inhibitors block development of Plasmodium spp." *Antimicrobial Agents and Chemotherapy.* 2731-2738. (1998).
Geier, et al., "A Giant Protease with Potential to Substitute for Some Functions of the Proteasome." *Science* 283:978 (1999).
Goldberg, et al. "Not just research tools—proteasome inhibitors offer therapeutic promise." *Natural Medicine.* 338-340 (2002) XP008038140.
Golub, et al. "Molecular Classification of Cancer; Class Discovery and Class Prediction by Gene Expression Monitoring." *Science.* 286:531-537 (1999).
Grant, et al., "Intracellular Mechanisms Involved in Basement Membrane Induced Blood Vessel Differentiation in Vitro," *In Vitro Cell Div. Biol.* 27A:327-336 (1991).
Grosios et al:, "Angiogenesis Inhibition by the Novel VEGF Receptor Tyrosine Kinase Inhibitor; PTK787/ZK222584, Causes Significant Anti-Arthritic Effects in Models Of Rheumatoid Arthritis," *Inflamm* Res, 53, 133-42.
Hanna, et al., "On the Role of Macrophages in Anthrax." *Proc Natl Sci USA* 90:10198 (1993).
Harker W.G., et al., "Multidrug resistance in mitoxantrone-selected HL-60 leukemia cells in the absence of P-glycoprotein overexpression," *Cancer Res.*, 15: 49(16) 4542-9 (1989).
Hideshima, T., et al., "NF-Kappa B as a therapeutic target in multiple myeloma," *J. Biol. Chem.*, 10; 277(19): 16639-47 (2002).
Higuchi, et al., "Pro-drugs as Novel Delivery Systems", vol. 14, *A.C.S. Symposium Series American Chemical Societym* Atlantic City, NJ., Sep. 10, 1974, (1975).
Hull et al., "Antiangiogenic Agents Are Effective Inhibitors of Endometriosis." *J Clin Endocrinol Metab*, 88, 2889-99. (2003).
International Search Report and Written Opinion. International Application No. PCT/US2004/019543; International Filing Date: Jun. 18, 2004.
Jensen et al., "Marine Microorganisms and Drug Discovery: Current Status and Future Potential." *Drugs from the Sea.* pp. 6-29. (2000).
Joshi, A. "Microparticulates for Ophthalmic Drug Delivery." *J Ocul Pharmacol* 10:29-45 (1994).

Kalns, et al., "TNF Receptor 1, IL-1 Receptor, and iNOS Genetic Knockout Micre Are Not Protected from Anthrax Infection." *Biochem Biophys Res Commun* 292:41-44 (2002).

Kalns, et al. "Delayed treatment with doxycycline has limited effect on anthrax infection in BLK57/B6 mice." *Biochem Biophys Res Commun* 297:506 (2002).

Kerr, et al., "Marine Natural Products as Therapeutic agents." *Exp Opin Ther Patents* 9:1207. (1999).

Kim, et al., "Sensitizing Anthrax Lethal Toxin-resistant Macrophages to Lethal Toxin-induced killing by Tumor Necrosis Factor." *J Biol Chem* 278:7413 (2003).

King, et al., "How Proteolysis Drives the Cell Cycle." *Science* 274:1652 (1996).

Kisselev, et al., "Proteasome inhibitors: from research tools to drug candidates." *Chem Biol* 8:739 (2001).

Kozlowski, et al., "Lactacystin Inhibits Cathepsin A Activity in Melanoma Cell Lines." *Tumour Biol* 22:211 (2001).

Lacy, et al., "Mapping the Anthrax Protective Antigen Binding Site on the Lethal and Edema Factors." *J Biol Chem* 277:3006 (2002).

Lam, et al., "Isolation of a Bromo Analog of Rebeccamycin From Saccharothrix Aerocolonigenes." *J Antibiot* (Tokyo), 44:934 (1991).

Lam, et al., "Production, Isolation and Structure Determination of Novel Fluoroindolocarbazoles from Saccharothrix aerocolonigenes ATCC 39243." *J Antibiot* (Tokyo) 54:1 (2001).

Lawley, TJ & Kubota, Y. "Induction of morphologic differentiation of endothelial cells in culture", *J Investigative Dermatology*. Aug: 93 (2 Suppl):59S-61S. (1989).

Lightcap, et al., "Proteasome Inhibition Measurements Clinical Application." *Clin Chem* 46:673 (2000).

Lin, et al. "Cytotoxic Effects of Anthrax Lethal Toxin on Macrophage-Like Cell Line J774A.1" *Curr Microbiol* 33:224 (1996).

Liu, et al., "Precursor Supply for Polyketide Biosynthesis: the role of Crotonyl-CoA Reductase." *Metab Eng* 3:40 (2001).

Liu et al., "Angiogenesis Inhibitors May Regulate Adiposity." *Nutr Rev*, 61, 384-7. (2003).

Mayer et al., "Efficacy of a Novel Hydrogel Formulation in Human volunteers." *Ophthalmologica*, 210(2):101-3 (1996).

Mayer, et al., "Marine Pharmacology in 1999: Antitumor and Cytotoxic Compounds." *Anticancer RES* 21:2489. (2001).

McMurry, John. *Organic Chemistry*, 5$^{th}$ ed., Brooks/Cole, Pacific Grove, CA. pp. 398 and 408. (2000).

Meng, et al., "Eponemycin exerts its antitumor effect through the inhibition of proteasome function," *Cancer Res.*,59(12): 2798-2801 (1999).

Meng, et al. "Epoxomicin, a potent and selective proteasome inhibitor, exhibits in vivo anti-inflammatory activity," *Proc. Natl. Acad. Sci.*, vol. 96, pp. 10403-10408, Aug. 1999.

Min, et al., "Urokinase Receptor Antagonists Inhibit Angiogenesis and Primary Tumor Growth in Syngeneic Mice." *Cancer Res.* 56:2428-2433 (1996).

Mogridge, et al., "Stiochiometry of Antrax Toxin Complexes." *Biochemistry* 41:1079 (2002).

Moore, B.S., "Biosynthesis of Marine Natural Products: Microorganisms and macroalgae." *Nat Prod Rep* 16:653. (1999).

Mordenti, et al. "Intracular Pharmacokinetics and Safety of a Humanized Monoclonal Antibody in Rabbits after Intravitreal Administration of a Solution or a PLGA Microsphere Formulation." *Toxicol. Sci.*, 52(1):101-6 (1999).

Mousa et al., "Angiogenesis Inhibitors: Current & Future Directions," *Curr Pharm Des*, 10, 1-9. (2004).

Murray, J. Clifford, Angiogenesis Protocols (Methods in Molecular Medicine), Humana Press Totowa, NJ. (Mar. 15, 2001).

Newton. "II fondo agli oceani potenti antibiotici e anticancro." www.newton.rcs.it/PrimoPiano/News/2003/02_Febbraio/03/Antobiotico.html. (Feb. 2, 2003) XP002304843.

Nicholson, D.W., "ICE/CED 3-Like Proteases as Therapeutic Targets for the Control of Inappropriate Apoptosis." *Nat Biotechnol* 14:297 (1996).

Nicosia et al.,. "Growth of Microvessels in Serum-Free Matrix Culture of Rat Aorta: A Quantitative Assay of Angiogenesis In Vitro," *Lab Invest*. Jul;63(1):115-22. (1990).

Nicolaus B.J. R. "Symbiotic Approach to Drug Design." *Decision Making in Drug Research*. 173-189 (1983) XP002197412.

Oikawa, et al., "Angiogenic Factor of a Rat Mammary Tumor Cell Line (RMT-1) (I). Secretion of Two Distinct Angiogenic Factors into Serum-Free Conditioned Medium by RMT-1 Cells," *Cancer Lett*. 59:57-66 (1991).

Okami, Y. "The Search for Bioactive Metabolites from marine Bacteria." *J. Mar Biotechnol* 1:59-65. (1993).

Omura, et al., "Lactacystin, A novel Microbial Metabolite, induces Neuritogenesis of Neuroblastoma Cells." *J Antibiot* (Tokyo) 44:113 (1991).

Ostrowska, et al., "Lactacystin, A Specific Inhibitor of the Proteasome, Inhibits Human Platelet Lysosomal Cathepsin A-like Enzyme." *Biochem Biophys Res Commun* 234:729 (1997).

Ostrowska, et al., "Separation of Cathepsin A-like enzyme and the proteasome: evidence that lactacystin/B-Lactone is not a specific inhibitor of the Proteasome." *Int J Biochem Cell Biol.* 32:747 (2000).

Pagano, et al., "Role of the Ubiquitin-Proteasome Pathway in Regulating Abundance of the Cyclin-Dependent Kinase Inhibitor p27." *Science*. 269:682 (1995).

Painter, R.B., "Inhibition of DNA Replicon Initiation by 4-Nitroquinoline 1-Oxide, Adriamycin, and Ethyleneimine." *Cancer Res* 38;4445 (1978).

Palayoor, et al., "Constitutive activation of ikB Kinase and NF-kB in prostate cancer cells is inhibited by ibuprofen." *Oncogene* 18:7389-94 (1999).

Plunkett et al., "Methods in Laboratory Investigation: An In Vivo Quantitative Angiogenesis Model Using Tumor Cells Entrapped in Alginate." *Lab Invest*. Apr;62(4):510-7. (1990).

Qureshi, et al., "The Proteasome as a Libopolysaccharide-Binding Protein in Macrophages: Differential Effects of Pretoasome Inhibition on Lipopolysaccharide-Induced Signaling Events." *J. Immunol*. 717(3):1515-25 (2003)

Reddy, et al. "A Simple Stereocontrolled Synthesis of Salinosporamide A." *Journal of the American Chemical Society*. 126(20), 6230-6231. (2004) XP008038141.

A.R. Gannaro ed. REMINGTON's Pharmaceutical Sciences, 17$^{th}$ Ed., Mack Publishing Co. Easton, PA, (1985).

A.R.Gennaro ed., REMINGTON's Pharmaceutical Sciences, 18$^{th}$ Ed., Mach Publishing Co., Easton, PA (1990).

Riva, S.,"Biocatalytic Modification of Natural Products." *Curr Opin Chem Biol* 5:106 (2001).

Roche, Edward B., ed. *Bioreversible Carriers in Drug Design*, Pergamon Press, Elmsford, NY(1987).

Rubanyi, Gabor M. ed., "Angiogenesis in Health and Disease: Basic Mechanisms and Clinical Applications," *J. Cell. Physiol*. 165:107-118 (1995).

Schnaper, et al., "Plasminogen Activators Augment Endothelial Cell Organization In Vitro by Two Distinct Pathways." *J. Cell. Physiol*. 165:107-118 (1995).

Shah, et al. "Early Clinical experience with the novel proteasome inhibitor PS-519." *J. Clin. Pharmacol*. 54. 269-276. (2002).

Grayson M. ed., Shadomy S., et al., "Chemotherapeutics, antimycotic and antirickettsial. In: Antibiotics, chemotherapeutics, and antibacterial Agents for Disease Control.". John Wiley and Sons, New York. (1982).

Shedden, et al., "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double Masked, Multicancer Study." *Clin. Ther.*, 23(3):440-50 (2001).

Shimada, K., et al., "Contributions of Mitogen-activated Protein Kinase and Nuclear Factor Kappa B to N-(4-hydroxyphenyl) retinamide-induced apoptosis in prostate cancer cells," *Mol. Carcinog*. 35(3): 127-37 (2002).

Stanford et al., "Bortezomib Treatment for Multiple Myeloma." *The Ann. Of Pahrma*. vol. 37. 1825-1830. (2003).

Streitwieser, Andrew and Clayton Heathcock, *Introduction to Organic Chemistry*, 2d ed., Macmillan Publishing Co. Inc., New York, NY, pp. 169-171. (1981).

Sunwoo, et al., Novel Proteasome Inhibitor PS-341 Inhibits Activation of Nuclear Factor-kB, Cell Survival, Tumor Growth, and Angiogenesis in Squamous Cell Carcinoma.: *Clin Cancer Res* 7:1419. (2001).

Takeuchi, et al., "Troglitazone Induces G1 Arrest by p27 Induction That Is Mediated by Inhibition of Proteasome in Human Gastric Cancer Cells." *Jpn J Cancer Res* 93:774 (2002).

Tang, et al., "Proteasome activity is required for anthrax lethal toxin to kill macrophages." *Infection and Immunity.* 67:3055-3060. (1999).

Vitale, et al., "Susceptibility of mitogen-activated protein kinase kinase family members to proteolysis by anthrax lethal factor." *Viochem J* 352 Pt :739 (2000).

Vitale, et al., "Anthrax Lethal factor cleaves the N-terminus of MAPKKS and induces tyrosine/threonine phosphorylation of MAPKS in cultured macrophages." *J Appl Microbiol* 87:288. (1999).

Zaks, A., "Industrial Biocatalysis," *Curr Opin Chem Biol* 5:130. (2001).

Zhang, et al., "Postischemic (6 Hour) Treatment with Recombinant Human Tissue Plaminogen Activator and Proteasome Inhibitor PS-519 Reduces Infarction in a Rat Model of Embolic Focal Cerebral Ischemia." *Stroke.* 2926-2931. (2001).

Bernan, V.S., et al., "Marine Microorganisms as a Source of New Natural Products" *Advances in Applied Microbiology* 1997, 43:57-90.

Blunt, J.W. et al. "Marine Natural Products" *Nat. Prod. Rep.*, 2003, 20:1-48.

Cheng, X.C. et al., "Luisols A and B, New Aromatic Tetraols Produced by an Estuarine Marine Bacterium of the Genus *Streptomyces* (Actinomycetales)" *J. Nat. Prod.* 1999, 62: 608-610.

Cheng, X.C. et al., "Arenaric Acid, a New Pentacyclic Polyether Produced by Marine Bacterium (Actinomycetales)" *J. Nat. Prod.* 1999, 62:605-607.

Colquhoun et al, "Rapid characterization of deep-sea actionmycetes for biotechnology screengin programmes" *Antonie Van Leeuwenoek Dordrecht*, NL, 2000, 77:359-367.

Colquhoun, et al., "Novel rhodocccl and other mycolate actinomycetes from the deep sea" *Antonie van Leeuwenhoek*, 1998, 74:27-40.

Colquhoun, et al., "Taxonomy and biotranformation activities of some deep-sea actinomycetes" *Extremophiles*, 1998 2:269-277.

Crueger et al, "Biotechnology: a textbook of industrial microbilogy" 2d Ed. Sinauer Assoc., Inc., Chapter 2, pp. 4-8, Jun. 1990.

Davidson, B.S. "New dimensions in natural products research: cultured marine microoganisms" *Current Opinion in Biotechnology* 1995, 6: 284-291.

Delong, et al. "Environmental Diversity of Bacteria and Archaea", *Syst. Biol.* 2001, 50(4):470-478.

Erba, E, et al., "Mode of action of thiocoraline, a natural marine compounds with anti-tumour activity" *British Journal of Cancer* 1999, 88(7)971-980.

Fenical, et al., Marine Microorganisms as a Biomedical Source: Are they unculturable or Uncultured? PowerPoint Presentation, Center for Marine Biotechnology and Biomedicine (Feb. 24, 2002).

Fenical, et al.; "Salinospora, a Major New Marine Actinomycete Taxon for Drug Discovery." Powerpoint Presentation, Center for Marine Biotechnology and Biomedicine (Jun. 24, 2001).

Fenical, W., "Chemical Studies of Marine Bacteria: Developing a New Resource" *Chem Review* 1993, 93:1673-1683.

Fenical, W. "New pharmaceuticals from marine organisms" *Marine Biotechnolgy* 1997, 15:339-341.

Fernandez-Chimeno, R.I., et al. "IB-96212, a Novel Cytotoxic Macrolide Produced by a Marine *Micromonospora*" *Journal of Antibiotics* 2000, 53(5) 474-478.

Fusetani, "Drugs from the Sea" Krageer, Basel, 2000, pp. 6-29.

Giovannoni, Steven, "Oceans of Bacteria" *Nature* Jul. 29, 2004, 430: 515-516.

Goodfellow, et al., "Actinomycetes in Marine Sediments" *Biological Biochemical and Biomedical Aspects of Adtinomycetes*, 1984, Academic Press, Inc. Orlando, pp. 453-472.

Goodfellow, et al., "Ecology of Actinomycestes" *Ann. Rev. Microbiol.* 1983, 37: 189-216.

Goodfellow et al., 1989, "Search and Discovery of Industrially Significant Actinomycetes" In Microbial products: New approaches, Society for General Microbiology Symposium No. 44 eds Baumberg, S. et al. pp. 343-383.

Harker W.G., et al, "Multidrug resistance in mitoxantrone-selected HL-60 leukemia cells in the absence of P-glycoprotein overexpression," *Cancer Res.*, 1989, 15: 49(16) 4542-9.

He, H. et al. "Lomaiviticians A and B, Potent Antitumor Antibiotics from *Micromonospora Iomaivitiensis*" *J. Am. Chem. Soc.* 2001, 123:5362-5363.

Helmke et al., "Rhodococcus marinonascens new species an actinomycete from the sea" *International Journal of Systematic Bacteriology*, 1984, 34(2):127-128.

Hopwood, et al., "Genetic manipulation of Streptomyces polyketide synthase genes for novel secondary metabolite production" *FEMS Microbiology Reviews*, 1995 16: 233-234.

Horan, A.C., "Aerobic Actinomycetes: A Continuing Source of Novel Natural Products" *Biotechnology* 1994, 23:3-30.

Jensen et al. "Strategies for the Discovery of Secondary Metabolites from Marine Bacteria: Ecological Perspectives" *Annu. Rev. Microbiology* 1994, 48:559-84.

Jensen P.R. et al., "Distribution of actinomycetes in nearshore tropical marine sediments" *Applied and Environmental Microbiology*, 1991, 57(4):1102-1108.

Jensen, P.R. et al, "The relative abundance and seawater requirements of gram-positive bacteria in near-shore tropical marine samples" *Microbial Ecology*, 1995, 29(3):249-257.

Jiang, Z. et al., "Antinoflavoside, A Novel Flavonoid-Like Glycoside Produced by a Marine Bacterium of the Genus Streptomyces", *Tetrahedron Letters*, 1997, 38(29):5065-5068.

Joseph, S.J., et al. "Laboratory Cultivation of Widespread and Previously Uncultured Soil Bacteria" *Appl. Environ Microbiol.* 2003, 69(12):7210-7215.

Koch, et al, "16S Ribosomal DNA Analysis of the genera Micromonospora, Actinoplanes" *Intl Journal of Systematic Bacteriology*, 1996, 46(3):765-768.

Beers, M. H. and Berkow, R., eds, "The Merck Manual of Diagnosis and Therapy", 17th Ed., 1999, published by Merck Research Laboratories, pp. 397-398, 948-949, 1916 and 1979-1981.

Mincer, T.J. et al., "Widespread and Persistent Populations of a Major New Marine Actinomycete Taxon in Ocean Sediments" *Appl, Environ. Microbio.* 2002, 68(10):5005-5011.

Moran et al., "Evidence for indigenous streptomyces populations in marine environment determined with a 16S rRNA probe" *Applied and Environmental Microbiology*, 1995, 61(10):3895-3700.

Nesterenko, O.A., et al. "Rhodococcus luteus nom., nov., and Rhodococcusmaris nom. nov." *Int'l Journal of Systematic Bacteriology*, 1982, 32(1): 1-14.

Nolan, R.D., et al., "Isolation and Screening of Actinomycetes" *Actinomycetes in Biotechnology* 1988, Academic Press, London, Chapter 1, pp. 1-32.

O'Donnel, A.G. , "Recognition of Novel Actinomycetes" *Actinomycetes in Biotechnology*, 1988, Academic Press, London, Chapter 3. 69-88.

Okami, et al., "Search and Discovery of New Antibiotics" *Actinomycetes in Biotechnology* 1988, Academic Press, London, Chapter 2, pp. 33-67.

Otoguro, M. et al., "An integrated method for the enrichment and selective isolation of Actinokineospora spp. In soil and plant litter" *J. Appl. Microbiol.* 2001, 92:118-130.

Peckham, M., Pinedo, H., Veronesi, U., eds. Oxford Textbook of Oncology, vol. 1, 1995, Oxford University Press, Oxford, pp. 447-453.

Page, R.D.M., "TreeView: An application to display phylogenetic trees on personal computers" *Comput. Appl. Biosci.* 1996, 12(4):357-358.

Rappe, et al. "Cultivation of the Ubiquitous SAR11 Marine Bacterioplankton Clade" *Natrue* 2002, 418:630-633.

Romero, F., et al. "Thiocoraline, a new depsipeptide with antitumor activity produced by a marine Micromonospora. I. Taxonomy, fermentation, isolation, and biological activies" *J. Antibiot.* 1997, 50(9) 734-737.

Stach, J.E.M., et al., "Statistical Approaches for Estimating Actinobacterial Diversity in Marine Sediment" *Appl, Environ. Microbiol.* 2003, 69(10):6189-6200.

Stach, J.E.M., et al., "New primers for the class Actinobacteria: application to marine and terrestrial environments" *Appl, Envrion. Microbiol.* 2003, 5(10)28-841.

Stackebrandt, E. et al., "Proposal for a new Hierarchic classification systems, Actinobacteriaclassis nov" *International Journal of Systematic Bacteriology* 1997 47(2):479-491.

Tang, L., et al., "Cloning and Hereologous Expression of the Epothilong Gene Cluster" *Science.* 2000, 287: 640-2.

Tauchi, T. et al, "Molecular mechanisms of resistance of leukemia to imatinib mesylate" *Leukemia Research*, 2004 28, Supplement 1: S39-45.

Thompson, et al. "Clustal W: Improving the sensitivity of progressive multiple sequence allignment through sequence weighting, position-specific gap penalties and weight matrix choice" *Nucleic Acids Research.* 1994, 22(22):4673-4680.

Versalovic, J. et al "Distribution of repetive DNA sequence in eubacteria an dapplication to fingerprinting of bacterial genmes" *Nucleic Acids Res.* 1991 19(24):6823-6831.

Ward, B. "How Many Species of Prokaryotes are There?" *PNAS* 2002 99(16):10234-10236.

Watve, M.G et al., "How many antibiotics are produced by the genus Streptomyces?" *Arch. Microbio.* 2001, 176:386-390.

Wheelis, M., et al. "On the Nature of Global Classification" *PNAS* 1992, 89: 2930-2934.

Woese, C.R., "Bacterial Evolution" *Microbiological Rev.* 1987, 51(2):221-271.

Weyland, H. "Actinomycetes in North Sea and Atlantic Ocean Sediments" *Nature*, 1969, 223:858.

Weyland, H. Distribution of actinomycetes on the Sea Floor. *Actinomycestes ZBL. Bakt.* 1981 Suppl 11: 185-193.

Williams, P.G., et al, "New cytotoix salinosporamides form the marine actinomycete *Salinispora tropica*" *J. of Organic Chemistry*, 2005, 70(16):6196-6203.

Zheng, Z., et al., "Detection of antitumor and antimicrobial activities in marine organism associated astinomycetes isolated from the Taiwan Strait, China" *FEMS Microbiology Letters*, 2000 188:87-91.

International Search Report and Written Opinion. International Application No. PCT/US2005/044091; International Filing Date: Feb. 12, 2005.

International Search Report. International Application No. PCT/US2004/019543; International Filing Date: Jun. 18, 2004.

Written Opinion. International Application No. PCT/US2004/019543; International Filing Date: Jun. 18, 2004.

International Search Report and Written Opinion. International Application No. PCT/US2005/014846; International Filing Date: Apr. 29, 2005.

International Search Report and Written Opinion for International Application No. PCT/US06/016104, filed Apr. 27, 2006.

Fenical, et al. "Marine Microorganisms as a Developing Resource for Drug Discovery", *Pharmaceutical News*, (2002), 9, 489-494.

Fenteany, et al., "Lactacystin, Proteasome Function, and Cell Fate,"J. Biol. Chem. (1998) 273:8548.

Goodfellow, et al., "Actinomycetes in Biotechnology", Okami, et al., ed., *Search and Discovery of New Antibiotics*. Academic Press: San Diego, (1988), pp.33-67.

Hardt, et al., "Neomarinone, and new cytotxic marinone derivatives, produced by a marine filmentous bacterium (actinomycetales)", *Tetrahedron Letters*, (2000) 41(13):2073-2076.

*The Merck Manual of Diagnosis and Therapy*, 17th Ed., published by Merck Research Laboratories, pp. 397-398, 948-949, 1916 and 1979-1981 (1999).

Mulholland et al., "A Concise Total Synthesis of Salinossporamide A," Org. Biomol. Chem., 2006, 4, 2845-6.

NCBI website, sequence for EF105548, http://www.ncbi.nlm.nih.gov/entrez/viewer.fcgi?db=nucleotide&val=118640518, 2 pages, downloaded Feb. 15, 2007.

NCBI website, sequence for AB242910, http://www.ncbi.nlm.nih.gov/entrez/viewer.fcgi?db=nucleotide&val=124300751, 2 pages, downloaded Feb. 15, 2007.

NCBI website, Sequence for EF191171, http://www.ncbi.nlm.nih.gov/entrez/viewer.fcgi?db=nucleotide&val=124014014, 2 Pages, downloaded Feb. 15, 2007.

Okami, Y., "The Search for Bioactive Metabolites from marine Bacteria", *J. Marine Biotechnology*, (1993) 1:59-65.

Stadler et al., "Cinnabaramides A-G: Analouges of Lactacystin and Salinosporamide from a Terrestrial Streptomycete," J. Nat. Prod. Feb. 2007;70(2):246-52.

International Search Report for PCT/US01/43758, International filing date Nov. 16, 2001.

Candian Publication No. 2429163, Filing Date Nov. 16, 2001.

Office Action in U.S. Appl. No. 10/871,368, Dated Nov. 1, 2006.

Office Action in U.S. Appl. No. 10/871,368, Dated May 15, 2007.

Office Action in U.S. Appl. No. 10/600,854, Dated Aug. 19, 2005.

Office Action in U.S. Appl. No. 10/600,854, Dated Dec. 30, 2004.

Office Action in U.S. Appl. No. 10/838,157, Dated Aug. 19, 2004.

Office Action in U.S. Appl. No. 11/147,622, Dated Dec. 2, 2005.

Office Action In U.S. Appl. No. 09/991,518, Dated Nov. 4, 2005.

Office Action in U.S. Appl. No. 09/991,518, Dated Jun. 27, 2005.

Office Action in U.S. Appl. No. 09/991,518, Dated Feb. 15, 2005.

Office Action in U.S. Appl. No. 09/991,518, Dated Sep. 15, 2003.

Office Action in U.S. Appl. No. 11/228,416, Dated Feb. 21, 2007.

Notice of Allowance in U.S. Appl. No. 10/600,854, Dated Sep. 28, 2006.

Notice of Allowance in U.S. Appl. No. 10/838,157, Dated Sep. 28, 2006.

Notice of Allowance in U.S. Appl. No. 11/147,622, Dated Sep. 29, 2006.

Notice of Allowance in U.S. Appl. No. 09/991,518, Dated Apr. 24, 2006.

* cited by examiner

II-3

II-4

II-5A

II-5B

II-8C

II-13C

II-18

II-19

II-20

II-21

II-22

II-24C

II-25

IV-3C

IV-3C

II-26

II-27

II-28

II-29

II-30

¹H-NMR of II-44

Formula I-7

¹H-NMR of the Compound of Formula II-47

¹H-NMR of the Compound of Formula II-38

¹H-NMR of the Compound of Formula II-51

[3.2.0] HETEROCYCLIC COMPOUNDS AND METHODS OF USING THE SAME

CROSS-REFERENCE TO RELATED APPLICATIONS

This application claims priority under 35 U.S.C. § 119(e) to U.S. Provisional Application Nos. 60/567,336, filed on Apr. 30, 2004; Ser. No. 60/580,838, filed on Jun. 18, 2004; Ser. No. 60/591,190, filed on Jul. 26, 2004; Ser. No. 60/627,462, filed on Nov. 12, 2004; Ser. No. 60/644,132, filed on Jan. 13, 2005; and Ser. No. 60/659,385, filed on Mar. 4, 2005; each of which is entitled [3.2.0] HETEROCYCLIC COMPOUNDS AND METHODS OF USING THE SAME; and each of which is incorporated herein by reference in its entirety.

BACKGROUND OF THE INVENTION

1. Field of the Invention

The present invention relates to certain compounds and to methods for the preparation and the use of certain compounds in the fields of chemistry and medicine. More specifically, the present invention relates to compounds and procedures for making and using compounds that are useful as anti-cancer, anti-inflammatory, and anti-microbial agents, and relates to pharmaceutical dosage forms comprising such compounds.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria, fungi and protozoa are becoming increasingly difficult to treat and cure. For example, more and more bacteria, fingi and protozoa are developing resistance to current antibiotics and chemotherapeutic agents. Examples of such microbes include *Bacillus, Leishmania, Plasmodium* and *Trypanosoma*.

Furthermore, a growing number of diseases and medical conditions are classified as inflammatory diseases. Such diseases include conditions such as asthma to cardiovascular diseases. These diseases continue to affect larger and larger numbers of people worldwide despite new therapies and medical advances.

Therefore, a need exists for additional chemotherapeutics, anti-microbial agents, and anti-inflammatory agents to treat cancer, inflammatory diseases and infectious disease. A continuing effort is being made by individual investigators, academia and companies to identify new, potentially useful chemotherapeutic and anti-microbial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY OF THE INVENTION

Disclosed herein are compounds, pharmaceutical compositions comprising such compounds, uses of such compounds and compositions, and methods for the preparation of such compounds, having the structure of Formulae I-VI:

Some embodiments relate to compounds having the structure of Formula I, and pharmaceutically acceptable salts and pro-drug esters thereof:

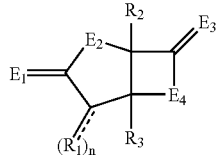

Formula I wherein the dashed line indicates that the designated bond is either a single bond or a double bond, and wherein $R_1$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including, for example, cyclohexylcarbinol, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. n is equal to 1 or 2, and if n is equal to 2, then $R_1$ can be the same or different;

wherein $R_2$, can be selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including, for example, cyclohexylcarbinol), cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl; wherein each of $E_1$, $E_2$, $E_3$ and $E_4$ can be a substituted or unsubstituted heteroatom; and with the proviso that Formula I is not Compound II-16 or Compound II-17.

In some embodiments, $R_2$ is not cyclohex-2-enyl carbinol when one of the $R_1$ substituents is ethyl or chloroethyl and $R_3$ is methyl.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

$R_2$ can be a formyl. For example, the compound may be:

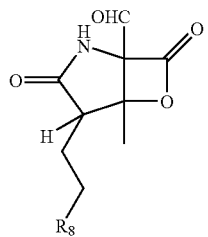

wherein $R_8$ is selected from the group consisting of H, F, Cl, Br, and I.

As another example, the compound maybe:

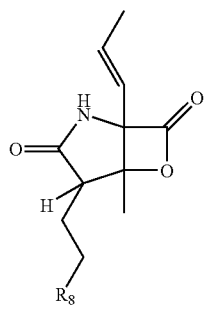

wherein $R_8$ is selected from the group consisting of H, F, Cl, Br, and I.

As a further example, the compound may be:

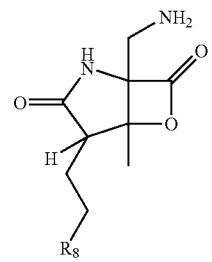

wherein $R_8$ is selected from the group consisting of H, F, Cl, Br, and I.

Also, $R_2$ can be a cyclohexenylmethylene or 3-methylenecyclohexene.

For example, the compound may be:

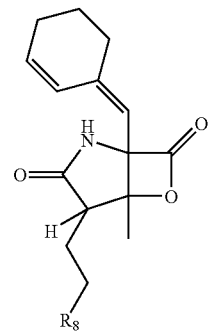

wherein $R_8$ is selected from the group consisting of H, F, Cl, Br, and I.

$R_2$ can be a cyclohexylalkylamine, a C-Cyclohexyl-methyleneamine, or a cyclohexanecarbaldehyde O-oxime.

For example, the compound may be:

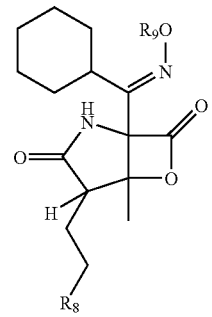

wherein $R_8$ is selected from the group consisting of H, F, Cl, Br, and I; and wherein $R_9$ is selected from the group consisting of hydrogen, substituted or unsubstituted variants of the following: alkyl, acyl, aryl and heteroaryl.

Furthermore, $R_2$ can be a cycloalkylacyl.

As an example, the compound may be:

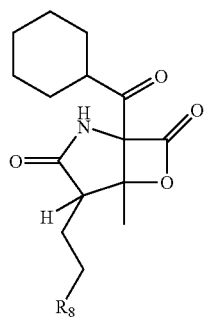

wherein $R_8$ is selected from the group consisting of H, F, Cl, I, and Br.

Further embodiments relate to compounds having the structure of Formula II, and pharmaceutically acceptable salts and pro-drug esters thereof:

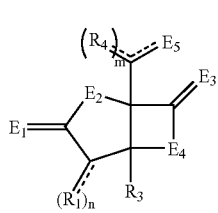

Formula II wherein the dashed lines indicates that the designated bond is either a single bond or a double bond, and wherein $R_1$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl where n is equal to 1 or 2, and if n is equal to 2, then $R_1$ can be the same or different;

wherein $R_3$ can be. selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;

wherein $R_4$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, and m is equal to 1 or 2, and if m is equal to 2, then $R_4$ can be the same or different;

wherein each of $E_1$, $E_2$, $E_3$, $E_4$ and $E_5$ can be a substituted or unsubstituted heteroatom; and with the proviso that Formula II is not Compound II-16 or Compound II-17. Some embodiments include the proviso that one $R_4$ is not cyclohex-2-enyl, if the other $R_4$ is hydrogen and if m and n are equal to 2, and if $R_3$ is methyl, and if one of the substituents $R_1$ is ethyl or chloroethyl while the other $R_1$ is hydrogen.

As an example, $E_5$ can be selected from the group consisting of OH, O, S, N, NH, $NH_2$, NOH, NHOH, $OR_{10}$, $SR_{11}$, $NR_{12}$, and $NHOR_{13}$, wherein each of $R_{10}$, $R_{11}$, $R_{12}$, and $R_{13}$ can be separately selected from the group consisting of hydrogen, and a substituted or unsubstituted alkyl, acyl, aryl, and heteroaryl.

n can be equal to 1 or 2, and where n is equal to 2, at least one $R_1$ can be $CH_2CH_2X$, wherein X can be selected from the group consisting of H, F, Cl, Br, and I.

As another example, $R_3$ can be methyl. Furthermore, $E_5$ can be OH. Each of $E_1$, $E_3$ and $E_4$ can be O and $E_2$ can be NH. At least one $R_4$ can be a cycloalkane or cycloalkene, for example. In another example, n is equal to 2 and at least one of the $R_1$ substituents is hydrogen and the other $R_1$ substituent is $CH_2CH_2X$, wherein X is selected from the group consisting of H, F, Cl Br, and I; wherein at least one $R_4$ is cyclohexane or cyclohexene; wherein $E_5$ is OH; wherein $R_3$ is methyl; and wherein each of $E_1$, $E_3$ and $E_4$ is O and $E_2$ is NH.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

As an example, the structure may be:

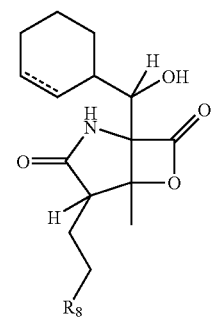

wherein $R_8$ is selected from the group consisting of H, F, Cl, Br and I.

At least one $R_4$ can be a di-substituted cyclohexane, for example,

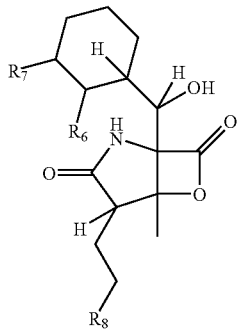

wherein $R_8$ is selected from the group consisting of H, F, Cl, Br and I.

$R_6$ and $R_7$ both can be OH.

At least one $R_4$ can be a 7-oxa-bicyclo[4.1.0]hept-2-yl, for example:

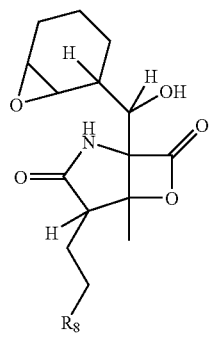

wherein $R_8$ is selected from the group consisting of H, F, Cl, Br, and I.

Also, at least one $R_4$ can be a substituted or an unsubstituted branched alkyl, for example the following compound:

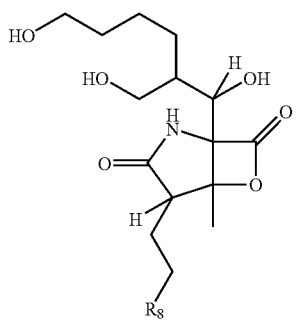

wherein $R_8$ is selected from the group consisting of H, F, Cl, Br and I.

Furhermore, at least one $R_4$ can be a cycloalkyl and $E_5$ can be an oxygen.

As an example, the compound may be:

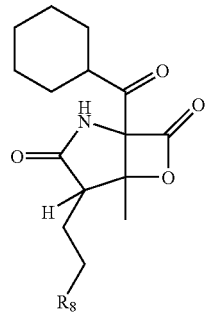

wherein $R_8$ is selected from the group consisting of H, F, Cl, I, and Br.

As a further example, the compound may be:

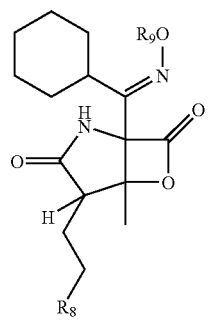

wherein $R_8$ is selected from the group consisting of H, F, Cl, Br, and I; and wherein $R_9$ can be selected from the group consisting of H, substituted and unsubstituted alkyl, substituted and unsubstituted aryl, and substituted and unsubstituted heteroaryl.

In still a further example, the compound may be:

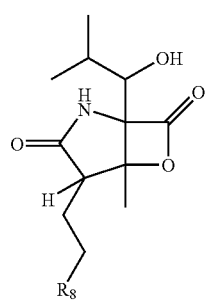

wherein $R_8$ is selected from the group consisting of H, F, Cl, Br, and I.

Also, at least one $R_4$ can be a cycloalkyl and $E_5$ can be $NH_2$. For example, the compound may be:

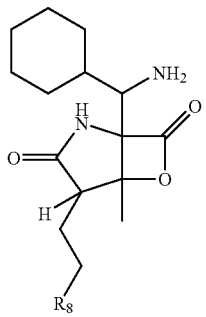

wherein $R_8$ is selected from the group consisting of H, F, Cl, Br, and I.

In still a further example, the compound can be a prodrug ester or thioester, for example, the compound may be:

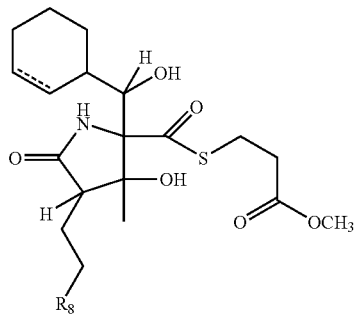

wherein $R_8$ is selected from the group consisting of H, F, Cl, Br, and I.

Other embodiments relate to compounds having the structure of Formula III, and pharmaceutically acceptable salts and pro-drug esters thereof:

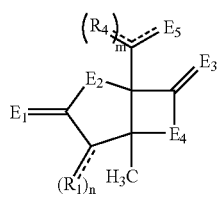

Formula III wherein the dashed lines indicates that the designated bond is either a single bond or a double bond, and wherein $R_1$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, and n is equal to 1 or 2, and if n is equal to 2, then $R_1$ can be the same or different;

wherein $R_4$ can be separately selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, and m is equal to 1 or 2, and if m is equal to 2, then $R_4$ can be the same or different; and wherein each of $E_1$, $E_2$, $E_3$, $E_4$ and $E_5$ is a substituted or unsubstituted heteroatom; and with the proviso that Formula III is not Compound II-16 or Compound II-17. Some embodiments include the proviso that one $R_4$ is not cyclohex-2-enyl, if the other $R_4$ is hydrogen and if m and n are equal to 2 and if one of the substituents $R_1$ is ethyl or chloroethyl while the other $R_1$ is hydrogen.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

Still further embodiments relate to compounds having the structure of Formula IV, and pharmaceutically acceptable salts and pro-drug esters thereof:

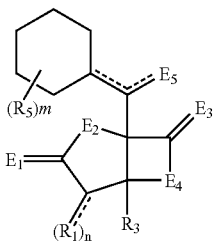

Formula IV wherein the dashed lines indicate that the designated bond is either a single bond or a double bond, and wherein $R_1$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, and n is equal to 1 or 2, and if n is equal to 2, then $R_1$ can be the same or different;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;

wherein $R_5$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, wherein m is 0, 1, 2, 3, 4, 5, 6, 7, 8, 9, 10, or 11 and if m is more than 1, then $R_5$ can be the same or different; and where the substituents $R_5$ can form a ring; and wherein each of $E_1$, $E_2$, $E_3$, $E_4$ and $E_5$ is a substituted or unsubstituted heteroatom.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

Other embodiments relate to compounds having the structure of Formula V, and pharmaceutically acceptable salts and pro-drug esters thereof:

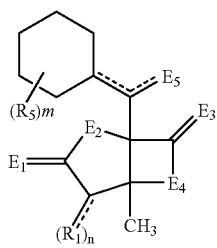

Formula V wherein the dashed line indicates that the designated bond is either a single bond or a double bond, and wherein $R_1$ can be selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, and n is equal to 1 or 2, and if n is equal to 2, then $R_1$ can be the same or different;

wherein $R_5$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, wherein m is 0, 1, 2, 3, 4, 5, 6, 7, 8, 9, 10, or 11, and if m is more than 1, then $R_5$ can be the same or different; and where the substituents $R_5$ can form a ring; and wherein each of $E_1$, $E_2$, $E_3$, $E_4$ and $E_5$ is a substituted or unsubstituted heteroatom.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

Other embodiments relate to compounds having the structure of Formula VI, and pharmaceutically acceptable salts and pro-drug esters thereof:

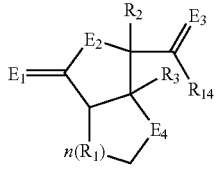

Formula VI wherein $R_1$ can be separately selected from the group consisting of a mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, phenyl, cycloalkylacyl, alkylthio, arylthio, oxysulfonyl, carboxy, thio, sulfoxide, sulfoneboronic acid esters, and halogenated alkyl including polyhalogenated alkyl. n is equal to 1 or 2, and if n is equal to 2, then $R_1$ can be the same or different;

wherein $R_2$, can be selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including, for example, cyclohexylcarbinol), cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl; wherein each of $E_1$, $E_2$, $E_3$ and $E_4$ can be a substituted or unsubstituted heteroatom.

In some embodiments, $R_2$ is not cyclohex-2-enyl carbinol when one of the $R_1$ substituents is ethyl or chloroethyl and $R_3$ is methyl.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred.

wherein $R_{14}$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, thioesters, sulfoxide, sulfone, sulfonate esters, thiocyano, and halogenated alkyl including polyhalogenated alkyl.

In some embodiments, preferably $R_{14}$ is an alkylthiol or substituted alkylthiol, and $E_3$ is an oxygen.

Some exemplary embodiments relate to compounds of Formula VI that have the following structure, and which are referred to as Formula VI-1:

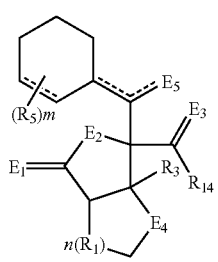

Formula VI-1 wherein $R_1$ can be separately selected from the group consisting of a mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, phenyl, cycloalkylacyl, alkylthio, arylthio, oxysulfonyl, carboxy, thio, sulfoxide, sulfone, sulfonate esters, thiocyano, boronic acid esters, and halogenated alkyl including polyhalogenated alkyl. n is equal to 1 or 2, and if n is equal to 2, then $R_1$ can be the same or different;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl; wherein each of $E_1$, $E_2$, $E_3$ and $E_4$ can be a substituted or unsubstituted heteroatom.

wherein $R_5$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, wherein m is 0, 1, 2, 3, 4, 5, 6, 7, 8, 9, 10, or 11 and if m is more than 1, then $R_5$ can be the same or different; and where the substituents $R_5$ can form a ring; and wherein each of $E_1$, $E_2$, $E_3$, $E_4$ and $E_5$ is a substituted or unsubstituted heteroatom.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred.

wherein $R_{14}$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, thioesters, sulfoxide, sulfone, sulfonate esters, thiocyano, and halogenated alkyl including polyhalogenated alkyl.

In some embodiments, preferably $R_{14}$ is an alkylthiol or substituted alkylthiol, and $E_3$ is an oxygen.

For example, the compound has the following structure VI-1A:

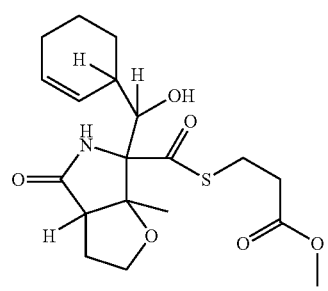

Formula VI-1A

Exemplary stereochemistry can be as follows:

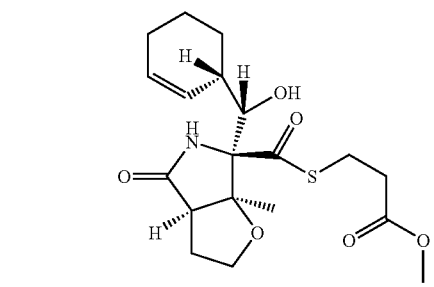

For example, an exemplary compound of Formula VI has the following structure and stereochemistry VI-1B:

Formula VI-1B

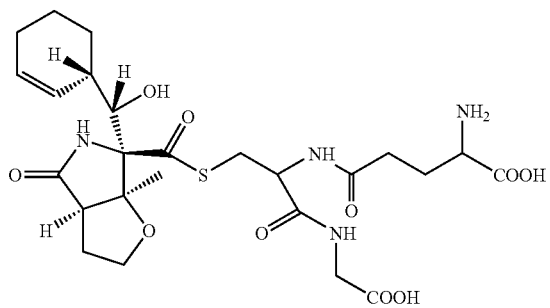

Another example, the compound of Formula VI has the following structure and stereochemistry VI-1C:

Formula VI-1C

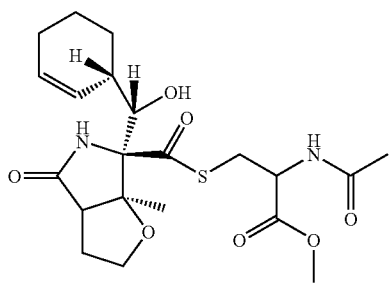

Some embodiments relate to pharmaceutical compositions that include a compound as described herein. The pharmaceutical compositions may further include an antimicrobial agent.

Other embodiments relate to methods of treating cancer. The methods may include, for example, administering a compound or composition as described herein, and pharmaceutically acceptable salts and pro-drug esters thereof. The methods may further include the steps of: identifying a subject that would benefit from administration of an anticancer agent; and performing the method on the subject. The cancer may be, for example, a multiple myeloma, a colorectal carcinoma, a prostate carcinoma, a breast adenocarcinoma, a non-small cell lung carcinoma, an ovarian carcinoma, a melanoma, and the like. The cancer can be a drug-resistant cancer, and the drug-resistant cancer may display at least one of the following: elevated levels of the P-glycoprotein efflux pump, increased expression of the multidrug-resistance associated protein 1 encoded by MRP1, reduced drug uptake, alteration of the drug's target or increasing repair of drug-induced DNA damage, alteration of the apoptotic pathway or the activation of cytochrome P450 enzymes. As an example, the drug-resistant cancer can be a sarcoma.

Still further embodiments relate to methods of inhibiting the growth of a cancer cell. The methods can include, for example, contacting a cancer cell with a compound or composition as described herein, and pharmaceutically acceptable salts and pro-drug esters thereof. The cancer cell may be, for example, a multiple myeloma, a colorectal carcinoma, a prostate carcinoma, a breast adenocarcinoma, a non-small cell lung carcinoma, an ovarian carcinoma, a melanoma, and the like.

Other embodiments relate to methods of inhibiting proteasome activity comprising the step contacting a cell with a compound or composition as described herein, and pharmaceutically acceptable salts and pro-drug esters thereof.

Further embodiments relate to methods of inhibiting NF-κB activation. The methods can include, for example, the step contacting a cell with a compound or composition as described herein, and pharmaceutically acceptable salts and pro-drug esters thereof.

Still other embodiments relate to methods for treating an inflammatory condition. The methods may include, for example, administering an effective amount of a compound or composition as described herein to a patient in need thereof. The inflammatory condition may be, for example, rheumatoid arthritis, asthma, multiple sclerosis, psoriasis, stroke, myocardial infarction, and the like.

Some embodiments relate to methods for treating a microbial illness which can include administering an effective amount of a compound or composition as described herein to a patient in need thereof. The microbial illness maybe caused, for example by *B. anthracis*, *Plasmodium*, *Leishmania*, and *Trypanosoma*.

Other embodiments relate to uses of one or more compounds of Formulae I, II, III, IV, V, or VI, and pharmaceutically acceptable salts and pro-drug esters thereof in the treatment of a cancer, an inflammatory condition, or a microbial infection. The one or more compounds is one or more of a compound of any of the compounds as described herein, and pharmaceutically acceptable salts and pro-drug esters thereof. The cancer can be, for example a multiple myeloma, a colorectal carcinoma, a prostate carcinoma, a breast adenocarcinoma, a non-small cell lung carcinoma, an ovarian carcinoma or a melanoma. Also, the cancer can be a drug-resistant cancer, for example, one that displays at least one of the following: elevated levels of the P-glycoprotein efflux pump, increased expression of the multidrug-resistance associated protein 1 encoded by MRP1, reduced drug uptake, alteration of the drug's target or increasing repair of drug-induced DNA damage, alteration of the apoptotic pathway and the activation of cytochrome P450 enzymes. The inflammatory condition can be, for example, rheumatoid arthritis, asthma, multiple sclerosis, psoriasis, stroke, or myocardial infarction. The microbial infection can be, for example, caused by *B. anthracis*, *Plasmodium*, *Leishmania*, or *Trypanosoma*.

Still further embodiments relate to uses of one or more compounds of Formulae I, II, III, IV, V, or VI as described herein, and pharmaceutically acceptable salts and pro-drug esters thereof, for the inhibition of angiogenesis, inhibition of a proteasome activity, or inhibition of NF-κB activation.

Some embodiments relate to uses of a compound of Formula I, II, III, IV, V, or VI, and pharmaceutically acceptable salts and pro-drug esters thereof, in the preparation of medicament for the treatment of a cancer, an inflammatory condition, or a microbial infection or for the inhibition of angiogenesis, a proteasome activity, or NF-κB activation. The uses can further include the use of a chemotherapeutic agent, an anti-angiogenic agent, an anti-inflammatory agent, or a proteasome inhibitor.

BRIEF DESCRIPTION OF THE DRAWINGS

The accompanying drawings, which are incorporated in and form part of the specification, merely illustrate certain preferred embodiments of the present invention. Together with the remainder of the specification, they are meant to serve to explain preferred modes of making certain compounds of the invention to those of skilled in the art. In the drawings.

DETAILED DESCRIPTION OF THE PREFERRED EMBODIMENT

Figure 1:
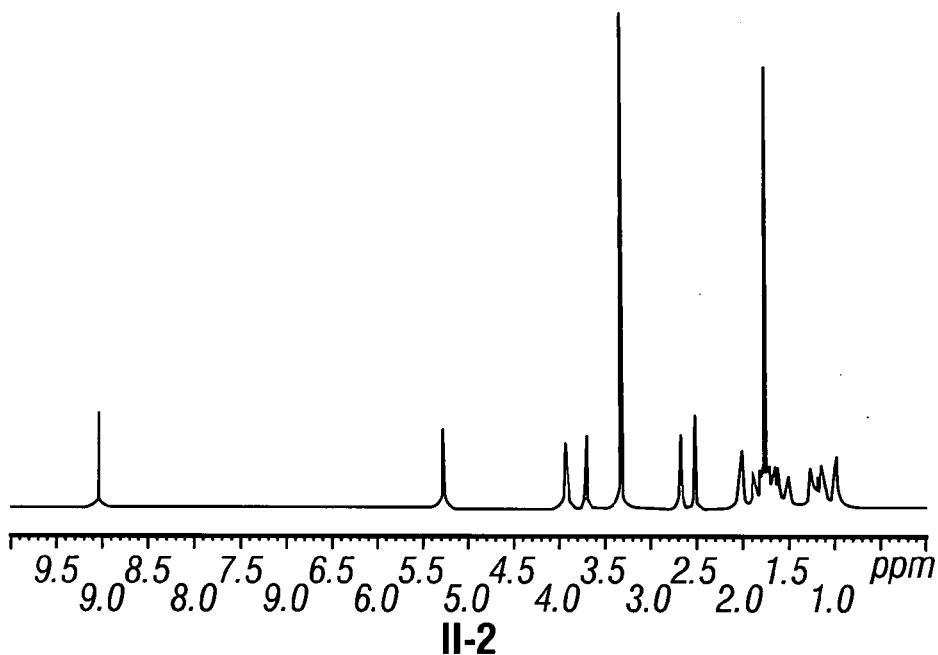
FIG. 1 depicts the $^1$H NMR spectrum of a compound having structure Formula II-2.

Numerous references are cited herein. The references cited herein, including the U.S. patents cited herein, are each to be considered incorporated by reference in their entirety into this specification.

Embodiments of the invention include, but are not limited to, providing a method for the preparation of compounds, including novel compounds, for example, including compounds described herein and analogs thereof, and to providing a method for producing pharmaceutically acceptable anti-microbial, anti-cancer, and anti-inflammatory compositions, for example. The methods can include the compositions in relatively high yield, wherein the compounds and/or their derivatives are among the active ingredients in these compositions. Other embodiments relate to providing novel compounds not obtainable by currently available methods. Furthermore, embodiments relate to methods of treating cancer, inflammation, and infectious diseases, particularly those affecting humans. The methods may include, for example, the step of administering an effective amount of a member of a class of new compounds. Preferred embodiments relate to the compounds and methods of making and using such compounds disclosed herein, but not necessarily in all embodiments of the present invention, these objectives are met.

For the compounds described herein, each stereogenic carbon can be of R or S configuration. Although the specific compounds exemplified in this application can be depicted in a particular configuration, compounds having either the opposite stereochemistry at any given chiral center or mixtures thereof are also envisioned. When chiral centers are found in the derivatives of this invention, it is to be understood that the compounds encompasses all possible stereoisomers.

Compounds of Formula I

Some embodiments provide compounds, and methods of producing a class of compounds, pharmaceutically acceptable salts and pro-drug esters thereof, wherein the compounds are represented by Formula I:

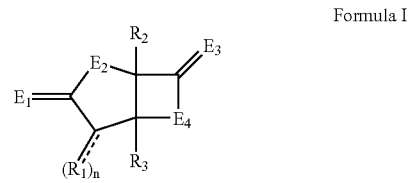

Formula I

In certain embodiments the substituent(s) $R_1$, $R_2$, and $R_3$ separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including for example, cyclohexylcarbinol), cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. Further, in certain embodiments, each of $E_1$, $E_2$, $E_3$ and $E_4$ can be a heteroatom or substituted heteroatoms, for example, a heteroatom separately selected from the group consisting of nitrogen, sulfur and oxygen. The dashed line indicates that the designated bond is either a single bond or a double bond. In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

In some embodiments n can be equal to 1 or equal to 2. When n is equal to 2, the substituents can be the same or can be different. Also, some embodiments include the proviso that $R_2$ is not cyclohex-2-enyl-carbinol or substituted cyclohex-2-enyl-carbinol. Also, some embodiments include the proviso that Formula I is not Compound II-16 or Compound II-17. Other embodiments include the proviso that $R_2$ is not cyclohex-2-enyl-carbinol, when $R_3$ is methyl. Furthermore, in some embodiments $R_3$ is not hydrogen.

Preferably, $R_2$ can be a formyl. For example, the compound may have the following structure I-1:

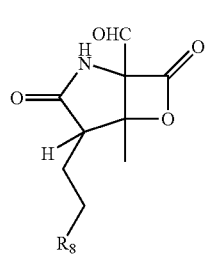

Formula I-1

$R_8$ may include, for example, hydrogen, fluorine, chlorine, bromine and iodine.

Preferably, the structure of Formula I-1 may have the following stereochemistry:

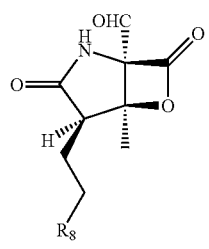

$R_8$ may include, for example, hydrogen, fluorine, chlorine, bromine and iodine.

Preferably, $R_2$ can be a carbinol. For example, the compound may have the following structure I-2:

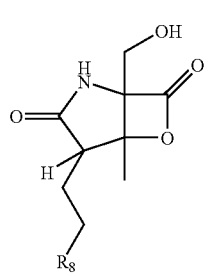

Formula I-2

$R_8$ may include, for example, hydrogen, fluorine, chlorine, bromine and iodine.

As an example, the structure of Formula I-2 may have the following stereochemistry:

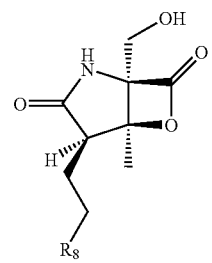

$R_8$ may include, for example, hydrogen, fluorine, chlorine, bromine and iodine.

As exemplary compound of Formula I can be the compound having the following structure I-3:

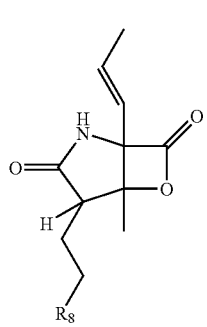

Formula I-3

$R_8$ may include, for example, hydrogen, fluorine, chlorine, bromine and iodine.

The compound of Formula I-3 may have the following stereochemical structure:

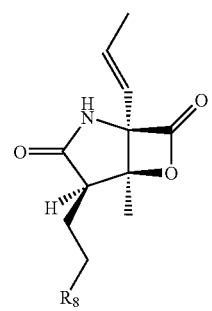

$R_8$ may include, for example, hydrogen, fluorine, chlorine, bromine and iodine.

Another exemplary compound Formula I can be the compound having the following structure I-4:

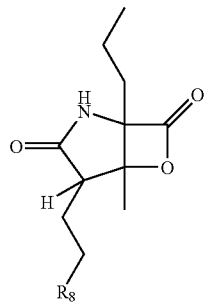

Formula I-4

$R_8$ may include, for example, hydrogen, fluorine, chlorine, bromine and iodine.

Preferably, the compound of Formula I-4 may have the following stereochemical structure:

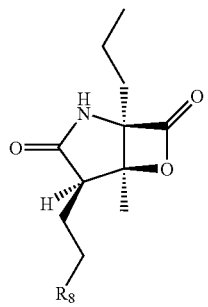

$R_8$ may include, for example, hydrogen, fluorine, chlorine, bromine and iodine.

Still a further exemplary compound of Formula I is the compound having the following structure I-5:

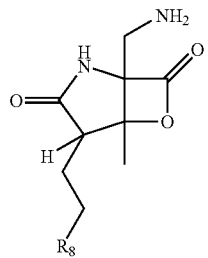

Formula I-5

$R_9$ may include, for example, hydrogen, fluorine, chlorine, bromine and iodine.

For example, the compound of Formula I-5 may have the following stereochemistry:

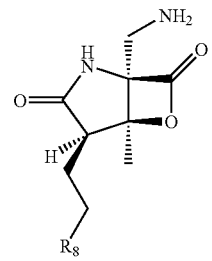

$R_8$ may include, for example, hydrogen, fluorine, chlorine, bromine and iodine.

In some embodiments, $R_2$ of Formula I may be, for example, a cyclohex-2-enylidenemethyl. For example, the compound may have the following structure of Formula I-6:

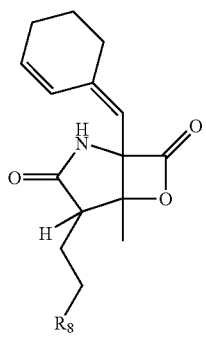

Formula I-6

$R_8$ may include, for example, hydrogen, fluorine, chlorine, bromine and iodine.

Preferably, the compound of Formula I-6 may have the following stereochemistry:

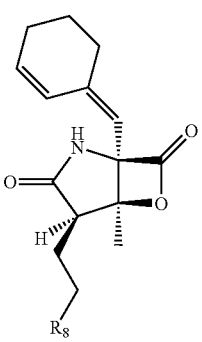

$R_8$ may include, for example, hydrogen, fluorine, chlorine, bromine and iodine.

In further embodiments, $R_2$ of Formula I can be, for example, a cyclohex-2-enylmethyl. For example, the compound may have the following structure of Formula I-7:

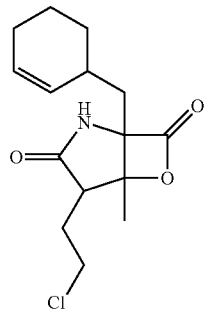

Formula I-7

$R_8$ may include, for example, hydrogen, fluorine, chlorine, bromine and iodine.

Preferably, the compound of Formula I-7 may have the following stereochemistry:

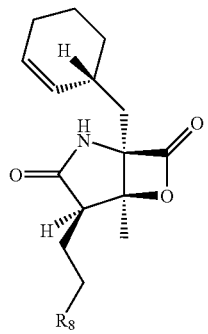

$R_8$ may include, for example, hydrogen, fluorine, chlorine, bromine and iodine.

In other embodiments, $R_2$ can be a cyclohexylalkylamine.

Also, in other embodiments, $R_2$ can be a C-Cyclohexylmethyleneamine. In others, $R_2$ can be a cyclohexanecarbaldehyde O-oxime.

Furthermore, in some embodiments, $R_2$ can be a cycloalkylacyl.

Compounds of Formula II

Other embodiments provide compounds, and methods of producing a class of compounds, pharmaceutically acceptable salts and pro-drug esters thereof, wherein the compounds are represented by Formula II:

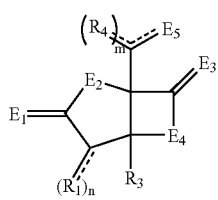

Formula II

In certain embodiments the substituent(s) $R_1$, $R_3$, and $R_4$ separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. Further, in certain embodiments, each of $E_1$, $E_2$, $E_3$ and $E_4$ can be a substituted or unsubstituted heteroatom. For example, the heteroatom can be nitrogen, sulfur and oxygen. The dashed line indicates that the designated bond is either a single bond or a double bond.

In some embodiments n or m can be equal to 1, while in others it can be equal to 2. When n or m is equal to 2, the substituents can be the same or can be different. Also, some embodiments include the proviso that Formula II is not Compound II-16 or Compound II-17. Further embodiments include the proviso that $R_4$ is not cyclohex-2-enyl or substituted cyclohex-2-enyl. Also, some embodiments include the proviso that $R_4$ is not cyclohex-2-enyl, when $R_3$ is methyl. Furthermore, in some embodiments $R_3$ is not a hydrogen.

$E_5$ may be, for example, OH, O, $OR_{10}$, S, $SR_{11}$, $SO_2R_{11}$, NH, $NH_2$, NOH, NHOH, $NR_{12}$, and $NHOR_{13}$, wherein $R_{10-13}$ may separately include, for example, hydrogen, alkyl, substituted alkyl, aryl, heteroaryl and the like. Also, $R_1$ can be $CH_2CH_2X$, wherein X may be, for example, H, F, Cl, Br, and I. $R_3$ can be methyl. Furthermore, $R_4$ can be cyclohexyl. Also, each of $E_1$, $E_3$ and $E_4$ can be O and $E_2$ can be NH. Preferably, $R_1$ can be $CH_2CH_2X$, wherein X is selected from the group consisting of H, F, Cl Br, and I; wherein $R_4$ may include a cyclohexyl; wherein $R_3$ can be methyl; and wherein each of $E_1$, $E_3$ and $E_4$ can be O and $E_2$ can be NH.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

For example, an exemplary compound of Formula II has the following structure II-1:

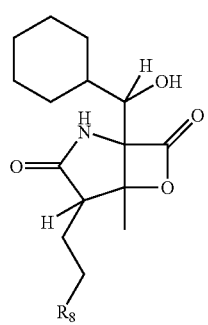

Formula II-1

$R_8$ may include, for example, hydrogen, fluorine, chlorine, bromine and iodine.

Exemplary stereochemistry can be as follows:

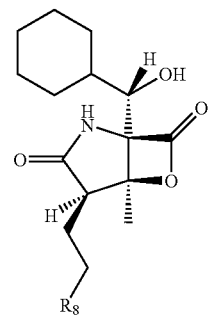

In preferred embodiments, the compound of Formula II has any of the following structures II-2, II-3 or II-4, respectively:

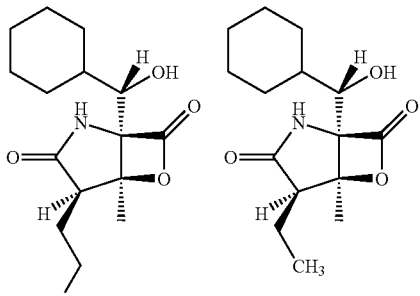

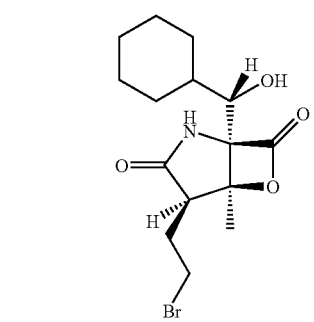

It should be noted that the stereochemistry of the above structures can be changed to the opposite stereochemistry at one or more of the chiral centers. For example, some embodiments include the following structures shown without stereochemistry:

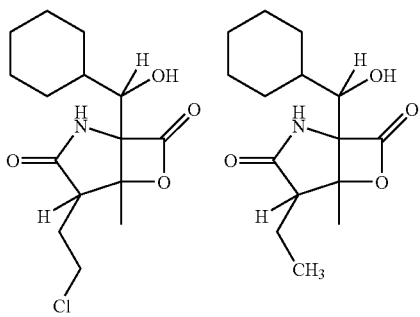

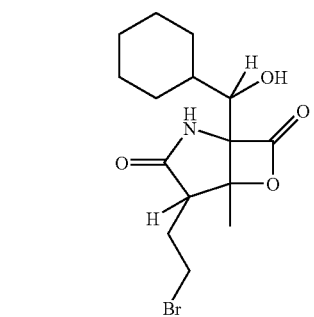

In other embodiments wherein $R_4$ can be 7-oxa-bicyclo [4.1.0]hept-2-yl. An exemplary compound of Formula II is the following structure II-5:

Formula II-5

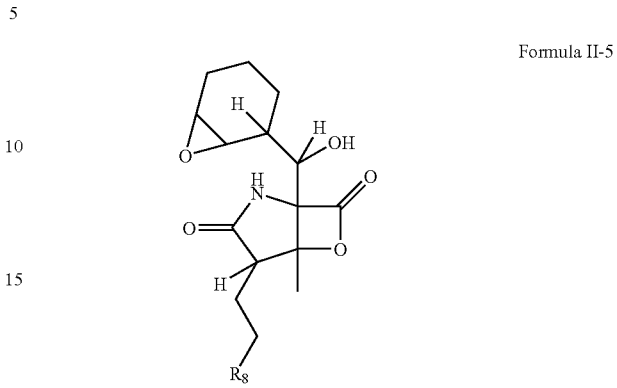

$R_8$ may include, for example, hydrogen, fluorine, chlorine, bromine and iodine.

The following are examples of compounds having the structure of Formula II-5:

Formulae II-5A and II-5B

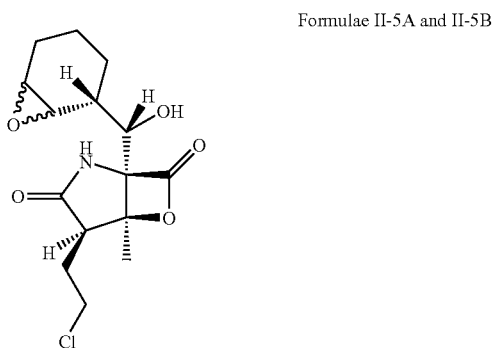

In still further embodiments, $R_4$ may include a substituted or an unsubstituted branched alkyl. For example, a compound of Formula II can be the following structure II-6:

Formula II-6

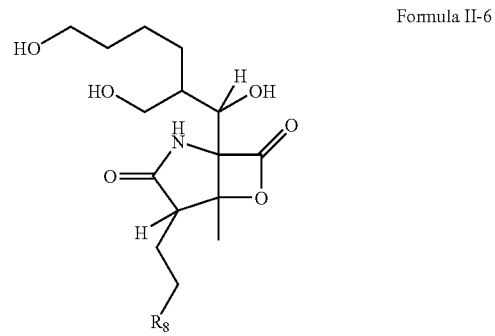

$R_8$ may include, for example, hydrogen, fluorine, chlorine, bromine and iodine.

The following is exemplary stereochemistry for a compound having the structure of Formula II-6:

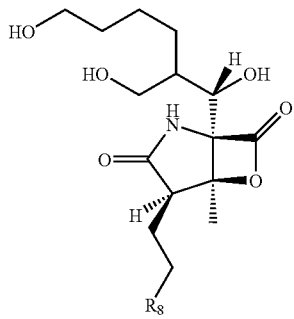

As another example, the compound of Formula II can be the following structure II-7:

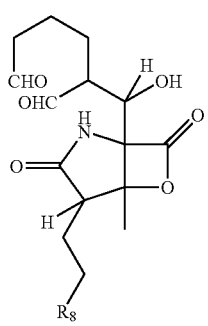

Formula II-7

$R_8$ may include, for example, hydrogen, fluorine, chlorine, bromine and iodine.

The following is exemplary stereochemistry for a compound having the structure of Formula II-7:

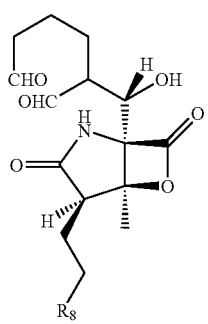

In other embodiments, $R_4$ can be a cycloalkyl and $E_5$ can be an oxygen. An exemplary compound of Formula II can be the following structure II-8:

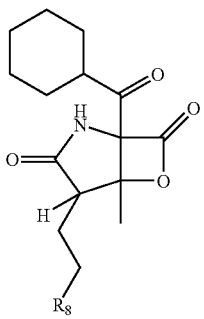

Formula II-8

$R_8$ may include, for example, hydrogen (II-8A), fluorine (II-8B), chlorine (II-8C), bromine (II-8D) and iodine (II-8E).

The following is exemplary stereochemistry for a compound having the structure of Formula II-8:

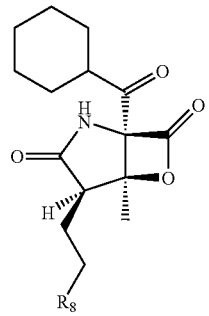

In some embodiments E5 can be an amine oxide, giving rise to an oxime. An exemplary compound of Formula II has the following structure II-9:

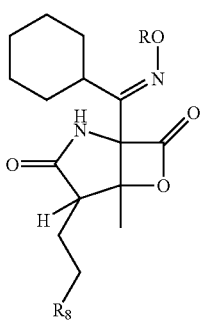

Formula II-9

$R_8$ may include, for example, hydrogen, fluorine, chlorine, bromine and iodine; R can be hydrogen, alkyl, or substituted alkyl, for example.

The following is exemplary stereochemistry for a compound having the structure of Formula II-9:

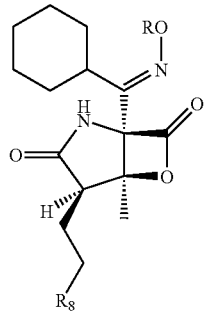

A further exemplary compound of Formula II has the following structure II-10:

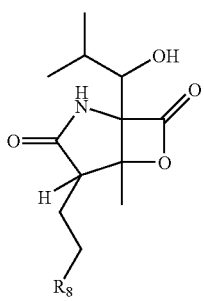

Formula II-10

R$_8$ may include, for example, hydrogen, fluorine, chlorine, bromine and iodine.

The following is exemplary stereochemistry for a compound having the structure of Formula II-10 (wavy bond indicates that any stereochemistry is allowed):

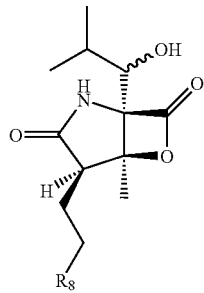

In some embodiments, E$_5$ can be NH$_2$. An exemplary compound of Formula II has the following structure II-11:

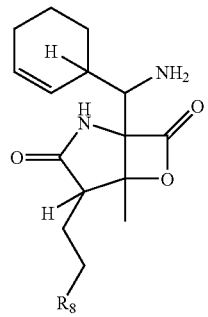

Formula II-11

R$_8$ may include, for example, hydrogen, fluorine, chlorine, bromine and iodine.

The following is exemplary stereochemistry for a compound having the structure of Formula II-11:

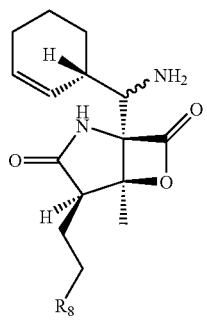

In some embodiments, R$_4$ may include a cycloalkyl and E$_5$ can be NH$_2$. An exemplary compound of Formula II has the following structure II-12:

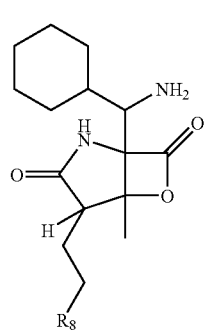

Formula II-12

R$_8$ may include, for example, hydrogen, fluorine, chlorine, bromine and iodine.

The following is exemplary stereochemistry for a compound having the structure of Formula II-12:

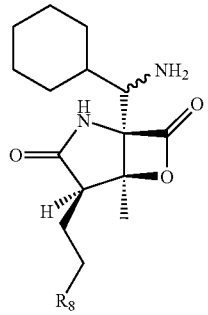

A further exemplary compound of Formula II has the following structure II-13:

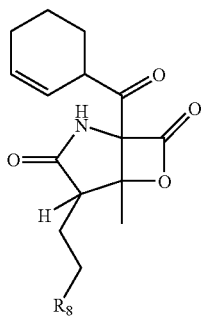

Formula II-13

$R_8$ may include, for example, hydrogen (II-13A), fluorine (II-13B), chlorine (II-13C), bromine (II-13D) and iodine (II-13E).

The following is exemplary stereochemistry for a compound having the structure of Formula II-13:

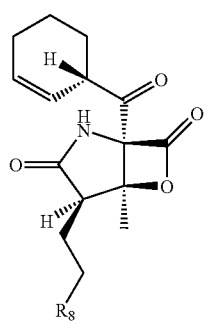

A still further exemplary compound of Formula II has the following structure II-14:

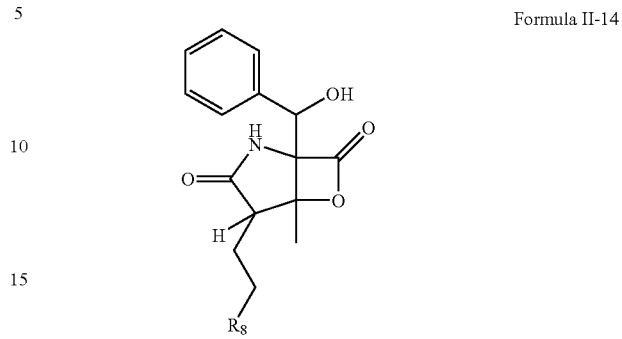

Formula II-14

$R_8$ may include, for example, hydrogen, fluorine, chlorine, bromine and iodine.

The following is exemplary stereochemistry for a compound having the structure of Formula II-14:

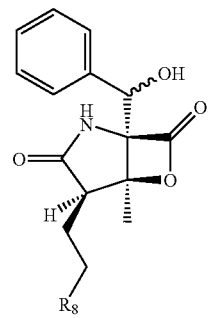

In some embodiments, the compounds of Formula II, may include as $R_4$ at least one cycloalkene, for example. Furthermore, in some embodiments, the compounds may include a hydroxy at $E_5$, for example. A further exemplary compound of Formula II has the following structure II-15:

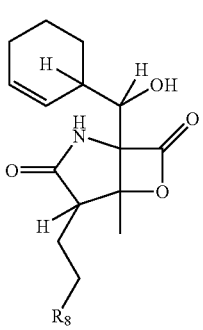

Formula II-15

$R_8$ may include, for example, hydrogen, fluorine, chlorine, bromine and iodine. In some embodiments, $R_8$ does not include hydrogen or chlorine.

Exemplary stereochemistry can be as follows:

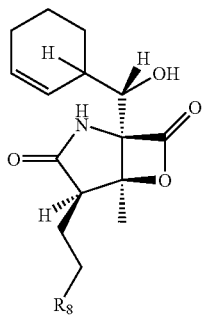

The following is exemplary stereochemistry for compounds having the structures II-18 and II-19, respectively:

II-18

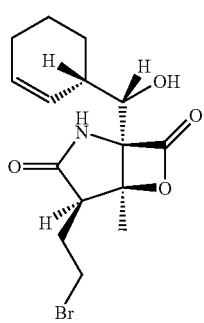

II-19

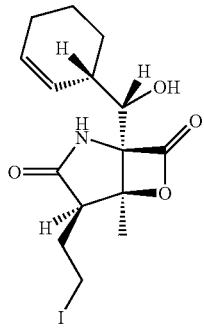

The compounds of Formulae II-18 and II-19 can be obtained by fermentation, synthesis, or semi-synthesis and isolated/purified as set forth below. Furthermore, the compounds of Formulae II-18 and II-19 can be used, and are referred to, as "starting materials" to make other compounds described herein.

In some embodiments, the compounds of Formula II, may include a methyl group as $R_1$, for example. A further exemplary compound, Formula II-20, has the following structure and stereochemistry:

II-20

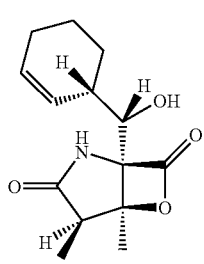

In some embodiments, the compounds of Formula II, may include hydroxyethyl as $R_1$, for example. A further exemplary compound, Formula II-21, has the following structure and stereochemistry:

II-21

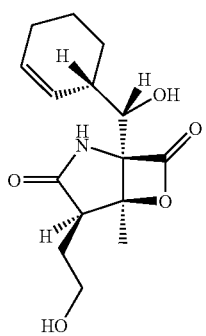

In some embodiments, the hydroxyl group of Formula II-21 can be esterified such that $R_1$ may include ethylpropionate, for example. An exemplary compound, Formula II-22, has the following structure and stereochemistry:

II-22

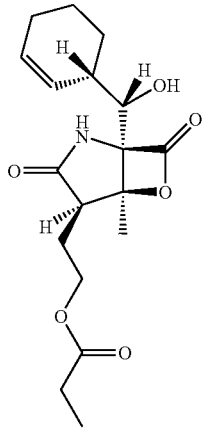

In some embodiments, the compounds of Formula II may include an ethyl group as $R_3$, for example. A further exemplary compound of Formula II has the following structure II-23:

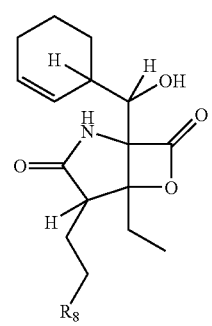

$R_8$ may include, for example, hydrogen, fluorine, chlorine, bromine and iodine. Exemplary stereochemistry can be as follows:

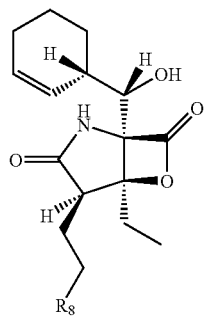

In some embodiments, the compounds of Formula II-23 may have the following structure and stereochemistry, exemplified by Formula II-24C, where $R_3$ is ethyl and $R_8$ is chlorine:

II-24C

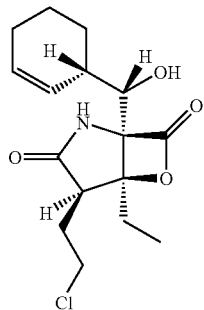

In some embodiments, the compounds of Formula II-15 may have the following stereochemistry, exemplified by the compound of Formula II-25, where $R_8$ is chlorine:

II-25

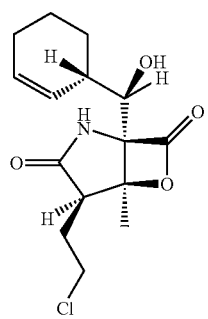

In some embodiments, the compound of Formula II-15 may have the following stereochemistry, exemplified by the compound of Formula II-26, where $R_8$ is chlorine:

II-26

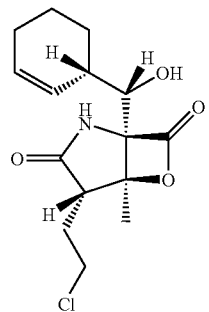

In some embodiments, the compound of Formula II may have the following structure and stereochemistry, exemplified by Formula II-27, where $R_1$ is ethyl:

II-27

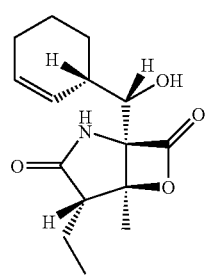

In some embodiments, the compound of Formula II may have the following structure (shown without stereochemistry and with exemplary stereochemistry), exemplified by Formula II-28, where $R_1$ is methyl:

II-28

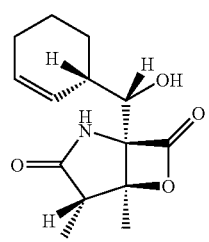

II-28

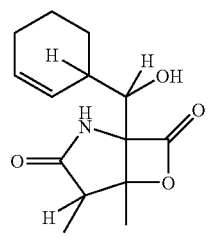

In some embodiments, the compounds of Formula II may include azidoethyl as $R_1$, for example. A further exemplary compound, Formula II-29, has the following structure and stereochemistry:

II-29

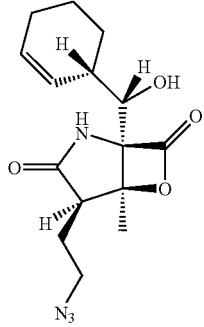

In some embodiments, the compounds of Formula II may include propyl as $R_1$, for example. A further exemplary compound, Formula II-30, has the following structure and stereochemistry:

II-30

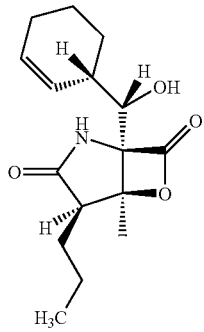

Still further exemplary compounds, Formulae II-31 and II-32, have the following structure and stereochemistry:

Formula II-31 and II-32

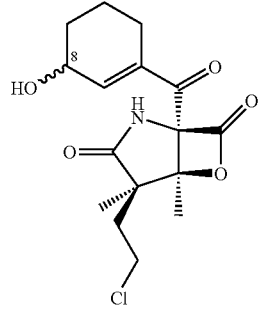

Other exemplary compounds, Formulae II-33, II-34, II-35 and II-36, have the following structure and stereochemistry:

Formula II-33-II-36

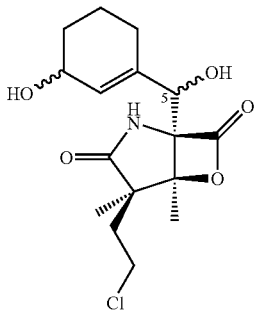

In some embodiments, the compound of Formula II may include cyanoethyl as $R_1$; for example, the compound of Formula II-37 has the following structure and stereochemistry:

II-37

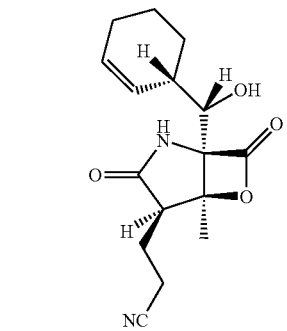

In another embodiment, the compound of Formula II may include ethylthiocyanate as $R_1$; for example, the compound of Formula II-38 has the following structure and stereochemistry:

II-38

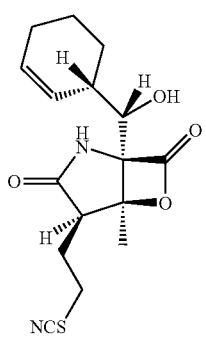

In some embodiments, the compounds of Formula II may include a thiol as $R_1$, for example. A further exemplary compound, Formula II-39, has the following structure and stereochemistry, where R=H, alkyl, aryl, or substituted alkyl or aryl:

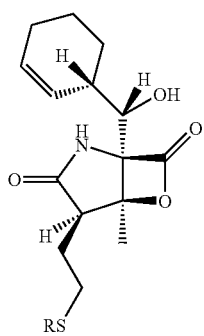

II-39

In a further exemplary compound, the sulfur of the compound of Formula II-39 can be oxidized to a sulfoxide (n=1) or sulfone (n=2), for example, as in the compound of Formula II-40:

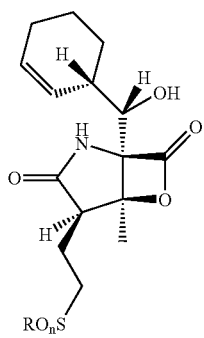

II-40

In some embodiments, the substituent $R_1$ of the compound of Formula II may include a leaving group, for example, a halogen, as in compounds II-18 or II-19, or another leaving group, such as a sulfonate ester. One example is the methane sulfonate (mesylate) of Formula II-41:

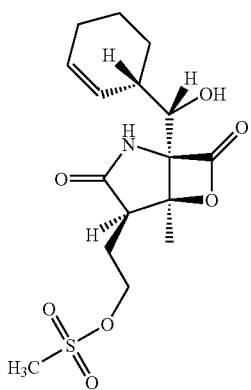

II-41

In some embodiments, the substituent $R_1$ of the compound of Formula II may include electron acceptors. The electron acceptor may be, for example, a Lewis acid, such as a boronic acid or ester. An exemplary compound, Formula II-42, has the following structure and stereochemistry, where n=0, 1, 2, 3, 4, 5, or 6, for example, and where R=H or alkyl, for example:

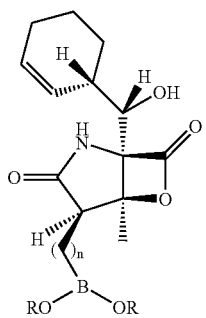

II-42

Further exemplary compounds of Formula II-42 are the compounds of Formula II-42A, where n=2 and R=H, and the compound of Formula II-42B, where n=1 and R=H:

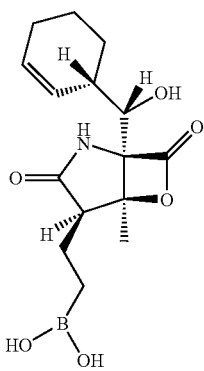

II-42A

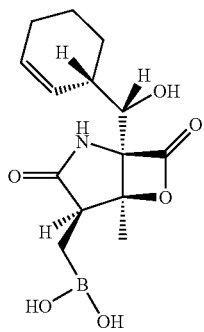

II-42B

In some embodiments where the substituent $R_1$ of the compound of Formula II includes an electron acceptor, the electron acceptor may be, for example, a Michael acceptor. An exemplary compound, Formula II-43 has the following structure, where n=0, 1, 2, 3, 4, 5, 6, and where Z is an electron withdrawing group, for example, CHO, COR, COOR, CONH$_2$, CN, NO$_2$, SOR, SO$_2$R, etc:

Other exemplary compound, Formula II-49 can have the following structure and stereochemistry:

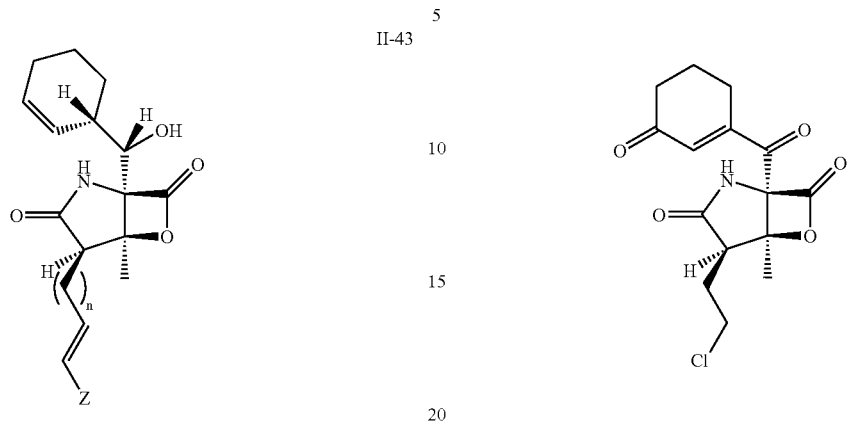

A further exemplary compound of Formula II-43 is the compound of Formula II-43A, where n=1 and Z=CO$_2$CH$_3$:

In some embodiments, the compounds can be prodrug esters or thioesters of the compounds of Formula II. For example, the compound of Formula II-44 (a prodrug thioester of the compound of Formula II-16) has the following structure and stereochemistry:

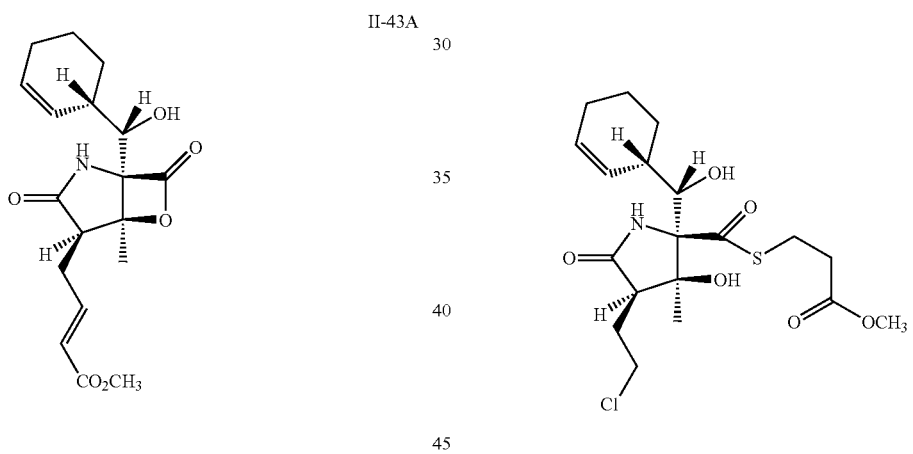

In some embodiments, the compounds of Formula II may include an alkenyl group as R$_1$, for example, ethylenyl. A further exemplary compound, Formula II-46, has the following structure and stereochemistry:

In another example, the compound of Formula II-47 (a prodrug thioester of the compound of Formula II-17) has the following structure and stereochemistry:

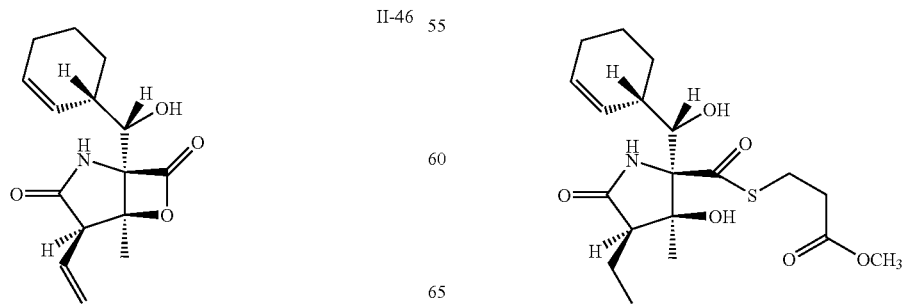

In yet another example, the compound of Formula II-48 has the following structure and stereochemistry:

II-48

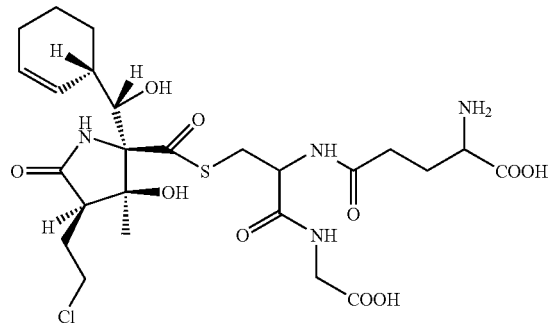

In another example, the compound of Formula II-50 (prodrug ester of the compound of Formula II-16) has the following structure and stereochemistry:

II-50

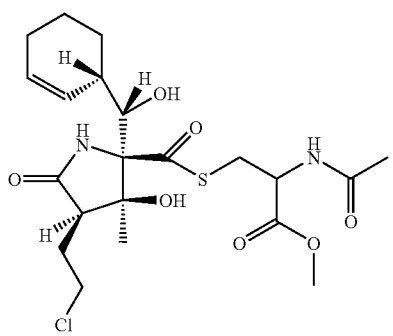

Compounds of Formula III

Other embodiments provide compounds, and methods of producing a class of compounds, pharmaceutically acceptable salts and pro-drug esters thereof, wherein the compounds are represented by Formula III:

Formula III

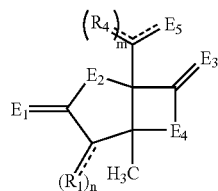

In certain embodiments, the substituent(s) $R_1$ may include, for example, a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. For example, n can be equal to 1 or 2. When n is equal to 2, the substituents can be the same or can be different. The dashed line indicates that the designated bond is either a single bond or a double bond.

In certain embodiments, $R_4$ may be, for example, hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. For example, m can be equal to 1 or 2. When m is equal to 2, the substituents can be the same or can be different. Some embodiments include the proviso that Formula III is not Compound II-16 or Compound II-17. Further embodiments include the proviso that $R_4$ is not cyclohex-2-enyl or substituted cyclohex-2-enyl. Also, each of $E_1$, $E_2$, $E_3$, $E_4$ and $E_5$ may be, for example, a heteroatom or substituted heteroatom. For example, the heteroatom can be nitrogen, sulfur or oxygen.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

Compounds of Formula IV

Other embodiments provide compounds, and methods of producing a class of compounds, pharmaceutically acceptable salts and pro-drug esters thereof, wherein the compounds are represented by Formula IV:

Formula IV

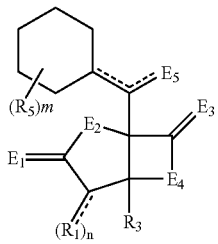

In certain embodiments, the substituent(s) $R_1$, $R_3$, and $R_5$ may separately include a hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. Also, each of $E_1$, $E_2$, $E_3$, $E_4$ and $E_5$ can be a heteroatom or substituted heteroatom, for example, nitrogen, sulfur or oxygen. In some embodiments, $R_3$ is not a hydrogen. n is equal to 1 or 2. When n is equal to 2, the substituents can be the same or can be different. Also, m can be 0, 1, 2, 3, 4, 5, 6, 7, 8, 9, 10, or 11 and if m is more than 1, then $R_5$ can be the same or different. Furthermore, the substituents $R_5$ may form a ring, for example, an epoxide. The dashed line indicates that the designated bond is either a single bond or a double bond.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

In some embodiments, the substituents $R_5$ may give rise to, for example, a di-substituted cyclohexane. An exemplary compound of Formula IV is the following structure IV-1, with and without exemplary stereochemistry (the wavy bond lines indicate that any stereochemical orientation is allowed):

Formula IV-1

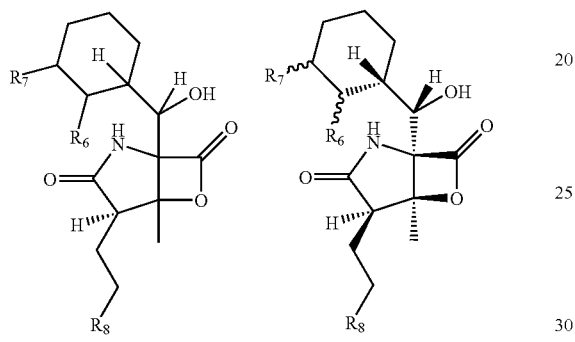

$R_8$ may include, for example, hydrogen, fluorine, chlorine, bromine and iodine. The substituent(s) $R_6$ and $R_7$ may separately include a hydrogen, a halogen, a mono-substituted, a poly-substituted or an unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. Further, $R_6$ and $R_7$ both can be the same or different.

For example, an exemplary compound of Formula IV has the following structure IV-2:

Formula IV-2

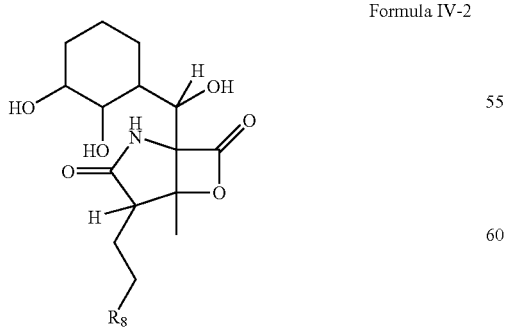

$R_8$ may include, for example, hydrogen, fluorine, chlorine, bromine and iodine.

Exemplary stereochemistry can be as follows:

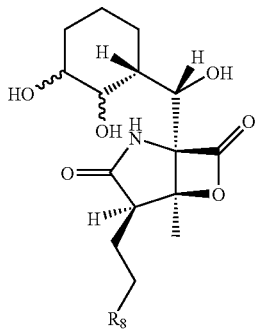

For example, an exemplary compound of Formula IV has the following structure IV-3:

Formula IV-3

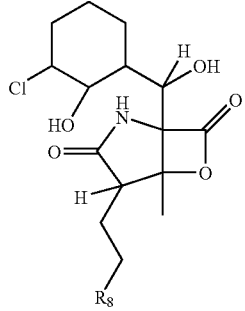

$R_8$ may include, for example, hydrogen (IV-3A), fluorine (IV-3B), chlorine (IV-3C), bromine (IV-3D) and iodine (IV-3E).

Exemplary stereochemistry can be as follows:

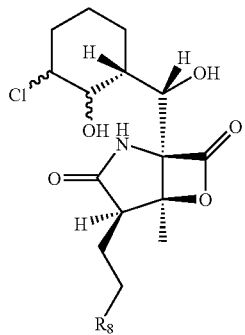

Additional exemplary structure and stereochemistry can be as follows:

IV-3C

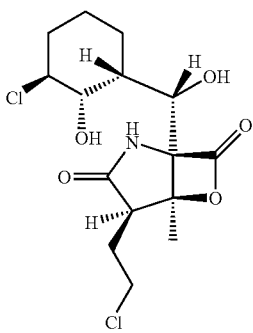

For example, an exemplary compound of Formula IV has the following structure IV-4:

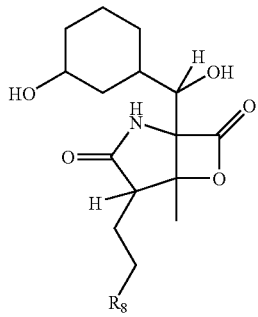

Formula IV-4

$R_8$ may include, for example, hydrogen, fluorine, chlorine, bromine and iodine.

Exemplary stereochemistry can be as follows:

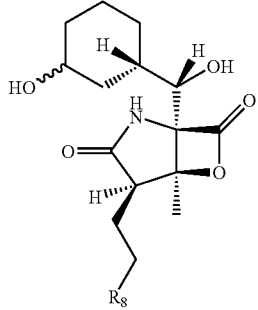

Compounds of Formula V

Some embodiments provide compounds, and methods of producing a class of compounds, pharmaceutically acceptable salts and pro-drug esters thereof, wherein the compounds are represented by Formula V:

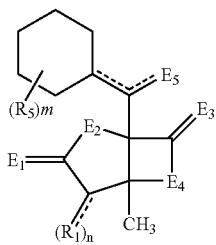

Formula V

In certain embodiments, the substituent(s) $R_1$ and $R_5$ may separately include a hydrogen, a halogen, a mono-substituted, a poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, amninocarbonyloxy, nitro, azido, phenyl, oxy, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl. In certain embodiments, each of $E_1$, $E_2$, $E_3$, $E_4$ and $E_5$ can be a heteroatom or substituted heteroatom, for example, nitrogen, sulfur or oxygen. Preferably, m may be, for example, 0, 1, 2, 3, 4, 5, 6, 7, 8, 9, 10, or 11 and if m is more than 1, then $R_5$ can be the same or different. Furthermore, the substituents $R_5$ may form a ring, for example, an epoxide. The dashed line indicates that the designated bond is either a single bond or a double bond.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred. In some embodiments, $R_1$ is not a substituted or unsubstituted, unbranched $C_6$ alkyl.

Compounds of Formula VI

Some embodiments provide compounds, and methods of producing a class of compounds, pharmaceutically acceptable salts and pro-drug esters thereof, wherein the compounds are represented by Formula VI:

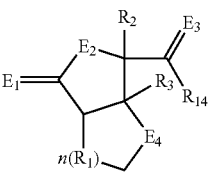

Formula VI wherein $R_1$ can be separately selected from the group consisting of a mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, phenyl, cycloalkylacyl, alkylthio, arylthio, oxysulfonyl, carboxy, thio, sulfoxide, sulfoneboronic acid esters, and halogenated alkyl including polyhalogenated alkyl. n is equal to 1 or 2, and if n is equal to 2, then $R_1$ can be the same or different;

wherein $R_2$, can be selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including, for example, cyclohexylcarbinol), cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl; wherein each of $E_1$, $E_2$, $E_3$ and $E_4$ can be a substituted or unsubstituted heteroatom.

In some embodiments, $R_2$ is not cyclohex-2-enyl carbinol when one of the $R_1$ substituents is ethyl or chloroethyl and $R_3$ is methyl.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred.

wherein $R_{14}$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, thioesters, sulfoxide, sulfone, sulfonate esters, thiocyano, and halogenated alkyl including polyhalogenated alkyl.

In some embodiments, preferably $R_{14}$ is an alkylthiol or substituted alkylthiol, and $E_3$ is an oxygen.

For example, in some embodiments some of the compounds of Formula VI can have the following structure referred to as Formula VI-1:

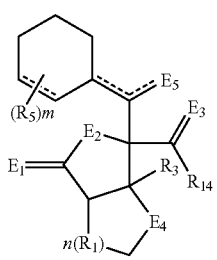

Formula VI-1 wherein $R_1$ can be separately selected from the group consisting of a mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, phenyl, cycloalkylacyl, alkylthio, arylthio, oxysulfonyl, carboxy, thio, sulfoxide, sulfone, boronic acid esters, and halogenated alkyl including polyhalogenated alkyl. n is equal to 1 or 2, and if n is equal to 2, then $R_1$ can be the same or different;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl; wherein each of $E_1$, $E_2$, $E_3$ and $E_4$ can be a substituted or unsubstituted heteroatom.

wherein $R_5$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl, wherein m is 0, 1, 2, 3, 4, 5, 6, 7, 8, 9, 10, or 11 and if m is more than 1, then $R_5$ can be the same or different; and where the substituents $R_5$ can form a ring; and wherein each of $E_1$, $E_2$, $E_3$, $E_4$ and $E_5$ is a substituted or unsubstituted heteroatom.

In some embodiments, preferably $R_1$ is a substituted or unsubstituted $C_1$ to $C_5$ alkyl. For example, methyl, ethyl, propyl, isopropyl, butyl, isobutyl, tert-butyl, and pentyl are preferred.

wherein $R_{14}$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, thioesters, sulfoxide, sulfone, sulfonate esters, thiocyano, and halogenated alkyl including polyhalogenated alkyl.

For example, the compound has the following structure VI-1A:

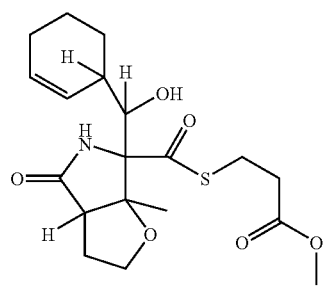

Formula VI-1A

Exemplary stereochemistry can be as follows:

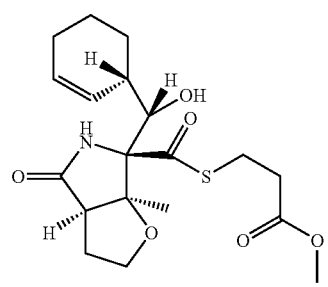

For example, an exemplary compound of Formula VI has the following structure and stereochemistry VI-1B:

Formula VI-1B

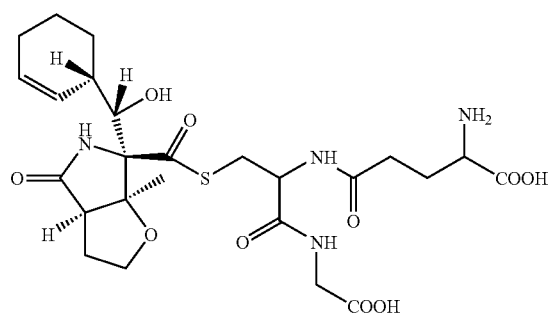

Another example, the compound of Formula VI has the following structure and stereochemistry VI-1C:

Formula VI-1C

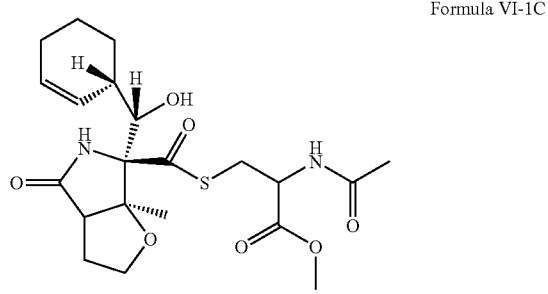

Certain embodiments also provide pharmaceutically acceptable salts and pro-drug esters of the compound of Formulae I-VI, and provide methods of obtaining and purifying such compounds by the methods disclosed herein.

The term "pro-drug ester," especially when referring to a pro-drug ester of the compound of Formula I synthesized by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester- or thioester-forming groups that are hydrolyzed under physiological conditions. Examples of pro-drug ester groups include pivoyloxymethyl, acetoxymethyl, phthalidyl, indanyl, and methoxymethyl, and thioester, as well as other such groups known in the art, including a (5-R-2-oxo-1,3-dioxolen-4-yl)methyl group. Other prodrugs can be prepared by preparing a corresponding thioester of the compound, for example, by reacting with an appropriate thiol, such as thiophenol, Cysteine or derivatives thereof, or propanethiol, for example. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is hereby incorporated by reference in its entirety.

The term "pro-drug ester," as used herein, also refers to a chemical derivative of the compound that is rapidly transformed in vivo to yield the compound, for example, by hydrolysis in blood.

The term "pharmaceutically acceptable salt," as used herein, and particularly when referring to a pharmaceutically acceptable salt of a compound, including Formulae I-VI, and Formula I-VI as produced and synthesized by the methods disclosed herein, refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$-$C_7$ alkylamine, cyclohexylamine, triethanolamine, ethylenediamine or tris-(hydroxymethyl)-aminomethane. With respect to compounds synthesized by the method of this embodiment that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions disclosed herein include pharmaceutically acceptable salts and pro-drug esters of the compound of Formulae I-VI obtained and purified by the methods disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

It will be also appreciated that the phrase "compounds and compositions comprising the compound," or any like phrase, is meant to encompass compounds in any suitable form for pharmaceutical delivery, as discussed in further detail herein. For example, in certain embodiments, the compounds or compositions comprising the same may include a pharmaceutically acceptable salt of the compound.

In one embodiment the compounds can be used to treat microbial diseases, cancer, and inflammation. Disease is meant to be construed broadly to cover infectious diseases, and also autoimmune diseases, non-infectious diseases and chronic conditions. In a preferred embodiment, the disease is caused by a microbe, such as a bacterium, a fungi, and protozoa, for example. The methods of use may also include the steps of administering a compound or composition comprising the compound to an individual with an infectious disease or cancer. The compound or composition can be administered in an amount effective to treat the particular infectious disease, cancer or inflammatory condition.

The infectious disease may be, for example, one caused by *Bacillus*, such as *B. anthracis* and *B. cereus*. The infectious disease can be one caused by a protozoa, for example, a *Leishmania*, a *Plasmodium* or a *Trypanosoma*. The compound or composition can be administered with a pharmaceutically acceptable carrier, diluent, excipient, and the like.

The cancer may be, for example, a multiple myeloma, a colorectal carcinoma, a prostate carcinoma, a breast adenocarcinoma, a non-small cell lung carcinoma, an ovarian carcinoma, a melanoma, and the like.

The inflammatory condition may be, for example, rheumatoid arthritis, asthma, multiple sclerosis, psoriasis, stroke, myocardial infarction, reperfusion injury, and the like.

The term "halogen atom," as used herein, means any one of the radio-stable atoms of column 7 of the Periodic Table of the Elements, i.e., fluorine, chlorine, bromine, or iodine, with bromine and chlorine being preferred.

The term "alkyl," as used herein, means any unbranched or branched, substituted or unsubstituted, saturated hydrocarbon, with $C_1$-$C_{24}$ preferred, and $C_1$-$C_6$ unbranched or branched, saturated or unsaturated, unsubstituted or substituted hydrocarbons being more preferred, and with methyl, ethyl, propyl, isopropyl, butyl, isobutyl, tert-butyl, and pentyl being most preferred. Among the substituted, saturated hydrocarbons, $C_1$-$C_{24}$ are preferred, with $C_1$-$C_6$ mono- and di- and per-halogen substituted saturated hydrocarbons and amino-substituted hydrocarbons most preferred.

The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Specifically, the definition of substituted is as broad as that provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. The other above-listed patents also provide standard definitions for the term "substituted" that are well-understood by those of skill in the art.

The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$-$C_6$ unbranched, mono-unsaturated and di-unsaturated, unsubstituted hydrocarbons being preferred, and mono-unsaturated, di-halogen substituted hydrocarbons being most preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom. The term "heterocycle" or "heterocyclic" refer to any cyclic compound containing one or more heteroatoms. The substituted aryls, heterocycles and heteroaryls can be substituted with any substituent, including those described above and those known in the art.

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring. The term "alkoxy carbonyl" refers to any linear, branched, cyclic, saturated, unsaturated, aliphatic or aromatic alkoxy attached to a carbonyl group. The examples include methoxycarbonyl group, ethoxycarbonyl group, propyloxycarbonyl group, isopropyloxycarbonyl group, butoxycarbonyl group, sec-butoxycarbonyl group, tert-butoxycarbonyl group, cyclopentyloxycarbonyl group, cyclohexyloxycarbonyl group, benzyloxycarbonyl group, allyloxycarbonyl group, phenyloxycarbonyl group, pyridyloxycarbonyl group, and the like.

The terms "pure, "purified," "substantially purified," and "isolated" as used herein refer to the compound of the embodiment being free of other, dissimilar compounds with which the compound, if found in its natural state, would be associated in its natural state. In certain embodiments described as "pure," "purified," "substantially purified," or "isolated" herein, the compound may comprise at least 0.5%, 1%, 5%, 10%, or 20%, and most preferably at least 50% or 75% of the mass, by weight, of a given sample.

The terms "derivative," "variant," or other similar term refers to a compound that is an analog of the other compound.

Certain of the compounds of Formula I-VI can be obtained and purified or can be obtained via semi-synthesis from purified compounds as set forth herein. Generally, without being limited thereto, the starting compounds, such as Compounds II-16, II-17 and II-18), below, can be obtained and the various analogs can be synthesized therefrom. Exemplary non-limiting syntheses are provided herein.

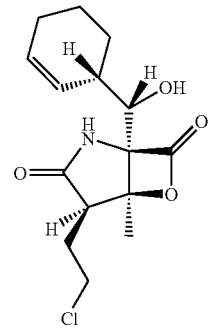

II-16

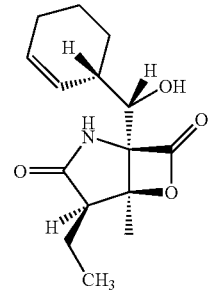

II-17

-continued

II-18

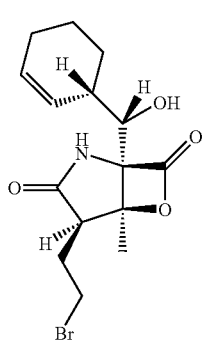

Production of Starting Compounds I-7, II-16, II-17 and II-18, II-20, II-24C, II-26, II-27 and II-28

The production of starting compounds I-7, II-16, II-17, II-18, II-20, II-24C, II-26, II-27 and II-28 can be carried out by cultivating strain CNB476 and strain NPS21184, a natural variant of strain CNB476, in a suitable nutrient medium under conditions described herein, preferably under submerged aerobic conditions, until a substantial amount of compounds are detected in the fermentation; harvesting by extracting the active components from the fermentation broth with a suitable solvent; concentrating the solvent containing the desired components; then subjecting the concentrated material to chromatographic separation to isolate the compounds from other metabolites also present in the cultivation medium.

The culture (CNB476) was deposited on Jun. 20, 2003 with the American Type Culture Collection (ATCC) in Rockville, Md. and assigned the ATCC patent deposition number PTA-5275. Strain NPS21184, a natural variant of strain CNB476, was derived from strain CNB476 as a single colony isolate. Strain NPS21184 has been deposited to ATCC on Apr. 27, 2005. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce the starting compounds I-7, II-16, II-17, II-18, II-20, II-24C, II-26 and II-28.

Fermentation of Strain CNB476 and Strain NPS21184

Production of compounds can be achieved at temperature conducive to satisfactory growth of the producing organism, e.g. from 16 degree C. to 40 degree C., but it is preferable to conduct the fermentation at 22 degree C. to 32 degree C. The aqueous medium can be incubated for a period of time necessary to complete the production of compounds as monitored by high pressure liquid chromatography (HPLC), preferably for a period of about 2 to 10 days, on a rotary shaker operating at about 50 rpm to 400 rpm, preferably at 150 rpm to 250 rpm, for example. The production of the compounds can also be achieved by cultivating the production strain in a bioreactor, such as a fermentor system that is suitable for the growth of the production strain.

Growth of the microorganisms can be achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources can be combined in the same medium, for example. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cottonseed meal, fish meal, peptone, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Pharmaceutical Compositions

In one embodiment, the compounds disclosed herein are used in pharmaceutical compositions. The compounds optionally and preferably are produced by the methods disclosed herein. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents can be provided in the pharmaceutical composition. For example, sodium benzoate, ascorbic acid and esters of p-hydroxybenzoic acid can be added as preservatives. In addition, antioxidants and suspending agents can be used.

The compositions, particularly those of Formulae I-VI, can be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate. Dragee cores are provided with suitable coatings. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. For this purpose, concentrated sugar solutions can be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties.

Further disclosed herein are various pharmaceutical compositions well known in the pharmaceutical art for uses that include topical, intraocular, intranasal, and intraauricular delivery. Pharmaceutical formulations include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A. 1994 *J Ocul Pharmacol* 10:29-45), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences (Mack Publishing, 18$^{th}$ Edition), which is incorporated herein by reference in its entirety, and well-known to those skilled in the art, suitable formulations are most often and preferably isotonic, slightly buffered to maintain a pH of 5.5 to 6.5, and most often and preferably include anti-microbial preservatives and appropriate drug stabilizers. Pharmaceutical formulations for intraauricular delivery include suspensions and ointments for topical application in the ear. Common solvents for such aural formulations include glycerin and water.

When used as an anti-cancer, anti-inflammatory or anti-microbial compound, for example, the compounds of Formulae I-VI or compositions including Formulae I-VI can be administered by either oral or non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, or the like.

In one embodiment, the anti-cancer, anti-inflammatory or anti-microbial can be mixed with additional substances to enhance their effectiveness. In one embodiment, the anti-microbial is combined with an additional anti-microbial. In another embodiment, the anti-microbial is combined with a drug or medicament that is helpful to a patient that is taking anti-microbials.

The compounds can be administered or used in combination with treatments such as chemotherapy, radiation, and biologic therapies. In some embodiments the compounds can be administered or used with a chemotherapeutic agent. Examples of such chemotherapeutics include Alkaloids, alkylating agents, antibiotics, antimetabolites, enzymes, hormones, platinum compounds, immunotherapeutics (antibodies, T-cells, epitopes), biological response modifiers (BRMs), and the like. Examples include, Vincristine, Vinblastine, Vindesine, Paclitaxel (Taxol), Docetaxel, topoisomerase inhibitors epipodophyllotoxins (Etoposide (VP-16), Teniposide (VM-26)), Camptothecin, nitrogen mustards (cyclophosphamide), Nitrosoureas, Carmustine, lomustine, dacarbazine, hydroxymethylmelamine, thiotepa and mitocycin C, Dactinomycin (Actinomycin D), anthracycline antibiotics (Daunorubicin, Daunomycin, Cerubidine), Doxorubicin (Adriamycin), Idarubicin (Idamycin), Anthracenediones (Mitoxantrone), Bleomycin (Blenoxane), Plicamycin (Mithramycin, Antifolates (Methotrexate (Folex, Mexate)), purine antimetabolites (6-mercaptopurine (6-MP, Purinethol) and 6-thioguanine (6-TG). The two major anticancer drugs in this category are 6-mercaptopurine and 6-thioguanine, Chlorodeoxyadenosine and Pentostatin, Pentostatin (2'-deoxycoformycin), pyrimidine antagonists, fluoropyrimidines (5-fluorouracil(Adrucil), 5-fluorodeoxyuridine (FdUrd) (Floxuridine)), Cytosine Arabinoside (Cytosar, ara-C), Fludarabine, L-ASPARAGINASE, Hydroxyurea, glucocorticoids, antiestrogens, tamoxifen, nonsteroidal antiandrogens, flutamide, aromatase inhibitors Anastrozole(Arimidex), Cisplatin, 6-Mercaptopurine and Thioguanine, Methotrexate, Cytoxan, Cytarabine, L-Asparaginase, Steroids: Prednisone and Dexamethasone. Also, proteasome inhibitors such as bortezomib can be used in combination with the instant compounds, for example. Examples of biologics can include agents such as TRAIL antibodies to TRAIL, integrins such as alpha-V-beta-3 ($\alpha$V$\beta$3) and/or other cytokine/growth factors that are involved in angiogenesis, VEGF, EGF, FGF and PDGF. In some aspects, the compounds can be conjugated to or delivered with an antibody. The above-described combination methods can be used to treat a variety of conditions, including cancer and neoplastic diseases, inflammation, and microbial infections.

Methods of Administration

In an alternative embodiment, the disclosed chemical compounds and the disclosed pharmaceutical compositions are administered by a particular method as an anti-microbial. Such methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the present embodiment into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the compositions that include the described compounds, including those of Formulae I-VI, required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the embodiment, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages can be between about 10 microgram/kg and 100 mg/kg body weight, preferably between about 100 microgram/kg and 10 mg/kg body weight. Alternatively dosages can be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above can be used in veterinary medicine.

Depending on the specific conditions being treated, such agents can be formulated and administered systemically or locally. A variety of techniques for formulation and administration can be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the embodiment can be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the embodiment into dosages suitable for systemic administration is within the scope of the embodiment. With proper choice of carrier and suitable manufacturing practice, the compositions disclosed herein, in particular, those formulated as solutions, can be administered parenterally, such as by intravenous injection. The compounds can be formulated readily using pharmaceutically acceptable carriers well known in the art into dosages suitable for oral administration. Such carriers enable the compounds of the embodiment to be formulated as tablets, pills, capsules, liquids, gels, syrups, slurries, suspensions and the like, for oral ingestion by a patient to be treated.

Agents intended to be administered intracellularly can be administered using techniques well known to those of ordinary skill in the art. For example, such agents can be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules can be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration can be in the form of tablets, dragees, capsules, or solutions. The pharmaceutical compositions can be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, can be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, can be determined using known methods. The efficacy of a particular compound can be established using several art recognized methods, such as in vitro methods, animal models, or human clinical trials. Art-recognized in vitro models exist for nearly every class of condition, including the conditions abated by the compounds disclosed herein, including cancer, cardiovascular disease, and various immune dysfinction, and infectious diseases. Similarly, acceptable animal models can be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an anti-microbial, anti-cancer, or anti-inflammatory agent, the compounds disclosed herein can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, intradermally, or the like. Controlled release formulations, depot formulations, and infusion pump delivery are similarly contemplated.

The compositions disclosed herein in pharmaceutical compositions may also comprise a pharmaceutically acceptable carrier. Such compositions can be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions can be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), can be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the embodiment, as described above, can be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions can be formulated and administered either systemically or locally. A variety of techniques for formulation and administration can be found in Remington's Pharmaceutical Sciences, 18th ed., Mack Publishing Co., Easton, Pa. (1990).

To formulate the compounds of Formulae I-VI as an anti-microbial, an anti-cancer, or an anti-inflammatory agent, known surface active agents, excipients, smoothing agents, suspension agents and pharmaceutically acceptable film-forming substances and coating assistants, and the like can be used. Preferably alcohols, esters, sulfated aliphatic alcohols, and the like can be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like can be used as excipients; magnesium stearate, talc, hardened oil and the like can be used as smoothing agents; coconut oil, olive oil, sesame oil, peanut oil, soya can be used as suspension agents or lubricants; cellulose acetate phthalate as a derivative of a carbohydrate such as cellulose or sugar, or methylacetate-methacrylate copolymer as a derivative of polyvinyl can be used as suspension agents; and plasticizers such as ester phthalates and the like can be used as suspension agents. In addition to the foregoing preferred ingredients, sweeteners, fragrances, colorants, preservatives and the like can be added to the administered formulation of the compound produced by the method of the embodiment, particularly when the compound is to be administered orally.

The compounds and compositions can be orally or non-orally administered to a human patient in the amount of about 0.001 mg/kg/day to about 10,000 mg/kg/day of the active ingredient, and more preferably about 0.1 mg/kg/day to about 100 mg/kg/day of the active ingredient at, preferably, one time per day or, less preferably, over two to about ten times per day. Alternatively and also preferably, the compound produced by the method of the embodiment may preferably be administered in the stated amounts continuously by, for example, an intravenous drip. Thus, for the example of a patient weighing 70 kilograms, the preferred daily dose of the active or anti-infective ingredient would be about 0.07 mg/day to about 700 gm/day, and more preferable, 7 mg/day to about 7 grams/day. Nonetheless, as will be understood by those of skill in the art, in certain situations it can be necessary to administer the anti-cancer, anti-inflammatory or the anti-infective compound of the embodiment in amounts that excess, or even far exceed, the above-stated, preferred dosage range to effectively and aggressively treat particularly advanced cancers or infections.

In the case of using the anti-cancer, anti-inflammatory, or anti-microbial produced by methods of the embodiment as a biochemical test reagent, the compound produced by methods of the embodiment inhibits the progression of the disease when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the embodiment for use as an anti-microbial, anticancer or anti-tumor compound is generally in the range of about 1 to about 100 µg/ml, the most appropriate use amount varies depending on the type of cultured cell system and the purpose of use, as will be appreciated by persons of ordinary skill in the art. Also, in certain applications it can be necessary or preferred to persons of ordinary skill in the art to use an amount outside the foregoing range.

In one embodiment, the method of using a compound as an anti-microbial, anti-cancer or anti-inflammatory involves administering an effective amount of any of the compounds of Formulae I-VI or compositions of those compounds. In a preferred embodiment, the method involves administering the compound represented by Formula II, to a patient in need of an anti-microbial, until the need is effectively reduced or more preferably removed.

As will be understood by one of skill in the art, "need" is not an absolute term and merely implies that the patient can benefit from the treatment of the anti-microbial, the anti-cancer, or anti-inflammatory in use. By "patient" what is meant is an organism that can benefit by the use of an anti-microbial, anti-cancer or anti-inflammatory agent. For example, any organism with *B. anthracis, Plasmodium, Leishmania, Trypanosoma*, and the like, may benefit from the application of an anti-microbial that may in turn reduce the amount of microbes present in the patient. As another example, any organism with cancer, such as, a colorectal carcinoma, a prostate carcinoma, a breast adenocarcinoma, a non-small cell lung carcinoma, an ovarian carcinoma, multiple myelomas, a melanoma, and the like, may benefit from the application of an anti-cancer agent that may in turn reduce the amount of cancer present in the patient. Furthermore, any organism with an inflammatory conditions, such as, rheumatoid arthritis, asthma, multiple sclerosis, psoriasis, stroke, reperfusion injury, myocardial infarction, and the like, may benefit from the application of an anti-inflammatory that may in turn reduce the amount of cells associated with the inflammatory response present in the patient. In one embodiment, the patient's health may not require that an anti-microbial, anti-cancer, or anti-inflammatory be administered, however, the patient may still obtain some benefit by the reduction of the level of microbes, cancer cells, or inflammatory cells present in the patient, and thus be in need. In one embodiment, the anti-microbial or anti-cancer agent is effective against one type of microbe or cancer, but not against other types; thus, allowing a high degree of selectivity in the treatment of the patient. In other embodiments, the anti-inflammatory can be effective against inflammatory conditions characterized by different cells associated with the inflammation. In choosing such an anti-microbial, anti-cancer or anti-inflammatory agent, the methods and results disclosed in the Examples can be useful. In an alternative embodiment, the anti-microbial can be effective against a broad spectrum of microbes, preferably a broad spectrum of foreign, and, more preferably, harmful bacteria, to the host organism. In embodiments, the anti-cancer and/or anti-inflammatory agent can be effective against a broad spectrum of cancers and inflammatory conditions/cells/substances. In yet another embodiment, the anti-microbial is effective against all microbes, even those native to the host. Examples of microbes that can be targets of anti-microbials, include, but are not limited to, *B. anthracis, Plasmodium, Leishmania, Trypanosoma*, and the like. In still further embodiments, the anti-cancer agent is effective against a broad spectrum of cancers or all cancers. Examples of cancers, against which the compounds can be effective include a colorectal carcinoma, a prostate carcinoma, a breast adenocarcinoma, a non-small cell lung carcinoma, an ovarian carcinoma, multiple myelomas, a melanoma, and the like. Exemplary inflammatory conditions against which the agents are effective include rheumatoid arthritis, asthma, multiple sclerosis, psoriasis, stroke, myocardial infarction, and the like.

"Therapeutically effective amount," "pharmaceutically effective amount," or similar term, means that amount of drug or pharmaceutical agent that will result in a biological or medical response of a cell, tissue, system, animal, or human that is being sought. In a preferred embodiment, the medical response is one sought by a researcher, veterinarian, medical doctor, or other clinician.

"Anti-microbial" refers to a compound that reduces the likelihood of survival of microbes, or blocks or alleviates the deleterious effects of a microbe. In one embodiment, the likelihood of survival is determined as a function of an individual microbe; thus, the anti-microbial will increase the chance that an individual microbe will die. In one embodiment, the likelihood of survival is determined as a function of a population of microbes; thus, the anti-microbial will increase the chances that there will be a decrease in the population of microbes. In one embodiment, anti-microbial means antibiotic or other similar term. Such anti-microbials are capable of blocking the harmful effects, destroying or suppressing the growth or reproduction of microorganisms, such as bacteria. For example, such antibacterials and other anti-microbials are described in Antibiotics, Chemotherapeutics and Antibacterial Agents for Disease Control (M. Grayson, editor, 1982), and E. Gale et al., The Molecular Basis of Antibiotic Action 2d edition (1981). In another embodiment, an anti-microbial will not change the likelihood of survival, but will change the chances that the microbes will be harmful to the host in some way. For instance, if the microbe secretes a substance that is harmful to the host, the anti-microbial may act upon the microbe to stop the secretion or may counteract or block the harmful effect. In one embodiment, an anti-microbial, while, increasing the likelihood that the microbe(s) will die, is minimally harmful to the surrounding, non-microbial, cells. In an alternative embodiment, it is not important how harmful the anti-microbial is to surrounding, nonmicrobial, cells, as long as it reduces the likelihood of survival of the microbe.

"Anti-cancer agent" refers to a compound or composition including the compound that reduces the likelihood of survival of a cancer cell. In one embodiment, the likelihood of survival is determined as a function of an individual cancer cell; thus, the anti-cancer agent will increase the chance that an individual cancer cell will die. In one embodiment, the likelihood of survival is determined as a function of a population of cancer cells; thus, the anti-cancer agent will increase the chances that there will be a decrease in the population of cancer cells. In one embodiment, anti-cancer agent means chemotherapeutic agent or other similar term.

A "chemotherapeutic agent" is a chemical compound useful in the treatment of a neoplastic disease, such as cancer. Examples of chemotherapeutic agents include alkylating agents, such as a nitrogen mustard, an ethyleneimine and a methylmelamine, an alkyl sulfonate, a nitrosourea, and a triazene, folic acid antagonists, anti-metabolites of nucleic acid metabolism, antibiotics, pyrimidine analogs, 5-fluorouracil, cisplatin, purine nucleosides, amines, amino acids, triazol nucleosides, corticosteroids, a natural product such as a vinca alkaloid, an epipodophyllotoxin, an antibiotic, an enzyme, a taxane, and a biological response modifier or antibodies to biological response modifiers or other agents; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gouadotropin-releasing hormone analog. Specific examples include Adriamycin, Doxorubicin, 5-Fluorouracil, Cytosine arabinoside ("Ara-C"), Cyclophosphamide, Thiotepa, Busulfan, Cytoxin, Taxol, Toxotere, Methotrexate, Cisplatin, Melphalan, Vinblastine, Bleomycin, Etoposide, Ifosfamide, Mitomycin C, Mitoxantrone, Vincristine, Vinorelbine, Carboplatin, Teniposide, Daunomycin, Carminomycin, Aminopterin, Dactinomycin, Mitomycins, Esperamicins, Melphalan, and other related nitrogen mustards. Also included in this definition are hormonal agents that act to regulate or inhibit hormone action on tumors, such as tamoxifen and onapristone.

The anti-cancer agent may act directly upon a cancer cell to kill the cell, induce death of the cell, to prevent division of the cell, and the like. Alternatively, the anti-cancer agent may indirectly act upon the cancer cell by limiting nutrient or blood supply to the cell, for example. Such anti-cancer agents are capable of destroying or suppressing the growth or reproduction of cancer cells, such as a colorectal carcinoma, a prostate carcinoma, a breast adenocarcinoma, a non-small cell lung carcinoma, an ovarian carcinoma, multiple myelomas, a melanoma, and the like.

A "neoplastic disease" or a "neoplasm" refers to a cell or a population of cells, including a tumor or tissue (including cell suspensions such as bone marrow and fluids such as blood or serum), that exhibits abnormal growth by cellular proliferation greater than normal tissue. Neoplasms can be benign or malignant.

An "inflammatory condition" includes, for example, conditions such as ischemia, septic shock, autoimmune diseases, rheumatoid arthritis, inflammatory bowel disease, systemic lupus eythematosus, multiple sclerosis, asthma, osteoarthritis, osteoporosis, fibrotic diseases, dermatosis, including psoriasis, atopic dermatitis and ultraviolet radiation (UV)-induced skin damage, psoriatic arthritis, alkylosing spondylitis, tissue and organ rejection, Alzheimer's disease, stroke, atherosclerosis, restenosis, diabetes, glomerulonephritis, cancer, Hodgkins disease, cachexia, inflammation associated with infection and certain viral infections, including acquired immune deficiency syndrome (AIDS), adult respiratory distress syndrome and Ataxia Telangiestasia.

In one embodiment, a described compound, preferably a compound having the Formulae I-VI, including those as described herein, is considered an effective anti-microbial, anti-cancer, or anti-inflammatory if the compound can influence 10% of the microbes, cancer cells, or inflammatory cells, for example. In a more preferred embodiment, the compound is effective if it can influence 10 to 50% of the microbes, cancer cells, or inflammatory cells. In an even more preferred embodiment, the compound is effective if it can influence 50-80% of the microbes, cancer cells, or inflammatory cells. In an even more preferred embodiment, the compound is effective if it can influence 80-95% of the microbes, cancer cells, or inflammatory cells. In an even more preferred embodiment, the compound is effective if it can influence 95-99% of the microbes, cancer cells, or inflammatory cells. "Influence" is defined by the mechanism of action for each compound. Thus, for example, if a compound prevents the reproduction of microbes, then influence is a measure of prevention of reproduction. Likewise, if a compound destroys microbes, then influence is a measure of microbe death. Also, for example, if a compound prevents the division of cancer cells, then influence is a measure of prevention of cancer cell division. Further, for example, if a compound prevents the proliferation of inflammatory cells, then influence is a measure of prevention of inflammatory cell proliferation. Not all mechanisms of action need be at the same percentage of effectiveness. In an alternative embodiment, a low percentage effectiveness can be desirable if the lower degree of effectiveness is offset by other factors, such as the specificity of the compound, for example. Thus a compound that is only 10% effective, for example, but displays little in the way of harmful side-effects to the host, or non-harmful microbes or cells, can still be considered effective.

In one embodiment, the compounds described herein are administered simply to remove microbes, cancer cells or inflammatory cells, and need not be administered to a patient. For example, in situations where microbes can present a problem, such as in food products, the compounds described herein can be administered directly to the products to reduce the risk of microbes in the products. Alternatively, the compounds can be used to reduce the level of microbes present in the surrounding environment, such working surfaces. As another example, the compounds can be administered ex vivo to a cell sample, such as a bone marrow or stem cell transplant to ensure that only non-cancerous cells are introduced into the recipient. After the compounds are administered they may optionally be removed. This can be particularly desirable in situations where work surfaces or food products may come into contact with other surfaces or organisms that could risk being harmed by the compounds. In an alternative embodiment, the compounds can be left in the food products or on the work surfaces to allow for a more protection. Whether or not this is an option will depend upon the relative needs of the situation and the risks associated with the compound, which in part can be determined as described in the Examples below.

The following non-limiting examples are meant to describe the preferred embodiments of the methods. Variations in the details of the particular methods employed and in the precise chemical compositions obtained will undoubtedly be appreciated by those of skill in the art.

EXAMPLES

Example 1

Fermentation of Starting Compound II-16 and Compounds of Formulae I-7, II-17, II-20, and II-24C, II-26 and II-28 using Strain CNB476

Strain CNB476 was grown in a 500-ml flask containing 100 ml of vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml each of the first seed culture was inoculated into three 500-ml flasks containing of 100 ml of the vegetative medium. The second seed cultures were incubated at 28 degree C. and 250 rpm on a rotary shaker for 2 days. Five ml each of the second seed culture was inoculated into thirty-five 500-ml flasks containing of 100 ml of the vegetative medium. The third seed cultures were incubated at 28 degree and 250 rpm on a rotary shaker for 2 days. Five ml each of the third seed culture was inoculated into four hundred 500-ml flasks containing 100 ml of the Production Medium A consisting of the following per liter of deionized water: starch, 10 g; yeast extract, 4 g; Hy-Soy, 4 g; ferric sulfate, 40 mg; potassium bromide, 100 mg; calcium carbonate, 1 g; and synthetic sea salt (Instant Ocean, Aquarium Systems), 30 g. The production cultures were incubated at 28 degree C. and 250 rpm on rotary shakers for 1 day. Approximately 2 to 3 grams of sterile Amberlite XAD-7 resin were added to the production cultures. The production cultures were further incubated at 28 degree C. and 250 rpm on rotary shakers for 5 days and achieved a titer of Compound II-16 about 200 mg/L. The culture broth was filtered through cheese cloth to recover the Amberlite XAD-7 resin. The resin was extracted with 2 times 6 liters ethyl acetate followed by 1 time 1.5 liters ethyl acetate. The combined extracts were dried in vacuo. The dried extract was then processed for the recovery of Compound II-16 and the compounds of Formulae I-7, II-20, II-24C, II-26 and II-28.

Example 2

Fermentation of Starting Compound II-16 and Compounds of Formulae I-7, II-17, II-20, II-24C, II-26 and II-28 using Strain NPS21184

Strain NPS21184 was grown in a 500-ml flask containing 100 ml of vegetative medium consisting of the following per liter of deionized water: glucose, 8 g; yeast extract, 6 g; Hy-Soy, 6 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into 500-ml flask containing of 100 ml of the vegetative medium. The second seed cultures were incubated at 28 degree C. and 250 rpm on a rotary shaker for 2 days. Five ml each of the second seed culture was inoculated into 500-ml flask containing of 100 ml of the vegetative medium. The third seed cultures were incubated at 28 degree and 250 rpm on a rotary shaker for 2 days. Five ml each of the third seed culture was inoculated into 500-ml flask containing 100 ml of the Production Medium B consisting of the following per liter of deionized water: starch, 20 g; yeast extract, 4 g; Hy-Soy, 8 g; ferric sulfate, 40 mg; potassium bromide, 100 mg; calcium carbonate, 1 g; and synthetic sea salt (Instant Ocean, Aquarium Systems), 30 g. The production cultures were incubated at 28 degree C. and 250 rpm on rotary shakers for 1 day. Approximately 2 to 3 grams of sterile Amberlite XAD-7 resin were added to the production culture. The production culture was further incubated at 28 degree C. and 250 rpm on rotary shaker for 4 days and achieved a titer of 350-400 mg/L for Compound II-16.

Alternatively, the production of the compounds can be achieved in a 42L fermentor system using strain NPS21184. Strain NPS21184 was grown in a 500-ml flask containing 100 ml of vegetative medium consisting of the following per liter of deionized water: glucose, 8 g; yeast extract, 6 g; Hy-Soy, 6 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into 500-ml flask containing of 100 ml of the vegetative medium. The second seed cultures were incubated at 28 degree C. and 250 rpm on a rotary shaker for 2 days. Twenty ml each of the second seed culture was inoculated into 2.8L Fembach flask containing of 400 ml of the vegetative medium. The third seed cultures were incubated at 28 degree and 250 rpm on a rotary shaker for 2 days. 1.2L of the third seed culture was inoculated into a 42L fermentor containing 26L of Production Medium A. Production Medium B and Production Medium C, with the following composition, can also be used. Production Medium C consisting of the following per liter of deionized water: starch, 15 g; yeast extract 6 g; Hy-Soy, 6 g; ferric sulfate, 40 mg; potassium bromide, 100 mg; calcium carbonate, 1 g; and synthetic sea salt (Instant Ocean, Aquarium Systems), 30 g. The fermentor cultures were operated at the following parameters: temperature, 28 degree C.; agitation, 200 rpm; aeration, 13L/min and back pressure, 4.5 psi. At 36 to 44 hours of the production cycle, approximately 600 grams of sterile Amberlite XAD-7 resin were added to the fermentor culture. The production culture was further incubated at the above operating parameters until day 4 of the production cycle. The aeration rate was lowered to 8L/min. At day 5 of the production cycle, the fermentor culture achieved a titer of about 300 mg/L for Compound II-16. The culture broth was filtered through cheese cloth to recover the Amberlite XAD-7 resin. The resin was extracted with 2 times 4.5L liters ethyl acetate followed by 1 time 1.5 liters ethyl acetate. The combined extracts were dried in vacuo. The dried extract was then processed for the recovery of Compound II-16 and the compounds of Formulae I-7, II-17, II-20, II-24C, II-26 and II-28.

Example 3

Purification of Starting Compound II-16 and Compounds of Formulae II-20, II-24C, II-26 and II-28

3A: Purification of II-16, II-20, II-24C, II-26 and II-28

The pure Compound II-16 and compounds of Formulae I-20, II-24C, II-26 and II-28 were obtained by flash chromatography followed by HPLC. Eight grams crude extract containing 3.8 grams Compound II-16 and lesser quantities of II-20, II-24C, II-26 and II-28 was processed by flash chromatography using Biotage Flash40i system and Flash 40M cartridge (KP-Sil Silica, 32-63 µm, 90 grams). The flash chromatography was developed by the following step gradient:

1. Hexane (1L)
2. 10% Ethyl acetate in hexane (1L)
3. 20% Ethyl acetate in hexane, first elution (1L)
4. 20% Ethyl acetate in hexane, second elution (1L)
5. 20% Ethyl acetate in hexane, third elution (1L)
6. 25% Ethyl acetate in hexane (1L)
7. 50% Ethyl acetate in hexane (1L)
8. Ethyl acetate (1L)

Fractions containing Compound II-16 in greater or equal to 70% UV purity by HPLC were pooled and subject to HPLC purification, as described below, to obtain Compound II-16, along with II-20 and II-24C, each as pure compounds

| | |
|---|---|
| Column | Phenomenex Luna 10 u Silica |
| Dimensions | 25 cm × 21.2 mm ID |
| Flow rate | 25 ml/min |
| Detection | ELSD |
| Solvent | Gradient of 24% EtOAc/hexane for 19 min, 24% EtOAc/hexane to 100% EtOAc in 1 min, then 100% EtOAc for 4 min |

The fraction enriched in Compound II-16 (described above; ~70% pure with respect to Compound II-16) was dissolved in acetone (60 mg/ml). Aliquots (950 ul) of this solution were injected onto a normal-phase HPLC colunm using the conditions described above. Compound II-16 typically eluted after 14 minutes and compounds II-24C and II-26 co-eluted as a single peak at 11 min. When parent samples containing compounds II-17, II-20 and II-28 were processed, Compound II-17 eluted at 22 minutes, while II-20 and II-28 co-eluted at 23 minutes during the 100% ethyl acetate wash. Fractions containing Compound II-16 and minor analogs were pooled based on composition of compounds present, and evaporated under reduced pressure on a rotary evaporator. This process yielded pure Compound II-16, as well as separate fractions containing minor compounds II-20, II-24C, II-26 and II-28, which were further purified as described below.

Sample containing II-24C and II-26 generated from the process described above were further separated using reversed-phase preparative HPLC as follows. The sample (70 mg) was dissolved in acetonitrile at a concentration of 10 mg/ml, and 500 µl was loaded on an HPLC column of dimensions 21 mm i.d. by 15 cm length containing Eclipse XDB-C18 support. The solvent gradient increased linearly from 15% acetonitrile/85% water to 100% acetonitrile over 23 minutes at a flow rate of 14.5 ml/min. The solvent composition was held at 100% acetonitrile for 3 minutes before returning to the starting solvent mixture. Compound II-26 eluted at 17.5 minutes while compound II-24C eluted at 19 minutes under these conditions.

Crystalline II-26 was obtained using a vapor diffusion method. Compound II-26 (15 mg) was dissolved in 100 µl of acetone in a 1.5 ml v-bottom HPLC vial. This vial was then placed inside a larger tightly-stoppered vessel containing 1 ml of pentane. Crystals suitable for X-ray crystallography experiments were observed along the sides and bottom of the inner vial after 48 hours of incubation at 4° C. Crystallography data was collected on a Bruker SMART APEX CCD X-ray diffractometer (F(000)=2656, $Mo_{K\alpha}$ radiation, $\lambda$=0.71073 Å, µ=0.264 $mm^{-1}$, T=100K) at the UCSD Crystallography Facility and the refinement method used was full-matrix least-squares on $F^2$. Crystal data NPI-2065: $C_{15}H_{20}ClNO_4$, MW=313.77, tetragonal, space group P4(1)2(1)2, a=b=11.4901(3) Å, c=46.444(2) Å, α=β=γ=90°, vol=6131.6(3) $Å^3$, Z=16, $\rho_{calcd}$=1.360 g $cm^{-3}$, crystal size, 0.30×0.15×0.07 $mm^3$, θ range, 1.75-26.00°, 35367 reflections collected, 6025 independent reflections ($R_{int}$=0.0480), final R indices (I>2σ(I)): $R_1$=0.0369, $wR_2$=0.0794, GOF=1.060.

In order to separate II-28 from II-20, a reverse-phase isocratic method was employed. Sample (69.2 mg) containing both compounds was dissolved in acetonitrile to a concentration of 10 mg/ml, and 500 µl was loaded on a reverse-phase HPLC column (ACE 5µ C18-HL, 15 cm×21 mm ID) per injection. An isocratic solvent system of 27% acetonitrile/63% water at flow rate of 14.5 ml/min was used to separate compounds II-28 and II-20, which eluted after 14 and 16 minutes, respectively. Fractions containing compounds of interest were immediately evaporated under reduced pressure at room temperature on a rotary evaporator. Samples were then loaded onto a small column of silica and eluted with 10 ml of 70% hexane/30% acetone to remove additional impurities.

Samples generated from the preparative normal-phase HPLC method described above that contained II-20 but were free of II-28 could also be triturated with 100% EtOAc to remove minor lipophilic impurities.

Starting Compound II-16: UV (Acetonitrile/$H_2O$) $\lambda_{max}$ 225(sh) nm. Low Res. Mass: m/z 314 (M+H), 336 (M+Na).

Figure 16:
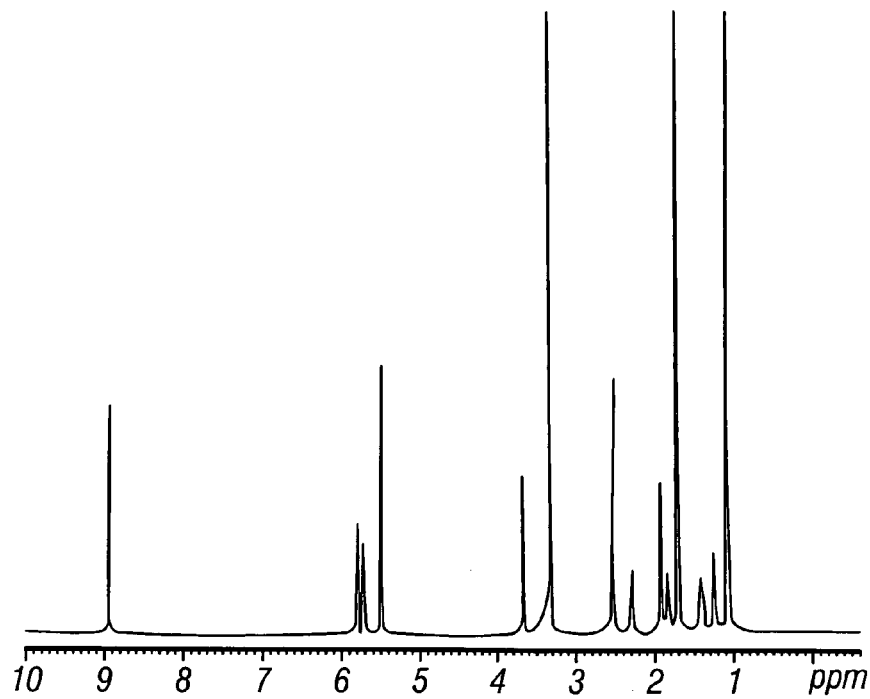
FIG. 16 depicts the $^1$H NMR spectrum of the compound of Formula II-20.

Compound of Formula II-20: UV (Acetonitrile/$H_2O$) $\lambda_{max}$ 225(sh) nm. Low Res. Mass: m/z 266 (M+H); HRMS (ESI), m/z 266.1396 (M+H), $\Delta_{calc}$=1.2 ppm. FIG. 16 depicts the 1H NMR spectrum of a compound having the structure of Formula II-20.

Compound of Formula II-24C: UV (Acetonitrile/$H_2O$) $\lambda_{max}$ 225(sh) nm.

Figure 19:
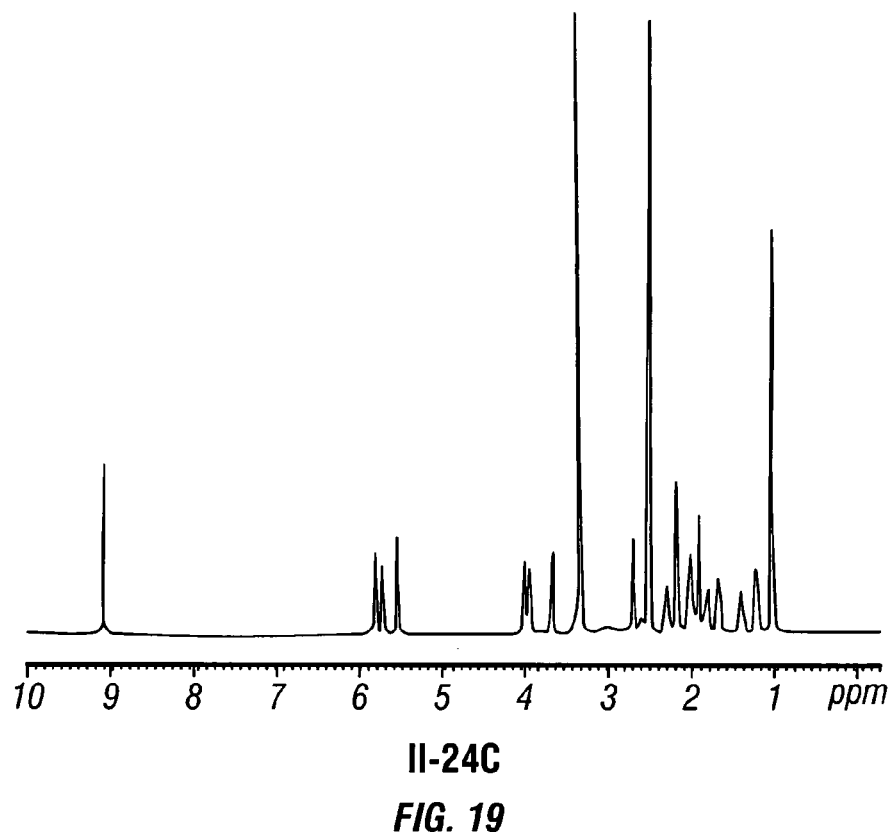
FIG. 19 depicts the $^1$H NMR spectrum of the compound of Formula II-24C.

Low Res. Mass: m/z 328 (M+H), 350 (M+Na); HRMS (ESI), m/z 328.1309 (M+H), $\Delta_{calc}$=-2.0 ppm, $C_{16}H_{23}NO_4Cl$. FIG. 19 depicts the 1H NMR spectrum of a compound having the structure of Formula II-24C.

Figure 23:
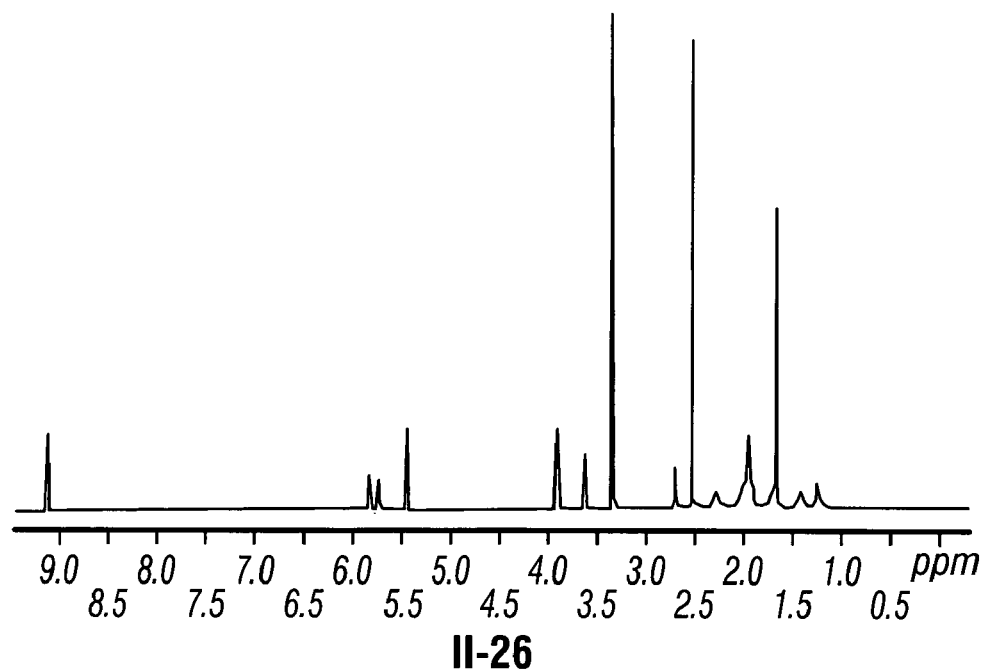
FIG. 23 depicts the $^1$H NMR spectrum of the compound of Formula II-26 in DMSO-$d_6$.

Compound of Formula II-26: UV (Acetonitrile/$H_2O$) $\lambda_{max}$ 225(sh) nm; HRMS (ESI), m/z 314.1158 (M+H), $\Delta_{calc}$=-0.4 ppm, $C_{15}H_{21}NO_4Cl$; FIG. 23 depicts the $^1$H NMR spectrum of a compound having the structure of Formula II-26 in DMSO-$d_6$).

Figure 26:
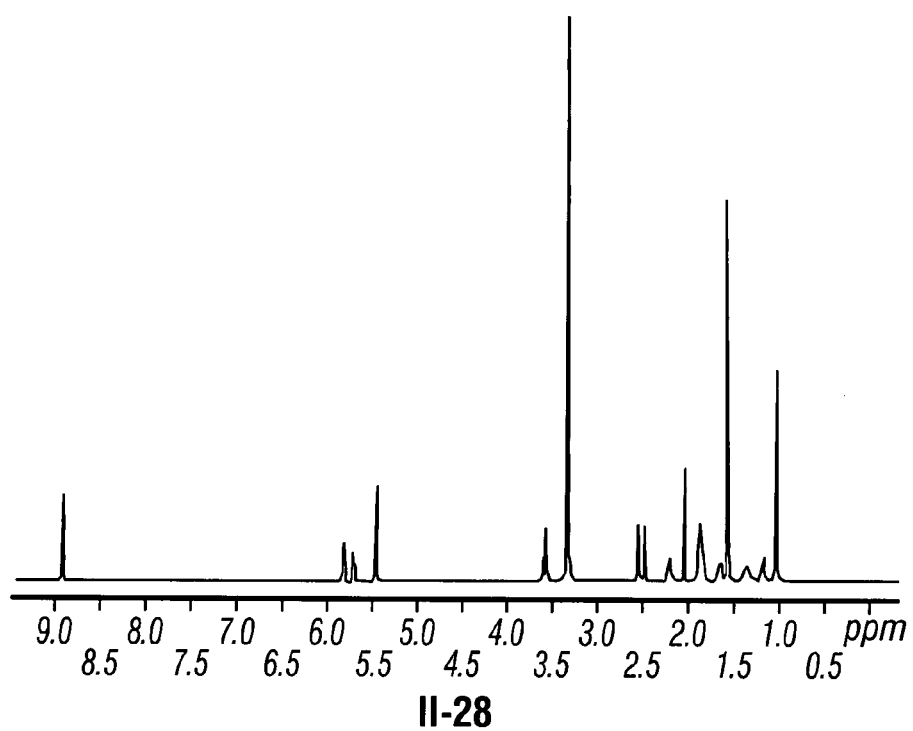
FIG. 26 depicts the $^1$H NMR spectrum of the compound of Formula II-28 in DMSO-$d_6$.

Compound of Formula II-28: UV (Acetonitrile/$H_2O$) $\lambda_{max}$ 225(sh) nm; HRMS (ESI), m/z 266.1388 (M+H), $\Delta_{calc}$=-1.8 ppm, $C_{14}H_{20}NO_4$. FIG. 26 depicts the $^1$H NMR spectrum of a compound having the structure of Formula II-28 in DMSO-$d_6$).

3B: Larze Scale Purification of Compound II-16

A two-step process was developed for the purification of Compound II-16 from crude extracts obtained from the culture broth of NPS21184 The first step of the process involves normal phase flash chromatography of the crude extract to produce material highly enriched in Compound II-16 (~95% purity). The enriched material is further purified by multiple crystallizations until no single impurity is present at ≧1.0% in the final colorless crystalline material of Compound II-16

Biotage Flash Chromatography (Purification Step 1)

The Biotage Flash 75Li system, including a Flash 75L KP-Sil cartridge, without SIM, was used for flash chromatography. Based on method development experiments, the loading capacity of the system was established to be 10 g of crude extract per 800 g of silica. Better resolution of Compound II-16 and Compound II-17 may be obtained by loading 8 g of crude extract on 800 g of silica; however, the recovery was comparable using either load.

Crude extract (10.0 g, dried by high vacuum) containing Compound II-16 (5.30 g; estimated from standard plot under HPLC) in a 250 ml Erlenmeyer flask was dissolved to a concentration of 107 mg/ml in acetone (93.5 ml) by sonicating the sample at 40° C. for about 6 minutes. The sample was filtered by gravity using fluted filter paper into another 250 ml Erlenmeyer flask, and the filter paper was washed with 5 ml of acetone. A 150 µl aliquot of this solution was transferred into a tared 1 dram vial for purity analysis and mass estimation of Compound II-16. The filtered crude extract was directly injected onto a new, dry Flash 75L KP-Sil cartridge using an open 60 ml syringe as a funnel and by transferring the sample from flask to syringe using a glass volumetric pipette. Due to the low viscosity of the sample, gravity was sufficient to load the sample onto the column; no additional pressure was required. Once the entire sample was absorbed onto the column, the flask was washed with 5 ml of acetone, and this solution was also loaded. Five minutes after loading the sample, the system was pressurized by house air, and then the following solvent step gradient was run through the column at approximately 15 psi and a flow rate between 235 ml/min and 250 ml/min:

1. 3 CV*10% EtOAc in n-Heptane
2. 15 CV*25% EtOAc in n-Heptane
3. 5 CV*30% EtOAc in n-Heptane

*For 75L cartridge, 1 CV=1070 ml

The eluent for the first step was collected as one fraction (~2500 ml), after which 500 ml fractions (0.47 column volume) were collected. In order to determine which fractions contained Compound II-16, fractions were analyzed by TLC. Each fraction was spotted onto a Si TLC plate, developed in 40% EtOAc/60% hexanes, and visualized using phosphomolybidic acid spray, then heat. A 1 ml aliquot was subsequently taken from each fraction containing Compound II-16, dried under a stream of nitrogen, redissolved in 0.5 ml of ACN and analyzed by LC-MS. While samples were being run on LC-MS, fractions were covered with aluminum foil and allowed to stand at room temperature.

The resulting chromatograms (UV@210 nm) were analyzed by only integrating Compound II-16, Compound II-26, and Compound II-17 peaks. Those fractions containing Compound II-16, as well as <10% Compound II-26 and <5% Compound II-17, were pooled and concentrated down to 4-6% (~600 mL) of the total pooled volumes using a Buchi R-220 Rotavapor with water bath temperature between 28° C. and 30° C. The yellow liquid in the flask was slowly siphoned out leaving behind the white solid. The white solid was dissolved in acetone and transferred to a 2 L round bottom flask and concentrated by a rotary evaporator at 30° C. and weighed. The dry aliquot was analyzed on LC-MS. The purity of the sample was greater than 95% (95.7%) and the major impurities were Compound II-26 (3.2%) and Compound II-17 (0.38%). The yield of Compound II-16 was 86% after this step, as calculated from the mass of Compound II-16 recovered from flash chromatography versus the mass of Compound II-16 estimated to be present in the crude extract. Samples containing Compound II-16 were stored at −20° C. without desiccation until further purification by crystallization.

When multiple Biotage runs are required to process quantities of crude extract that exceed the loading capacity of a single column, the above purification process should be completed for each individual Biotage run. Resulting material from each run may then be combined and crystallized using the steps described below, in order to yield one final lot of Compound II-16.

Crystallization-General Procedure (Purification Step-2):

The Compound II-16 samples obtained from Biotage flash chromatography typically contain about 3% of NPI-2065. The main aim of the crystallization step is to increase the purity of NPI-0052 to >97% and to reduce NPI-2065 to <1%.

Crystallizations were performed on Compound II-16 samples obtained from Biotage Runs by dissolving the solid (4.56 g) in 1:1 acetone:n-heptane (910 ml) to a final concentration of 5 g/L. The solvent was slowly evaporated under reduced pressure (about 275 mbar) using a rotary evaporator with vacuum controller (Buchi R-200 Rotavapor) and a water bath temperature of about 30° C. until the solvent was reduced to about 43% (±6%) of its original volume. During this evaporation process, crystals were formed around the flask walls as well as in the solution. The solution (supernatant) was removed by siphoning under house vacuum into a 500 ml Erlenmeyer flask, concentrated by rotary evaporation and transferred to a 20 ml scintillation vial by dissolving in acetone. The acetone was removed under a stream of $N_2$, and the solid was further dried by high vacuum before it was weighed. The mass of the material obtained from the supernatant was used to approximate the amount of crystalline material remaining. The crystals in the 2 L flask were dissolved in acetone (455 ml, the same volume of acetone used for initial crystallization). In order to determine the purity, an aliquot (100 µl) was removed, concentrated under a stream of $N_2$, redissolved in ACN to a final concentration of 1 mg/ml and analyzed by LC-MS. Analytical results showed a 31% reduction of Compound II-26. n-Heptane (455 ml; the same volume used for initial crystallization to make a 1:1 acetone: n-heptane solution) was added to the 2 L flask and the crystallization process was repeated. This process was reiterated until Compound II-26 was reduced to <1%; 3-4 crystallizations were needed to reach this target.

The final crystallization was performed in EtOAC/n-heptane solution. The crystalline material obtained above was redissolved in 1:1 EtOAc: n-heptane (same concentration as the first acetone: n-heptane crystallization, i.e. 5 g/L). The solvent was slowly evaporated under reduced pressure (about 130 mbar) using a rotary evaporator with a water bath temperature of 30° C. until the solvent was reduced to about 30% of its original volume. During this evaporation process, most of the crystals stayed suspended in solution and did not adhere strongly to the sides of the flask. The solution (supernatant) was removed by siphoning under house vacuum into a 500 ml Erlenmeyer flask, and then concentrated by rotary evaporation in a 250 ml round bottom flask, dried by high vacuum pump and weighed. The crystals in the 2 L flask were also dried by high vacuum for about 2 hrs, after which the white, crystalline material was removed from the flask. A few crystals were randomly selected from various places in the flask for purity analysis. The Compound II-26 was reduced from 0.98% to 0.66% (average of two data points) in this step.

The yield was about 87% (±2) from crude extract to Biotage chromatography and about 56% (±6) from Biotage to crystallization) based on two Biotage runs. The overall yield for these two crude extracts to final product was 43% and 54%. In addition compound II-16 was consistently obtained in >98% purity, with no single impurity ≧1%. Specifically, impurity Compound II-26 was reduced to 0.5% after four rounds of crystallization. Finally, the material obtained from the last crystallization step, performed in EtOAc:n-heptane, resulted in crystals that were easy to manage in the solid state and these crystals can be easily captured by filtration from the mother liquor.

3C: Purification of I-7

Supernatant material obtained from the crystallization step of the large scale purification of Compound II-16 described above was dissolved in acetone (80 mg/ml). Aliquots (500 ul) of this solution were injected onto a normal-phase HPLC column using the conditions described previously for normal phase purification of Compounds II-16, II-24C, II-26 and II-28. Compound of Formula I-7 eluted at 7.5 minutes as a pure compound.

Figure 30:
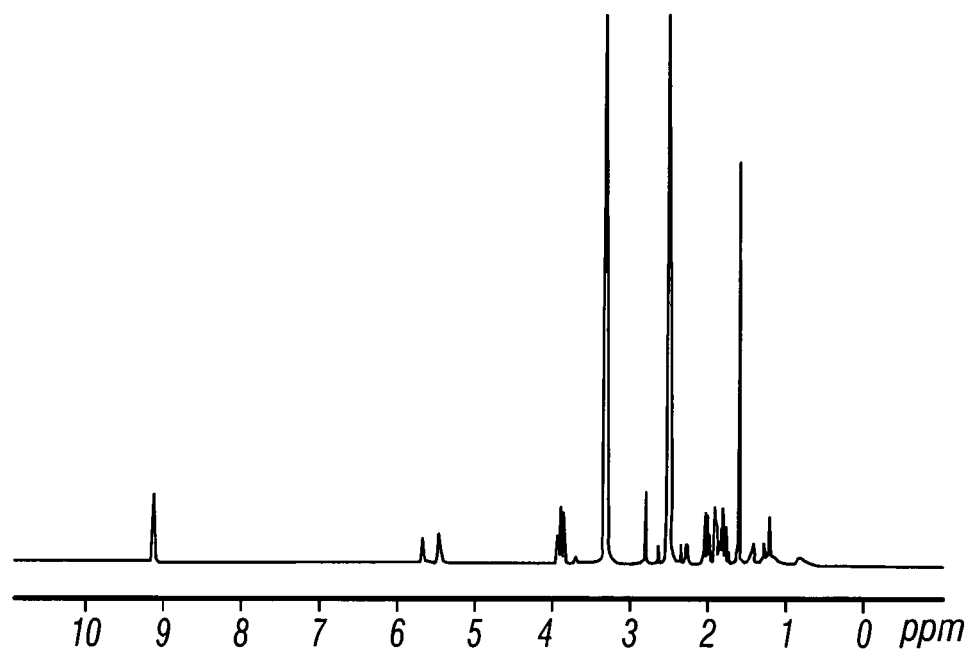
FIG. 30 depicts the $^1$H NMR spectrum of the compound of Formula I-7 in DMSO-$d_6$.
Figure 31:
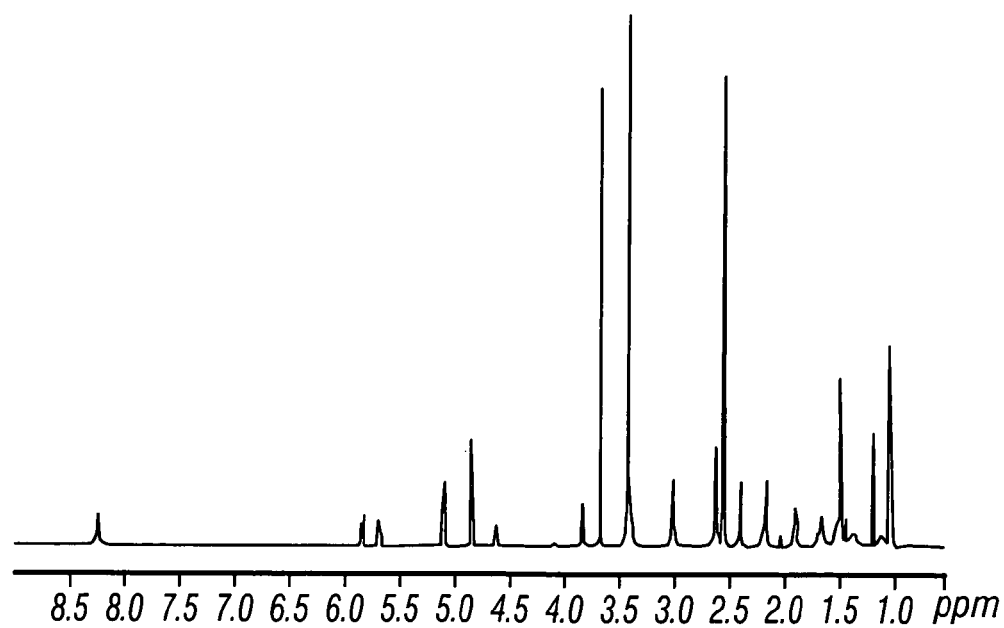
FIG. 31 depicts the $^1$H NMR spectrum of the compound of Formula II-47 in DMSO-$d_6$.
Figure 32:
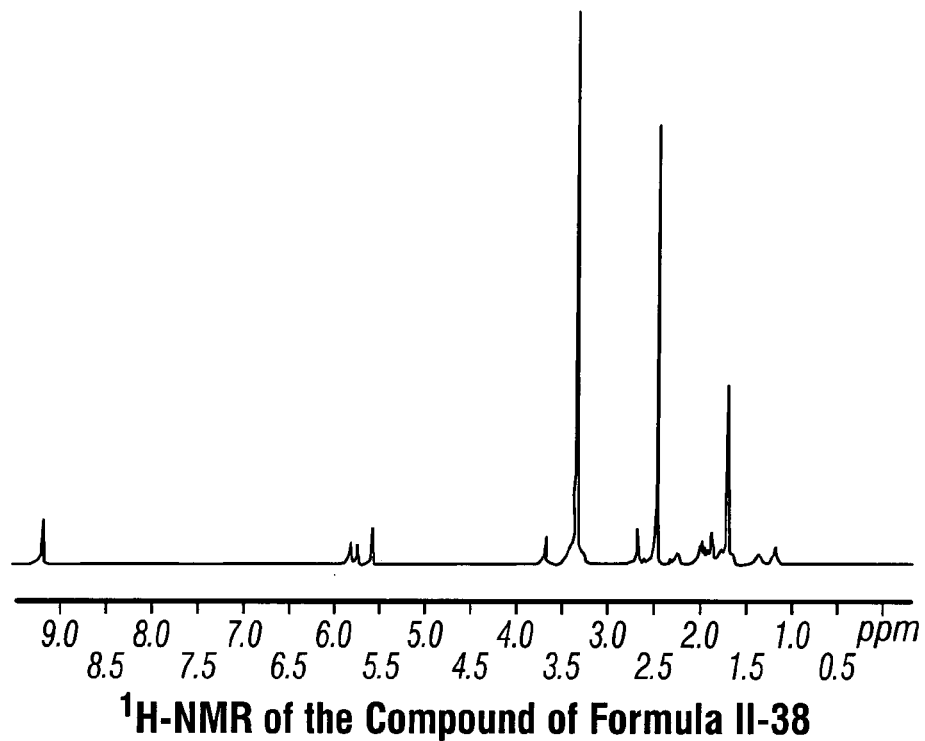
FIG. 32 depicts the $^1$H NMR spectrum of the compound of Formula II-38 in DMSO-$d_6$.
Figure 33:
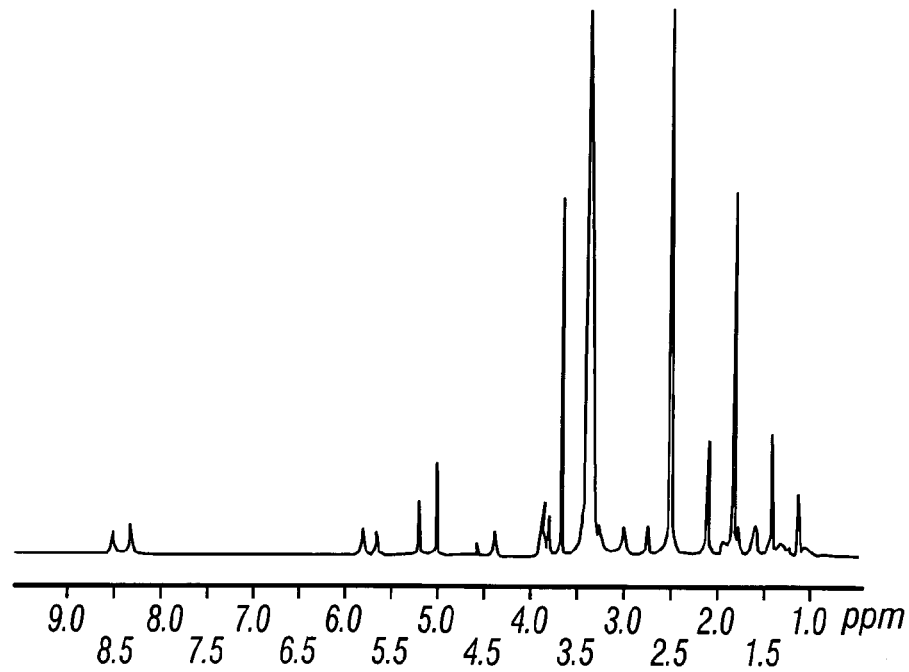
FIG. 33 depicts the $^1$H NMR spectrum of the compound of Formula II-50 in DMSO-$d_6$.

Compound of Formula I-7 (FIG. 30): UV (Acetonitrile/$H_2O$) $\lambda_{max}$ 225(sh) nm. Low Res. Mass: m/z 298 (M+H), 320 (M+Na).

Example 4

Fermentation of Starting Compounds I-17 and II-18 and Compound of Formula II-27

Strain CNB476 was grown in a 500-ml flask containing 100 ml of the first vegetative medium consisting of the following per liter of deionized water: glucose, 4 g; Bacto tryptone, 3 g; Bacto casitone, 5 g; and synthetic sea salt (Instant Ocean, Aquarium Systems), 30 g. The first seed culture was incubated at 28 degree C. for 3 days on a rotary shaker operating at 250 rpm. Five ml of the first seed culture was inoculated into a 500-ml flask containing 100 ml of the second vegetative medium consisting of the following per liter of deionized water: starch, 10 g; yeast extract, 4 g; peptone, 2 g; ferric sulfate, 40 mg; potassium bromide, 100 mg; calcium carbonate, 1 g; and sodium bromide, 30 g. The second seed cultures were incubated at 28 degree C. for 7 days on a rotary shaker operating at 250 rpm. Approximately 2 to 3 gram of sterile Amberlite XAD-7 resin were added to the second seed culture. The second seed culture was further incubated at 28 degree C. for 2 days on a rotary shaker operating at 250 rpm. Five ml of the second seed culture was inoculated into a 500-ml flask containing 100 ml of the second vegetative medium. The third seed culture was incubated at 28 degree C. for 1 day on a rotary shaker operating at 250 rpm. Approximately 2 to 3 gram of sterile Amberlite XAD-7 resin were added to the third seed culture. The third seed culture was further incubated at 28 degree C. for 2 days on a rotary shaker operating at 250 rpm. Five ml of the third culture was inoculated into a 500-ml flask containing 100 ml of the second vegetative medium. The fourth seed culture was incubated at 28 degree C. for 1 day on a rotary shaker operating at 250 rpm. Approximately 2 to 3 gram of sterile Amberlite XAD-7 resin were added to the fourth seed culture. The fourth seed culture was further incubated at 28 degree C. for 1 day on a rotary shaker operating at 250 rpm. Five ml each of the fourth seed culture was inoculated into ten 500-ml flasks containing 100 ml of the second vegetative medium. The fifth seed cultures were incubated at 28 degree C. for 1 day on a rotary shaker operating at 250 rpm. Approximately 2 to 3 grams of sterile Amberlite XAD-7 resin were added to the fifth seed cultures. The fifth seed cultures were further incubated at 28 degree C. for 3 days on a rotary shaker operating at 250 rpm. Four ml each of the fifth seed culture was inoculated into one hundred and fifty 500-ml flasks containing 100 ml of the production medium having the same composition as the second vegetative medium. Approximately 2 to 3 grams of sterile Amberlite XAD-7 resin were also added to the production culture. The production cultures were incubated at 28 degree C. for 6 days on a rotary shaker operating at 250 rpm. The culture broth was filtered through cheese cloth to recover the Amberlite XAD-7 resin. The resin was extracted with 2 times 3 liters ethyl acetate followed by 1 time 1 liter ethyl acetate. The combined extracts were dried in vacuo. The dried extract, containing 0.42 g of Starting Compound II-17 and 0.16 gram Compound of Formula II-18, was then processed for the recovery of the compounds.

Example 5

Purification of Starting Compound II-17, II-18 and Compound II-27

The pure Compounds II-17 and II-18 were obtained by reversed-phase HPLC as described below:

| | |
|---|---|
| Column | ACE 5 C18-HL |
| Dimensions | 15 cm × 21 mm ID |
| Flow rate | 14.5 ml/min |
| Detection | 214 nm |
| Solvent | Gradient of 35% Acetonitrile/65% $H_2O$ to 90% Acetonitrile/10% $H_2O$ over 15 min |

Crude extract (100 mg) was dissolved in 15 ml of acetonitrile. Aliquots (900 ul) of this solution were injected onto a reversed-phase HPLC column using the conditions described above. Compounds II-17 and II-18 eluted at 7.5 and 9 minutes, respectively. Fractions containing the pure compounds were first concentrated using nitrogen to remove organic solvent. The remaining solution was then frozen and lyophilized to dryness.

An alternative purification method for Compound II-17 and II-18 was developed for larger scale purification and involved fractionation of the crude extract on a normal phase VLC column. Under these conditions, sufficient amounts of several minor metabolites were identified, including compound II-27. The crude extract (2.4 g) was dissolved in acetone (10 ml) and this solution adsorbed onto silica gel (10 cc) by drying in vacuo. The adsorbed crude extract was loaded on a normal phase silica VLC column (250 cc silica gel, column dimensions 2.5 cm diameter by 15 cm length) and washed with a step gradient of hexane/EtOAc, increasing in the percentage of hexane in steps of 5% (100 ml solvent per step). The majority of Compound II-16 eluted in the 60% hexane/40% EtOAc wash while the majority of Compound II.17 eluted in the 50% hexane/50% ethyl acetate wash. Final separation of the compounds was achieved using C18 HPLC chromatography (ACE 5µ C18-HL, 150 mm×21 mm ID) using an isocratic solvent system consisting of 35% ACN/65% $H_2O$. Under these conditions, compound II-27 eluted at 11 minutes, compound II-17 eluted at 12.00 minutes, traces of Compound II-16 eluted at 23.5 minutes, and Compound II-18 eluted at 25.5 minutes. The resulting samples were dried in vacuo using no heat to remove the aqueous solvent mixture. The spectroscopic data for these samples of Compound II-16 and Compound II-18 were found to be identical with those of samples prepared from earlier purification methods. The sample of compound II-18 was found to contain 8% of the lactone hydrolysis product and was further purified by washing through a normal phase silica plug (1 cm diameter by 2 cm height) and eluting using a solvent mixture of 20% EtOAc/80% Hexanes (25 ml). The resulting sample was found to contain pure Compound II-18.

The fractions containing compound II-27 described above were further purified using normal phase semi preparative HPLC (Phenomenex Luna Si 10μ, 100 Å; 250×10 mm id) using a solvent gradient increasing from 100% hexane to 100% EtOAc over 20 minutes with a flow rate of 4 ml/min. Compound II-27 eluted as a pure compound after 11.5 minutes (0.8 mg, 0.03% isolated yield from dried extract weight).

Starting Compound II-17: UV (Acetonitrile/H$_2$O) $\lambda_{max}$ 225(sh) nm. High Res. Mass (APCI): m/z 280.156 (M+H), $\Delta_{calc}$=2.2 ppm, $C_{15}H_{22}NO_4$.

Figure 14:
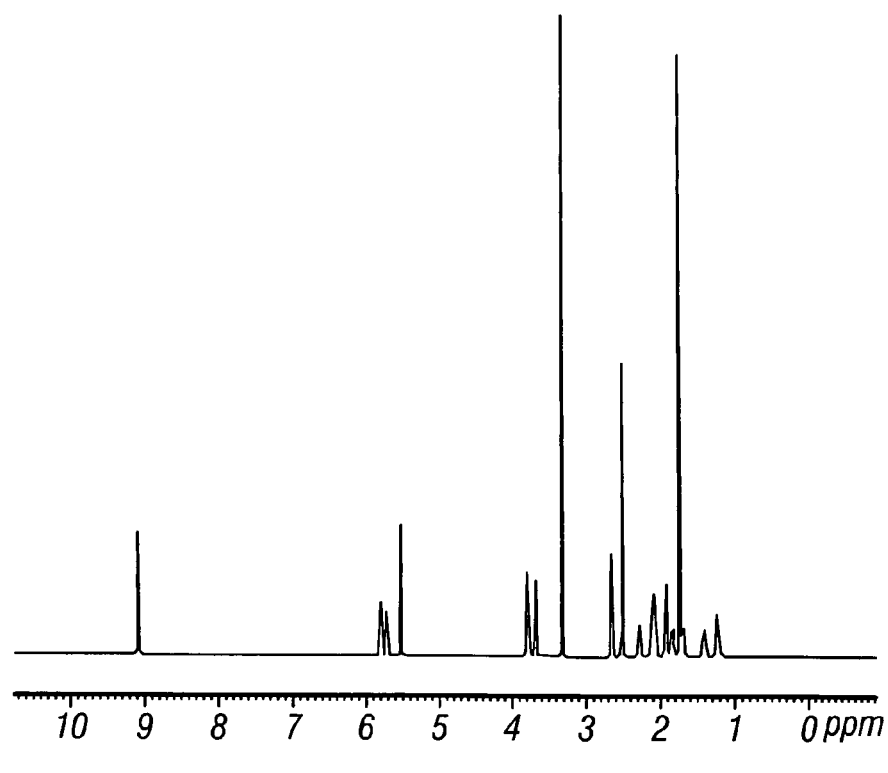
FIG. 14 depicts the $^1$H NMR spectrum of the compound of Formula II-18.

Compound II-18: UV (Acetonitrile/H$_2$O) $\lambda_{max}$ 225(sh) nm. High Res. Mass (APCI): m/z 358.065 (M+H), $\Delta_{calc}$=−1.9 ppm, $C_{15}H_{21}NO_4Br$. 1H NMR in DMSO-d6 (see FIG. 14).

Figure 25:
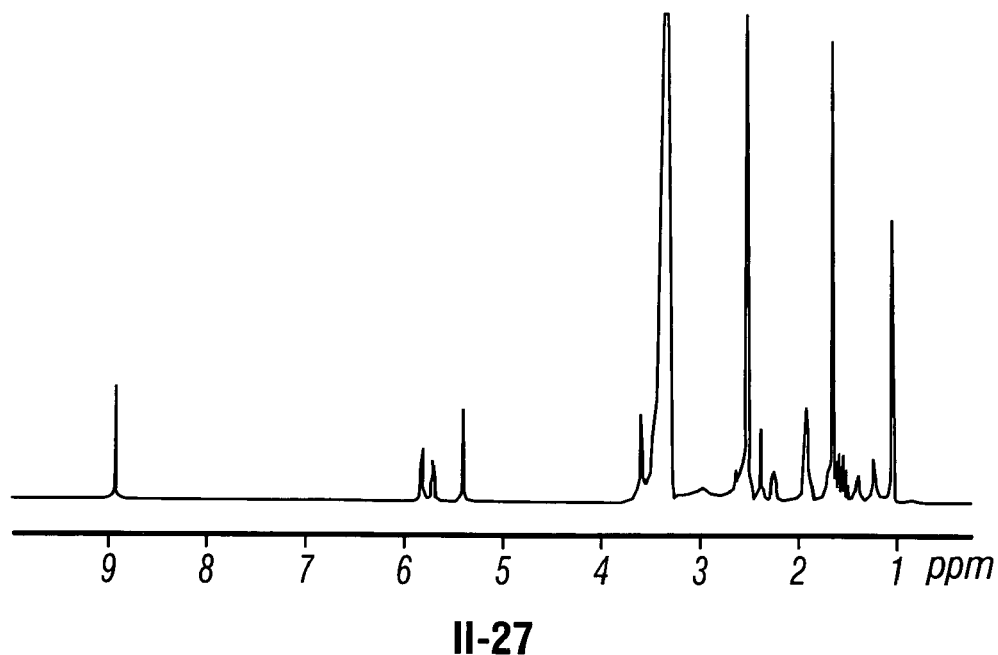
FIG. 25 depicts the $^1$H NMR spectrum of the compound of Formula II-27 in DMSO-$d_6$.
Figure 24:
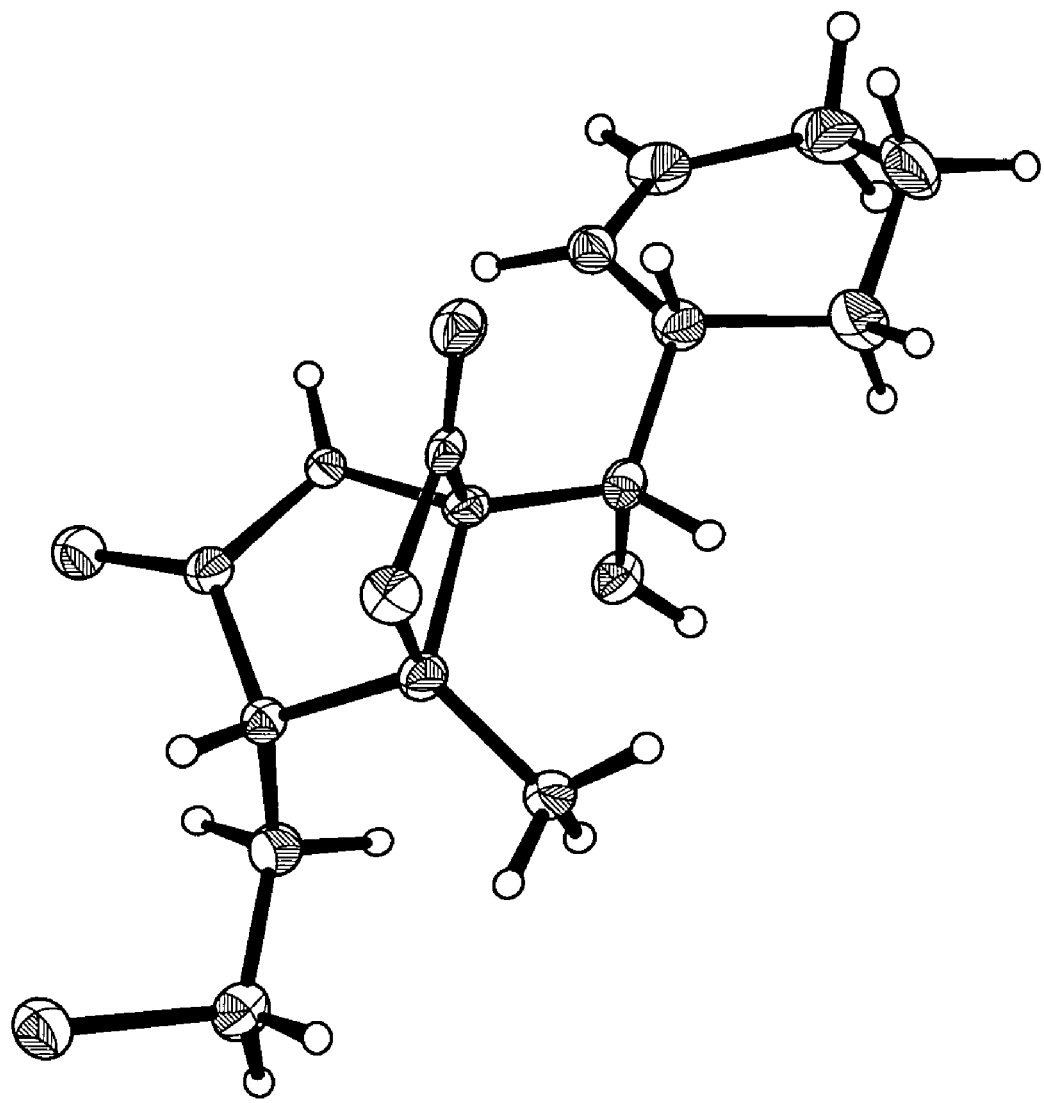
FIG. 24 depicts the computer-generated ORTEP plot of the compound of Formula II-26.

Compound II-27: UV (Acetonitrile/H$_2$O) $\lambda_{max}$ 225(sh) nm; MS (HR-ESI), m/z 280.1556 (M+H) $\Delta_{calc}$=2.7 ppm ($C_{15}H_{22}NO_4$); $^1$H NMR (DMSO-d$_6$) see FIG. 25.

Example 6

Preparation of Compound of Formula II-19 from Starting Compound II-16

Figure 15:
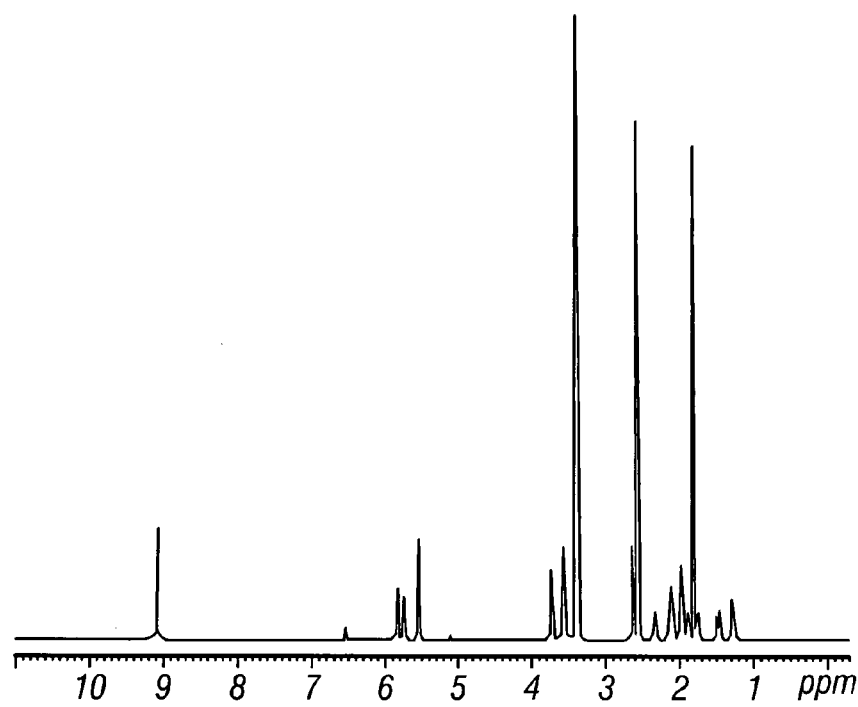
FIG. 15 depicts the $^1$H NMR spectrum of the compound of Formula II-19.

A sample of Compound II-16 (250 mg) was added to an acetone solution of sodium iodide (1.5 g in 10 ml) and the resulting mixture stirred for 6 days. The solution was then filtered through a 0.45 micron syringe filter and injected directly on a normal phase silica HPLC column (Phenomenex Luna 10u Silica, 25 cm×21.2 mm). in 0.95 ml aliquots. The HPLC conditions for the separation of compound formula II-19 from unreacted Compound II-16 employed an isocratic HPLC method consisting of 24% ethyl acetate and 76% hexane, in which the majority of compound II-19 eluted 2.5 minutes before Compound II-16. Equivalent fractions from each of 10 injections were pooled to yield 35 mg compound II-19. Compound II-19: UV (Acetonitrile/H$_2$O) 225 (sh), 255 (sh) rum; ESMS, m/z 406.0 (M+H); HRMS (ESI), m/z 406.0513 [M+H]$^+$, $\Delta_{calc}$=−0.5 ppm, $C_{15}H_{21}NO_4I$; $^1$H NMR in DMSO-d$_6$ (see FIG. 15).

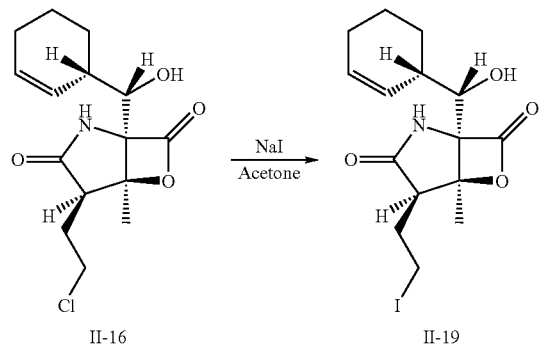

Example 7

Synthesis of the Compounds of Formulae II-2, II-3, and II-4

Compounds of Formulae II-2, II-3 and II-4 can be synthesized from Starting Compounds II-16, II-17, and II-18, respectively, by catalytic hydrogenation.

Exemplary Depiction of Synthesis

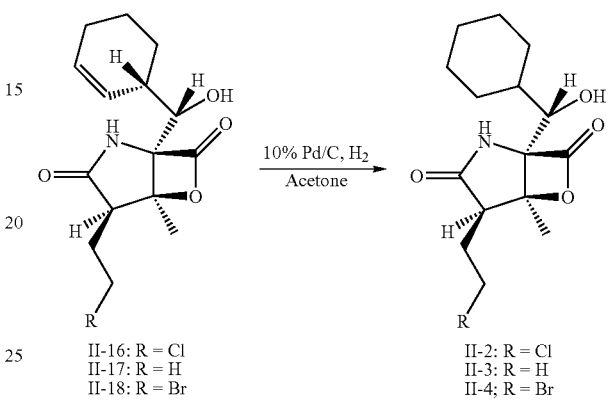

Example 7A

Catalytic Hydrogenation of Starting Compound II-16

Starting Compound II-16 (10 mg) was dissolved in acetone (5 mL) in a scintillation vial (20 mL) to which was added the 10% (w/w) Pd/C (1-2 mg) and a magnetic stirrer bar. The reaction mixture was stirred in a hydrogen atmosphere at room temperature for about 15 hours. The reaction mixture was filtered through a 3 cc silica column and washed with acetone. The filtrate was filtered again through 0.2 μm Gelman Acrodisc to remove any traces of catalyst. The solvent was evaporated off from filtrate under reduced pressure to yield the compound of Formula II-2 as a pure white powder.

Example 7B

Catalytic Hydrogenation of Starting Compound II-17

Starting Compound II-17 (5 mg) was dissolved in acetone (3 mL) in a scintillation vial (20 mL) to which was added the 10% (w/w) Pd/C (about 1 mg) and a magnetic stirrer bar. The reaction mixture was stirred in a hydrogen atmosphere at room temperature for about 15 hours. The reaction mixture was filtered through a 0.2 μm Gelman Acrodisc to remove the catalyst. The solvent was evaporated off from filtrate to yield the compound of Formula II-3 as a white powder which was purified by normal phase HPLC using the following conditions:

| | |
|---|---|
| Column: | Phenomenex Luna 10 u Silica |
| Dimensions: | 25 cm × 21.2 mm ID |
| Flow rate: | 14.5 ml/min |

-continued

| | |
|---|---|
| Detection: | ELSD |
| Solvent: | 5% to 60% EtOAc/Hex for 19 min, 60 to 100% EtOAc in 1 min, then 4 min at 100% EtOAc |

Compound of Formula II-3 eluted at 22.5 min as a pure compound.

Example 7C

Catalytic Hydrogenation of Compound II-18

3.2 mg of Starting Compound II-18 was dissolved in acetone (3 mL) in a scintillation vial (20 mL) to which was added the 10% (w/w) Pd/C (about 1 mg) and a magnetic stirrer bar. The reaction mixture was stirred in hydrogen atmosphere at room temperature for about 15 hours. The reaction mixture was filtered through a 0.2 μm Gelman Acrodisc to remove the catalyst. The solvent was evaporated off from filtrate to yield the compound of Formula II-4 as a white powder which was further purified by normal phase HPLC using the following conditions:

| | |
|---|---|
| Column: | Phenomenex Luna 10 u Silica |
| Dimensions: | 25 cm × 21.2 mm ID |
| Flow rate: | 14.5 ml/min |
| Detection: | ELSD |
| Solvent: | 5% to 80% EtOAc/Hex for 19 min, 80 to 100% EtOAc in 1 min, then 4 min at 100% EtOAc |

Compound of Formula II-4 eluted at 16.5 min as a pure compound.

Example 8

Structural Characterization

Figure 2:
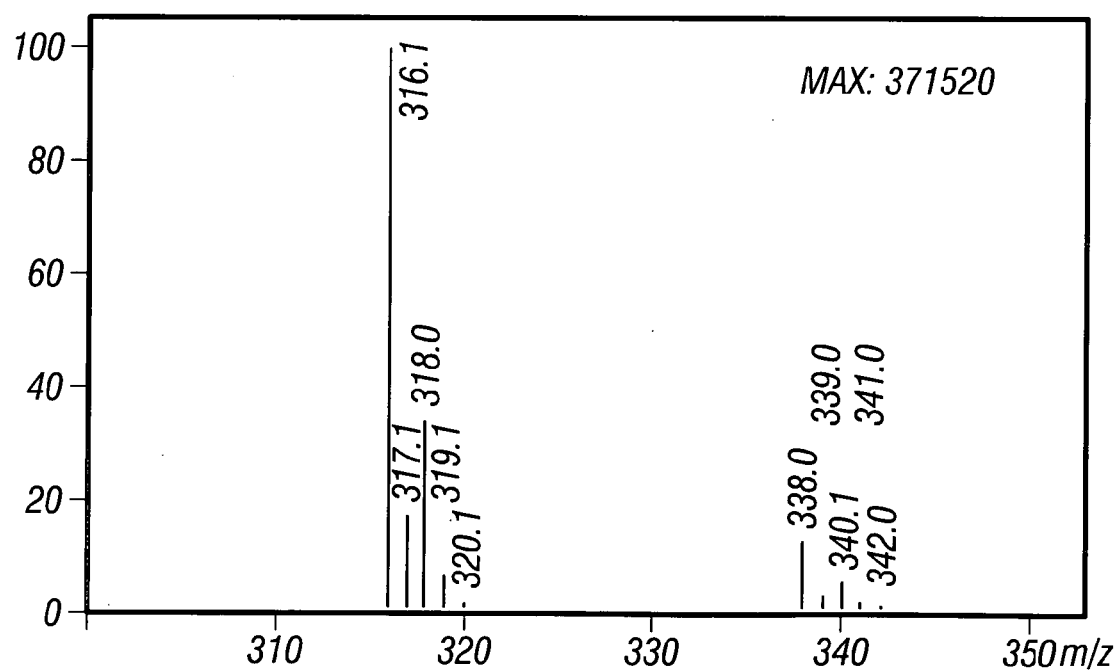
FIG. 2 depicts the mass spectrum of a compound having structure Formula II-2.
Figure 3:
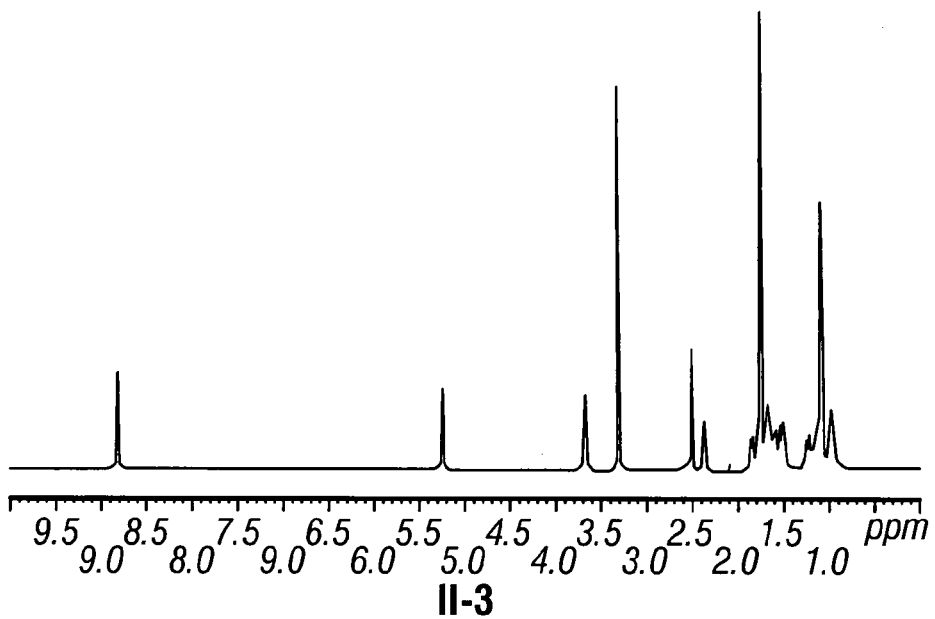
FIG. 3 depicts the $^1$H NMR spectrum of a compound having structure Formula II-3.
Figure 4:
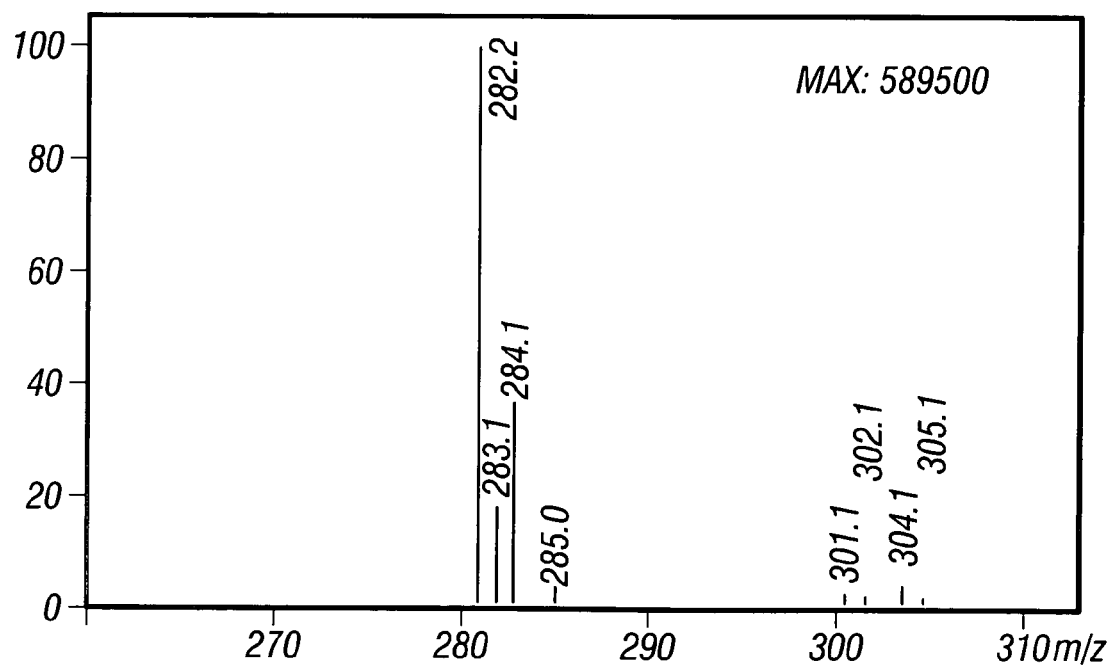
FIG. 4 depicts the mass spectrum of a compound having structure Formula II-3.
Figure 5:
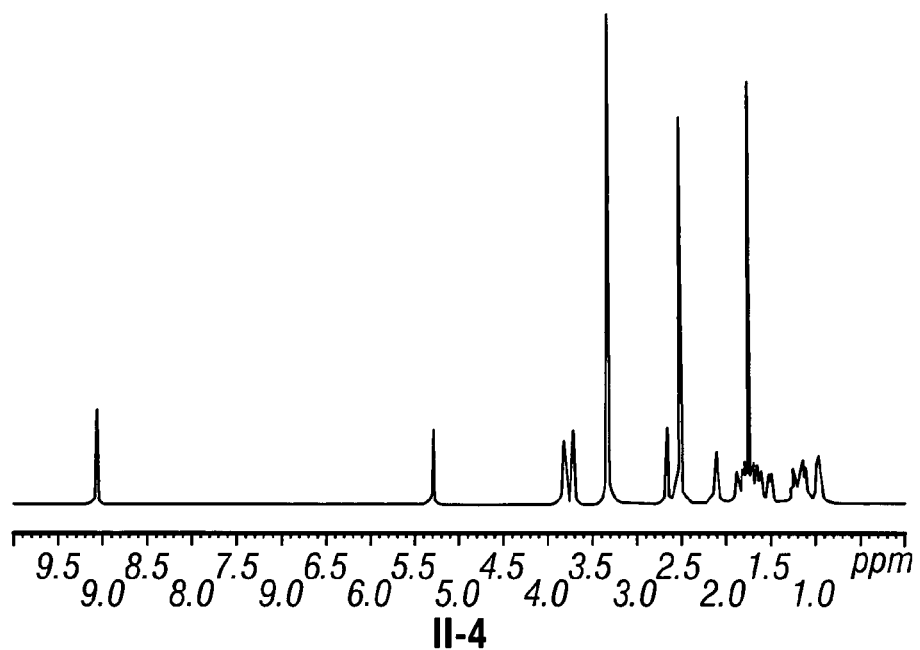
FIG. 5 depicts the $^1$H NMR spectrum of a compound having structure Formula II-4.
Figure 6:
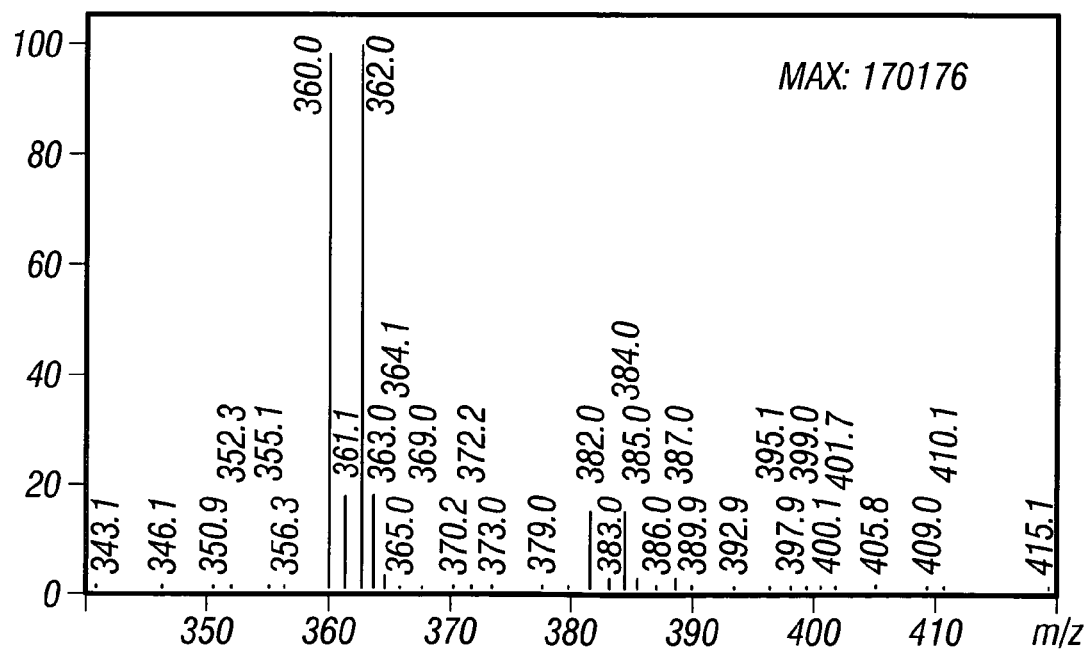
FIG. 6 depicts the mass spectrum of a compound having structure Formula II-4.

The structure of the compounds can be elucidated by various methods, including NMR, MS, and UV. FIGS. 1-6 provide spectral data from these methods. UV for compound of Formula II-2 in acetonitrile/$H_2O$: $\lambda_{max}$ 225 (sh) nm. FIG. 1 depicts the NMR spectrum of the compound of Formula II-2 in DMSO-$d_6$. FIG. 2 depicts the low resolution mass spectrum of the compound of Formula II-2: m/z 316 (M+H), 338 (M+Na). UV for compound of Formula II-3 in acetonitrile/$H_2O$: $\lambda_{max}$ 225 (sh) nm. FIG. 3 depicts the NMR spectrum of the compound of Formula II-3 in DMSO-$d_6$. FIG. 4 depicts the low resolution mass spectrum of the compound of Formula II-3: m/z 282 (M+H), 304 (M+Na). UV for compound of Formula in acetonitrile/$H_2O$: $\lambda_{max}$ 225 (sh) nm. FIG. 5 depicts the NMR spectrum of the compound of Formula II-4 in DMSO-$d_6$. FIG. 6 depicts the low resolution mass of the compound of Formula II-4: m/z 360 (M+H), 382 (M+Na).

In addition, high resolution mass spectrometry data were obtained for compounds II-2, II-3, and II-4. Compound II-2: HRMS (ESI), m/z 316.1305 [M+H]$^+$, $\Delta_{calc}$=−3.5 ppm, $C_{15}H_{23}NO_4Cl$. Compound II-3: HRMS (ESI), m/z 282.1706 [M+H]$^+$, $\Delta_{calc}$=0.3 ppm, $C_{15}H_{24}NO_4$. Compound II-4: HRMS (ESI), m/z 360.0798 [M+H]$^+$, $\Delta_{calc}$=−3.4 ppm, $C_{15}H_{23}NO_4Br$ Example 9

Synthesis of the Compounds of Formulae II-5A and II-5B

A compound of Formula II-5A and Formula II-5B can be synthesized from Starting Compound II-16 by epoxidation with mCPBA.

Starting Compound II-16 (101 mg, 0.32 mmole) was dissolved in methylenechloride (30 mL) in a 100 ml of round bottom flask to which was added 79 mg (0.46 mmole) of meta-chloroperbenzoic acid (mCPBA) and a magnetic stir bar. The reaction mixture was stirred at room temperature for about 18 hours. The reaction mixture was poured onto a 20 cc silica flash column and eluted with 120 ml of $CH_2Cl_2$, 75 ml of 1:1 ethyl acetate/hexane and finally with 40 ml of 100% ethyl acetate. The 1:1 ethyl acetate/hexane fractions yield a mixture of diastereomers of epoxy derivatives, Formula II-5A and II-5B, which were separated by normal phase HPLC using the following conditions:

| | |
|---|---|
| Column | Phenomenex Luna 10 u Silica |
| Dimensions | 25 cm × 21.2 mm ID |
| Flow rate | 14.5 ml/min |
| Detection | ELSD |
| Solvent | 25% to 80% EtOAc/Hex over 19 min, 80 to 100% EtOAc in 1 min, then 5 min at 100% EtOAc |

Compound Formula II-5A (major product) and II-5B (minor product) eluted at 21.5 and 19 min, respectively, as pure compounds. Compound II-5B was further chromatographed on a 3 cc silica flash column to remove traces of chlorobenzoic acid reagent.

Chemical Structures:

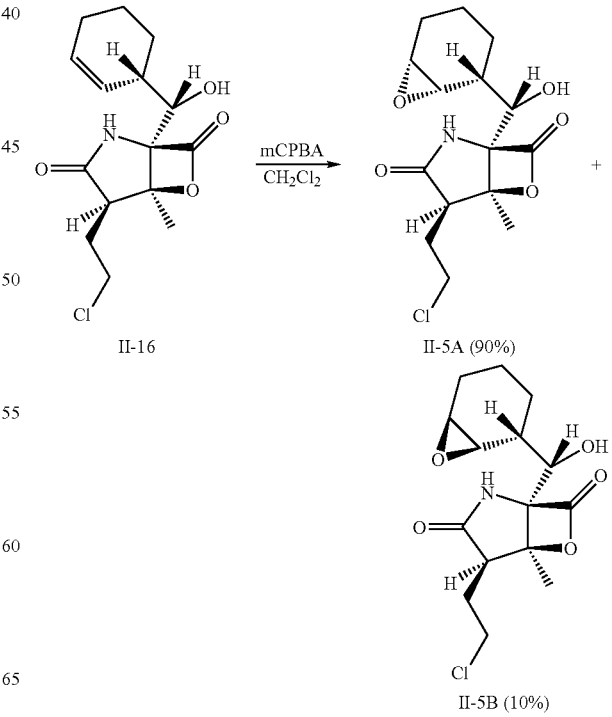

Structural Characterization

Figure 7:
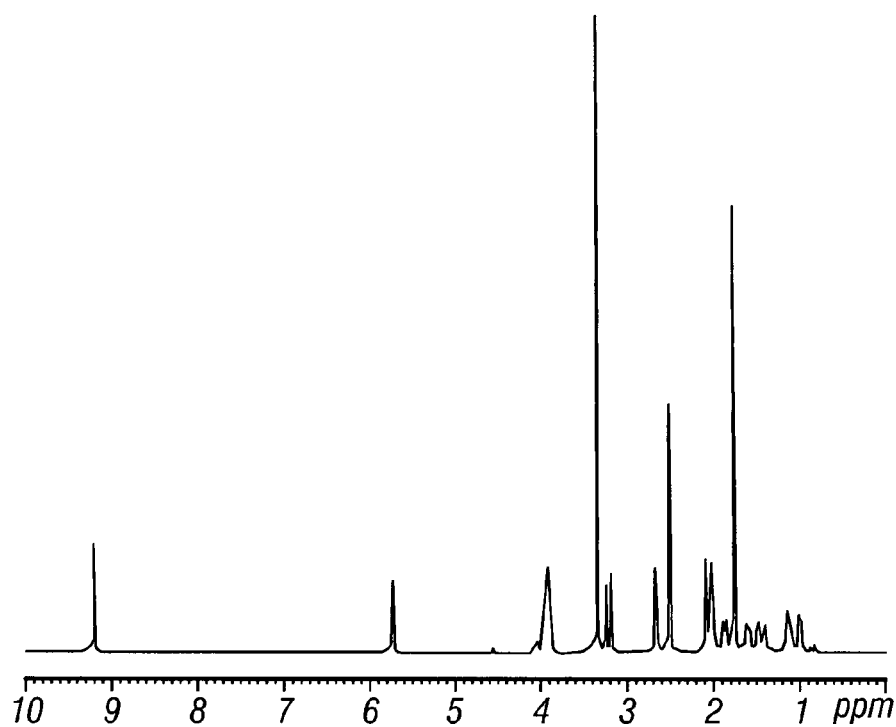
FIG. 7 depicts the $^1$H NMR spectrum of a compound having structure Formula II-5A.
Figure 8:
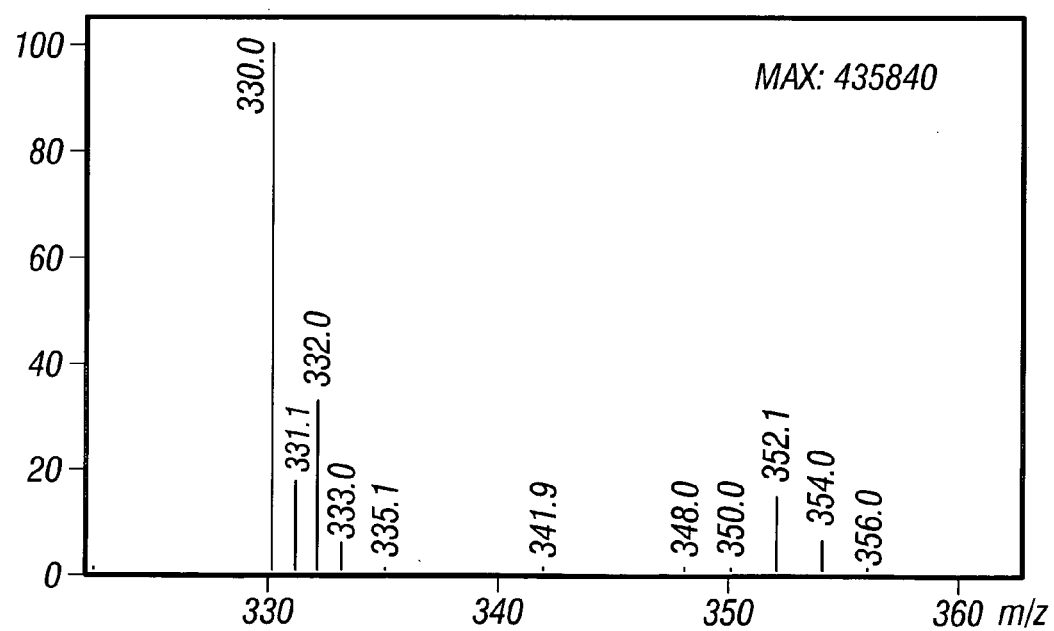
FIG. 8 depicts the mass spectrum of a compound having structure Formula II-5A.

Formula II-5A: UV (Acetonitrile/H$_2$O) $\lambda_{max}$ 225 (sh) nm. Low Res. Mass: m/z 330 (M+H), 352 (M+Na). HRMS (ESI), m/z 330.1099 [M+H]$^+$, $\Delta_{calc}$=–2.9 ppm, C$_{15}$H$_{21}$NO$_5$Cl. FIGS. 7 and 8, respectively depict the 1H NMR spectrum of Formula II-5A and the mass spectrum of Formula II-5A.

Figure 9:
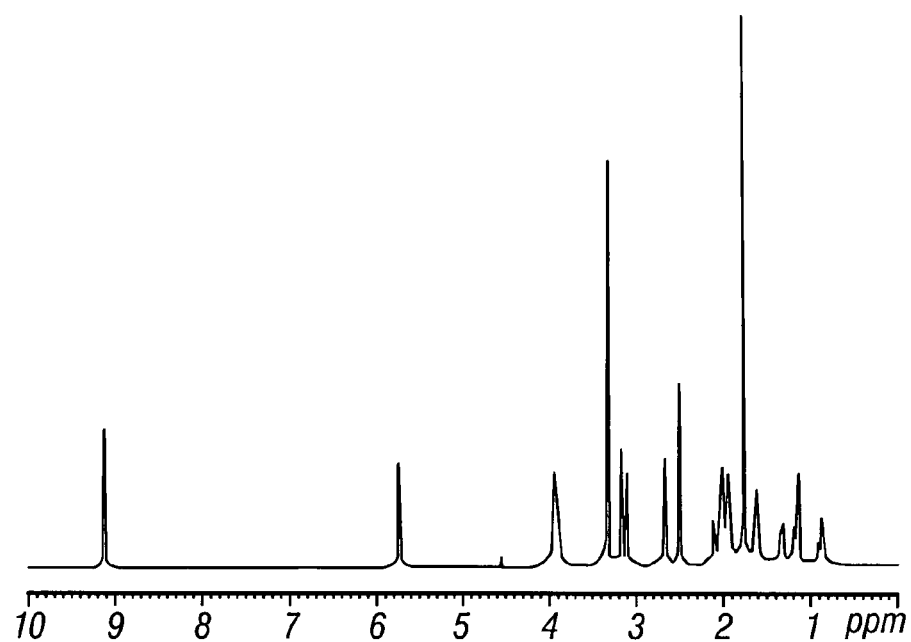
FIG. 9 depicts the $^1$H NMR spectrum of a compound having structure Formula II-5B.
Figure 10:
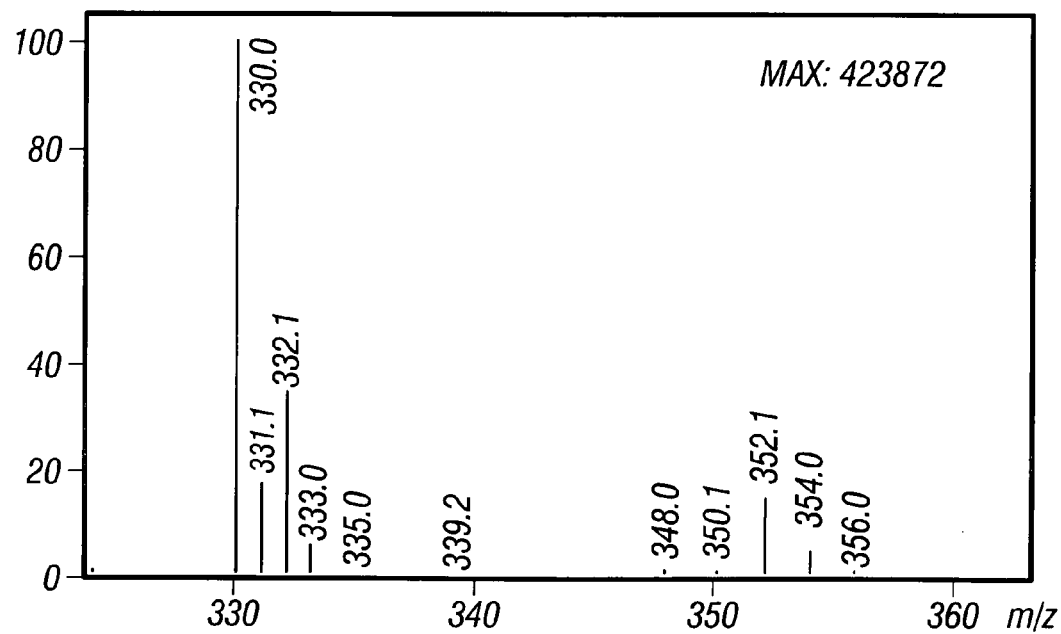
FIG. 10 depicts the mass spectrum of a compound having structure Formula II-5B.
Figure 11:
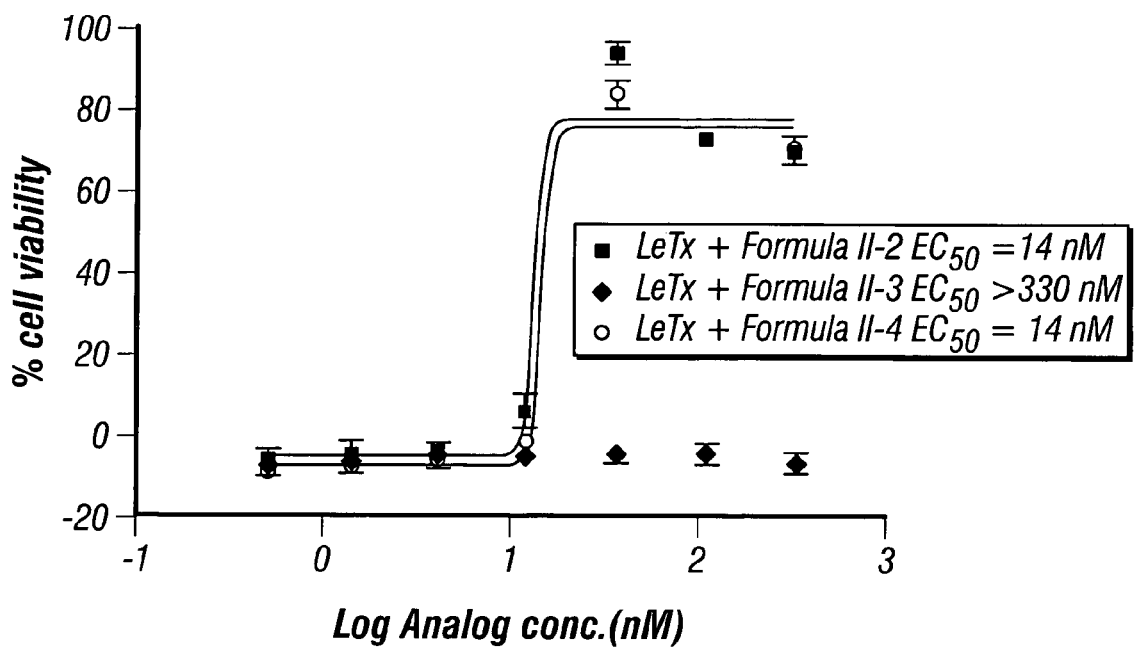
FIG. 11 depicts the effect of Formulae II-2, II-3, and II-4 against LeTx-mediated cytotoxicity.

Formula II-5B: UV (Acetonitrile/H$_2$O) $\lambda_{max}$ 225 (sh) nm. Low Res. Mass: m/z 330 (M+H), 352 (M+Na). HRMS (ESI), m/z 330.1105 [M+H]$^+$, $\Delta_{calc}$=–0.9 ppm, C$_{15}$H$_{21}$NO$_5$Cl. FIGS. 9 and 10, respectively depict the 1H NMR spectrum of II-5B and the mass spectrum of II-5B.

Example 10

Synthesis of the Compounds of Formulae IV-1, IV-2, IV-3 and IV-4

Synthesis of Diol Derivatives (Formula IV-2)

Diols can be synthesized by Sharpless dihydroxylation using AD mix-α and β: AD mix-α is a premix of four reagents, K$_2$OsO$_2$(OH)$_4$; K$_2$CO$_3$; K$_3$Fe(CN)$_6$; (DHQ)$_2$-PHAL [1,4-bis(9-O-dihydroquinine)phthalazine] and AD mix-β is a premix of K$_2$OsO$_2$(OH)$_4$; K$_2$CO$_3$; K$_3$Fe(CN)$_6$; (DHQD)$_2$-PHAL [1,4-bis(9-O-dihydroquinidine)phthalazine] which are commercially available from Aldrich. Diol can also be synthesized by acid or base hydrolysis of epoxy compounds (Formula II-5A and II-5B) which can be different to that of products obtained in Sharpless dihydroxylation in their stereochemistry at carbons bearing hydroxyl groups Sharpless Dihydroxylation of Starting Compounds II-16, II-17 and II-18

The starting compounds are dissolved in t-butanol/water in a round bottom flask to which is added AD mix-α or β and a magnetic stir bar. The reaction are monitored by silica TLC as well as mass spectrometer. The pure diols are obtained by usual workup and purification by flash chromatography or HPLC. The structures are confirmed by NMR spectroscopy and mass spectrometry. In this method both hydroxyl groups are on same side.

Nucleophilic Ring Opening of Epoxy Compounds (II-5):

The epoxy ring is opened with various nucleophiles like NaCN, NaN$_3$, NaOAc, HBr, etc. to substitute various groups on cyclohexane ring with hydroxyl group one side.

Examples

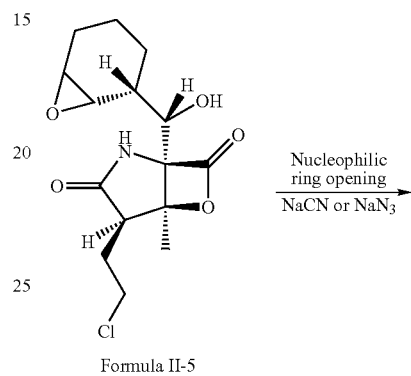

Formula II-5

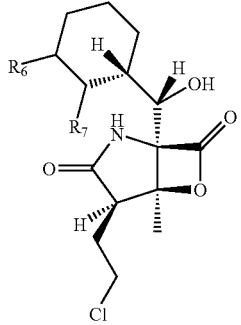

R7: CN or N3 if R6 is OH
R6: CN or N3 if R7 is OH
Formula IV-1

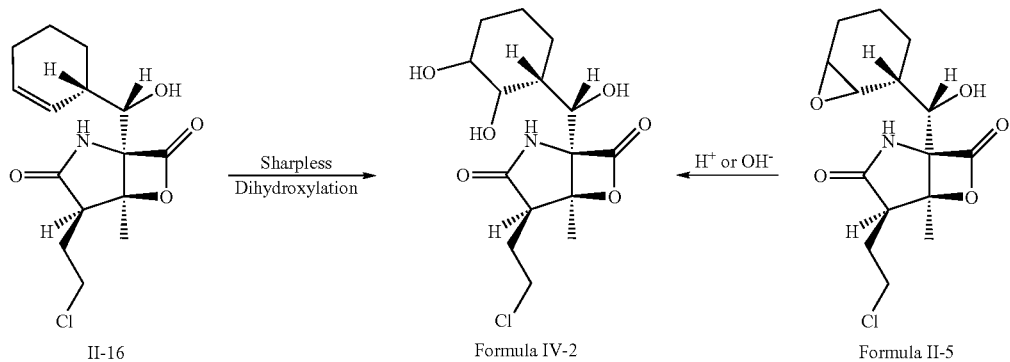

II-16          Formula IV-2          Formula II-5

The epoxy is opened with HCl to make Formula IV-3:

Reductive ring opening of epoxides (II-5): The compound of Formula is treated with metalhydrides like BH$_3$-THF complex to make compound of Formula IV-4.

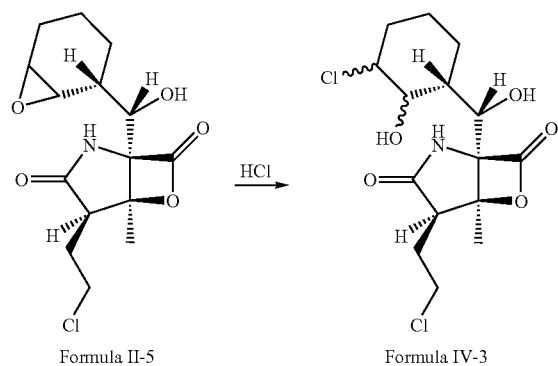

Formula II-5 → Formula IV-3

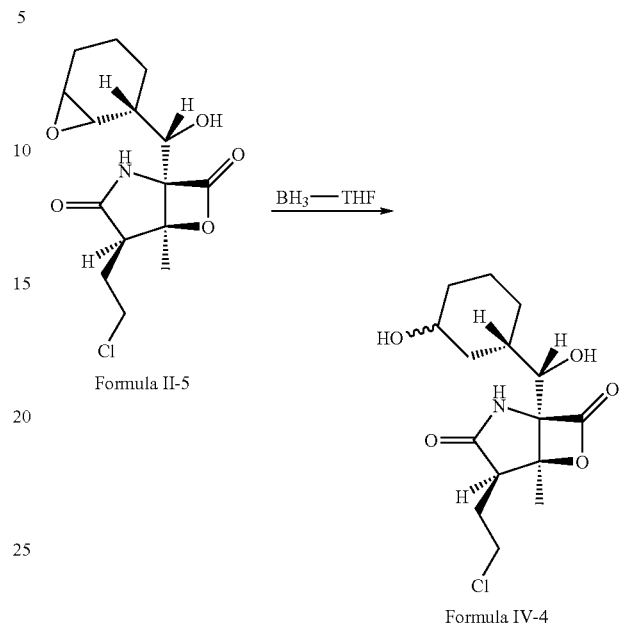

Formula II-5 → Formula IV-4

Figure 21:
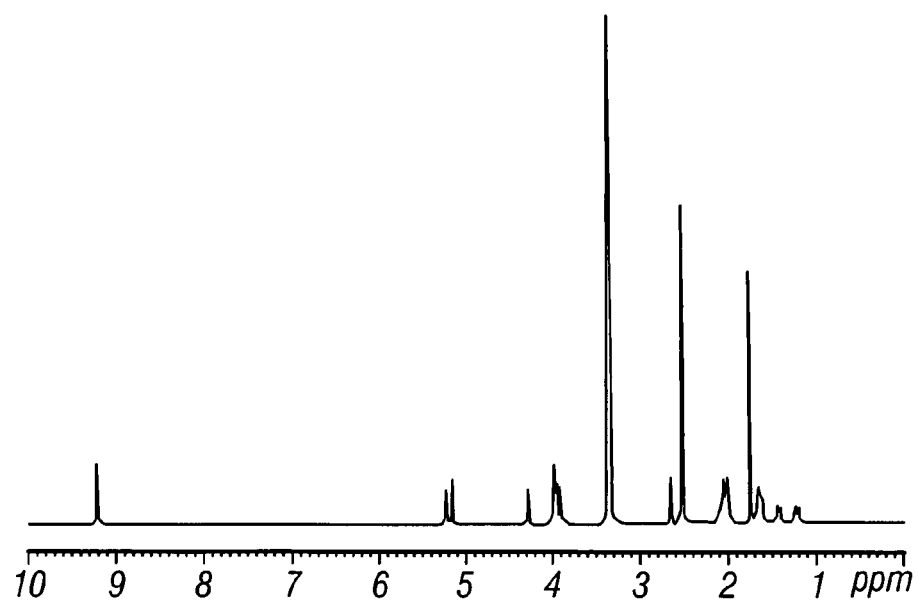
FIG. 21 depicts the $^1$H NMR spectrum of the compound of Formula IV-3C in DMSO-$d_6$.
Figure 22:
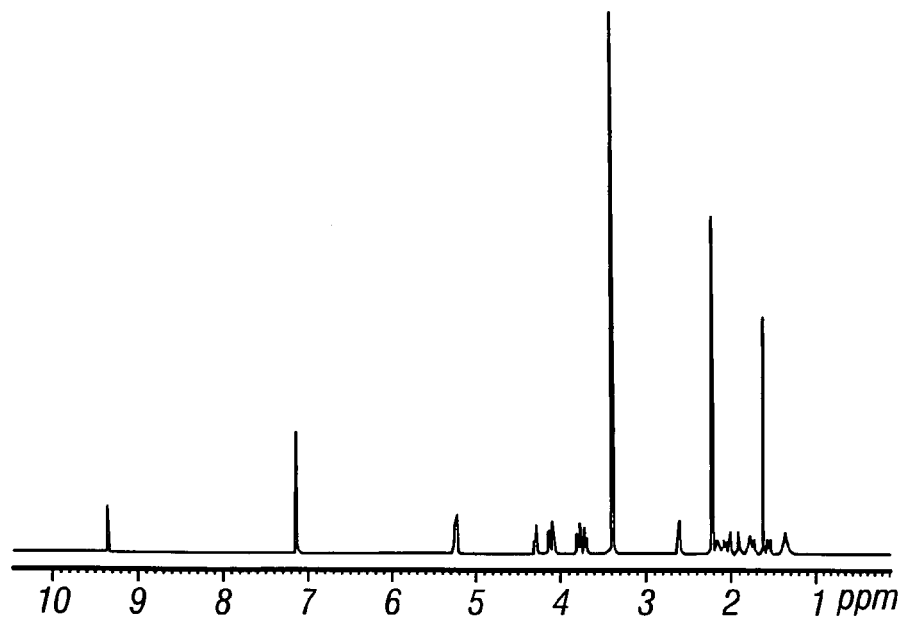
FIG. 22 depicts the $^1$H NMR spectrum of the compound of Formula IV-3C in $C_6D_6$/DMSO-$d_6$.

Compound of Formula II-5A (3.3 mg) was dissolved in acetonitrile (0.5 ml) in a 1 dram vial to which was added 5% HCl (500 ul) and a magnetic stir bar. The reaction mixture was stirred at room temperature for about an hour. The reaction was monitored by mass spectrometry. The reaction mixture was directly injected on normal phase HPLC to obtain compound of Formula IV-3C as a pure compound without any work up. The HPLC conditions used for the purification were as follows: Phenomenex Luna 10u Silica column (25 cm×21.2 mm ID) with a solvent gradient of 25% to 80% EtOAc/Hex over 19 min, 80 to 100% EtOAc in 1 min, then 5 min at 100% EtOAc at a flow rate of 14.5 ml/min. An ELSD was used to monitor the purification process. Compound of Formula IV-3C eluted at about 18 min (2.2 mg). Compound of Formula IV-3C: UV (Acetonitrile/H$_2$O) $\lambda_{max}$ 225 (sh) nm; ESMS, m/z 366 (M+H), 388 (M+Na); HRMS (ESI), m/z 366.0875 [M+H]$^+$, $\Delta_{calc}$=0.0 ppm, C$_{15}$H$_{22}$NO$_5$Cl$_2$; $^1$H NMR in DMSO-d6 (FIG. 21) The stereochemistry of the compound of Formula IV-3C was determined based on coupling constants observed in the cyclohexane ring in 1:1 C$_6$D$_6$/DMSO-d6 (FIG. 22).

Example 11

Synthesis of the Compounds of Formulae II-13C and II-8C

Figure 13:
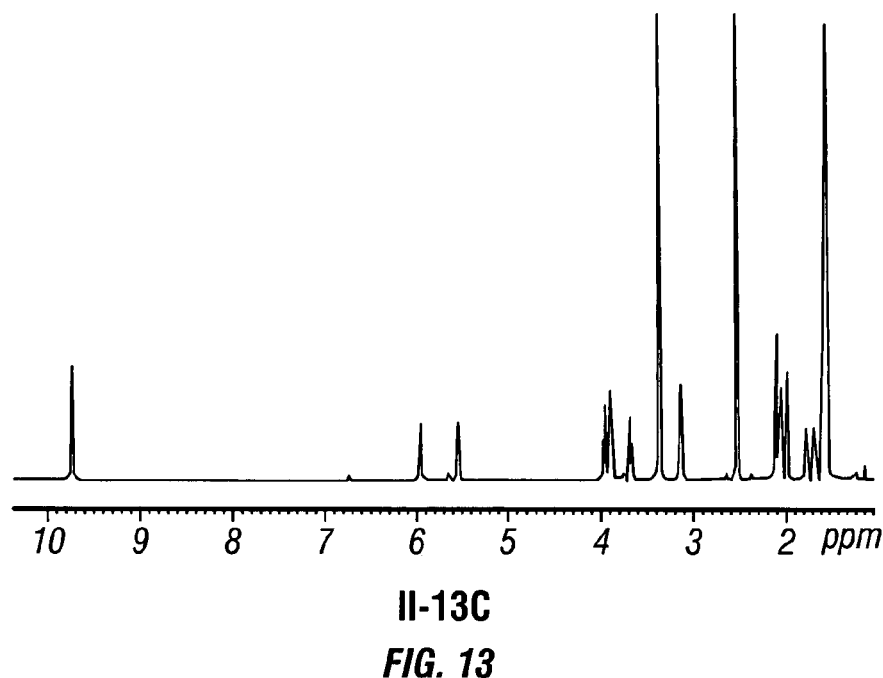
FIG. 13 depicts the $^1$H NMR spectrum of the compound of Formula II-13C.

Compound II-16 (30 mg) was dissolved in CH$_2$Cl$_2$ (6 ml) in a scintillation vial (20 ml) to which Dess-Martin Periodinane (122 mg) and a magnetic stir bar were added. The reaction mixture was stirred at room temperature for about 2 hours. The progress of the reaction was monitored by TLC (Hex:EtOAc, 6:4) and analytical HPLC. From the reaction mixture, the solvent volume was reduced to one third, absorbed on silica gel, poured on top of a 20 cc silica flash column and eluted in 20 ml fractions using a gradient of Hexane/EtOAc from 10 to 100%. The fraction eluted with 30% EtOAc in Hexane contained a mixture of rotamers of Formula II-13C in a ratio of 1.5:8.5. The mixture was further purified by normal phase HPLC using the Phenomenex Luna 10u Silica column (25 cm×21.2 mm ID) with a solvent gradient of 25% to 80% EtOAc/Hex over 19 min, 80 to 100% EtOAc over 1 min, holding at 100% EtOAc for 5 min, at a flow rate of 14.5 ml/min. An ELSD was used to monitor the purification process. Compound of Formula II-13C eluted at 13.0 and 13.2 mins as a mixture of rotamers with in a ratio of 1.5:8.5 (7 mg). Formula II-13C: UV (Acetonitrile/H$_2$O) $\lambda_{max}$ 226 (sh) & 300 (sh) nm; ESMS, m/z 312 (M+H)$^+$, 334 (M+Na)$^+$; HRMS (ESI), m/z 312.1017 [M+H]$^+$, $\Delta_{calc}$=4.5 ppm, C$_{15}$H$_{19}$NO$_4$Cl; $^1$H NMR in DMSO-d$_6$ (see FIG. 13).

Figure 12:
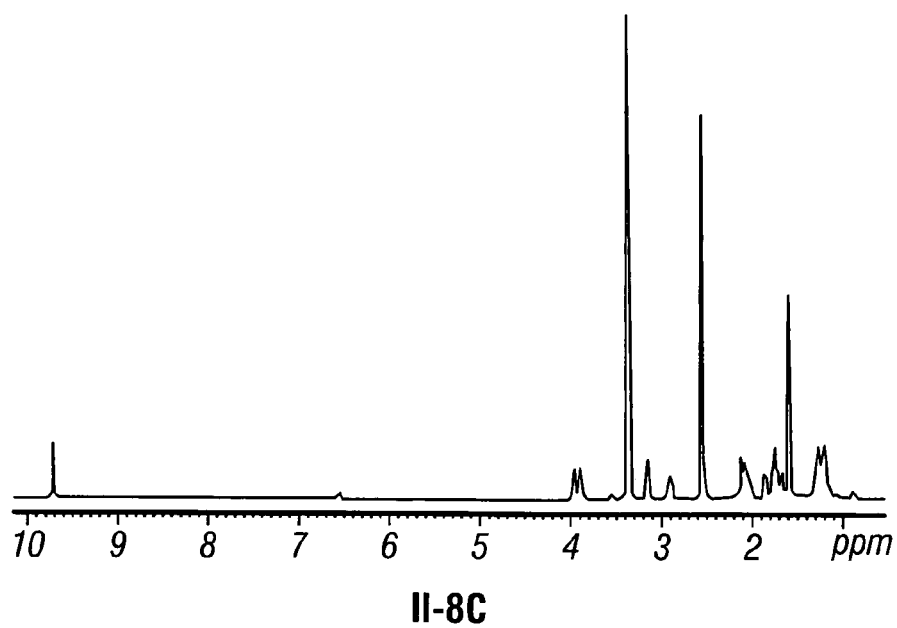
FIG. 12 depicts the $^1$H NMR spectrum of the compound of Formula II-8C.

The rotamer mixture of Formula II-13C (4 mg) was dissolved in acetone (1 ml) in a scintillation vial (20 ml) to which a catalytic amount (0.5 mg) of 10% (w/w) Pd/C and a magnetic stir bar were added. The reaction mixture was stirred in a hydrogen atmosphere at room temperature for about 15 hours. The reaction mixture was filtered through a 0.2 μm Gelman Acrodisc to remove the catalyst. The solvent was evaporated from the filtrate to yield compound of Formula II-8C as a colorless gum which was further purified by normal phase HPLC using a Phenomenex Luna 10u Silica column (25 cm×21.2 mm ID) with a solvent gradient of 25% to 80% EtOAc/Hex over 19 min, 80 to 100% EtOAc over 1 min, holding at 100% EtOAc for 5 min, at a flow rate of 14.5 ml/min. An ELSD was used to monitor the purification process. Compound of Formula II-8C (1 mg) eluted at 13.5 min as a pure compound. Formula II-8C: UV (Acetonitrile/H$_2$O) $\lambda_{max}$ 225 (sh) nm; ESMS, m/z 314 (M+H)$^+$, 336 (M+Na)$^+$; HRMS (ESI), m/z 314.1149 [M+H]$^+$, $\Delta_{calc}$=3.3 ppm, $C_{15}H_{21}NO_4Cl$; $^1$H NMR in DMSO-d$_6$ (See FIG. 12).

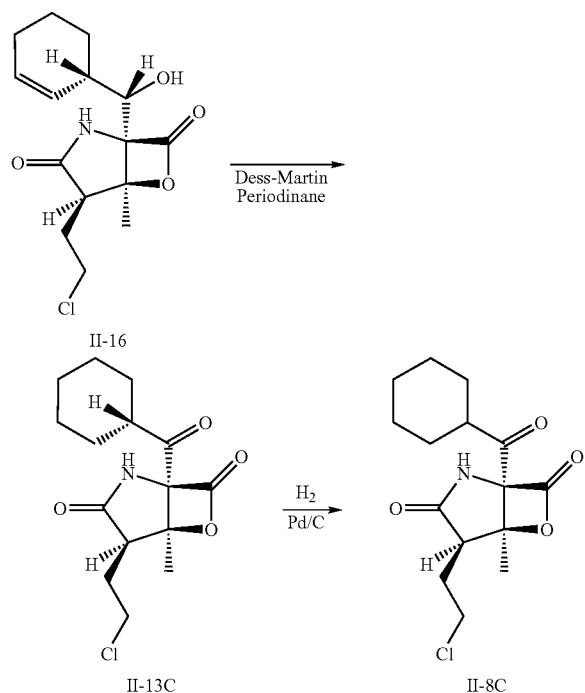

Example 12

Synthesis of the Compound of Formulae II-25 from II-13C

Figure 20:
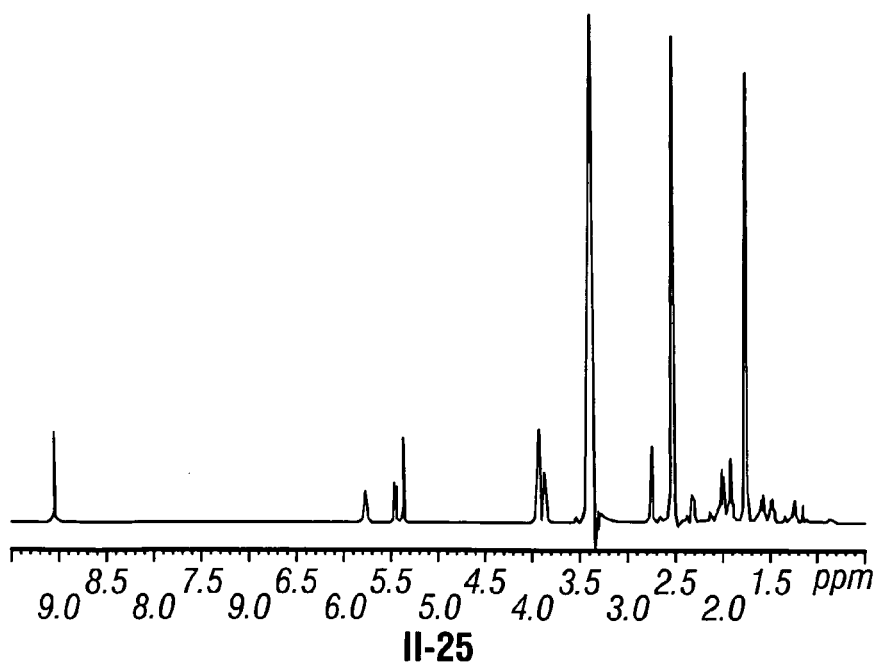
FIG. 20 depicts the $^1$H NMR spectrum of the compound of Formula II-25.

The rotamer mixture of Formula II-13C (5 mg) was dissolved in dimethoxy ethane (monoglyme; 1.5 ml) in a scintillation vial (20 ml) to which water (15 μl (1% of the final solution concentration)) and a magnetic stir bar were added. The above solution was cooled to −78° C. on a dry ice-acetone bath, and a sodium borohydride solution (3.7 mg of NaBH$_4$ in 0.5 ml of monoglyme (created to allow for slow addition)) was added drop-wise. The reaction mixture was stirred at −78° C. for about 14 minutes. The reaction mixture was acidified using 2 ml of 4% HCl solution in water and extracted with CH$_2$Cl$_2$. The organic layer was evaporated to yield mixture of compound of formulae II-25 and II-16 in a 9.5:0.5 ratio as a white solid, which was further purified by normal phase HPLC using a Phenomenex Luna 10u Silica column (25 cm×21.2 mm ID). The mobile phase was 24% EtOAc/76% Hexane, which was held isocratic for 19 min, followed by a linear gradient of 24% to 100% EtOAc over 1 min, and held at 100% EtOAc for 3 min; the flow rate was 25 ml/min. An ELSD was used to monitor the purification process. Compound of Formula II-25 (1.5 mg) eluted at 11.64 min as a pure compound. Compound of Formula II-25: UV (Acetonitrile/H$_2$O) $\lambda_{max}$ 225 (sh) nm; ESMS, m/z 314 (M+H)$^+$, 336 (M+Na)$^+$; HRMS (ESI), m/z 314.1154 [M+H]$^+$, $\Delta_{calc}$=−0.6 ppm, $C_{15}H_{21}NO_4Cl$; $^1$H NMR in DMSO-d$_6$ (see FIG. 20).

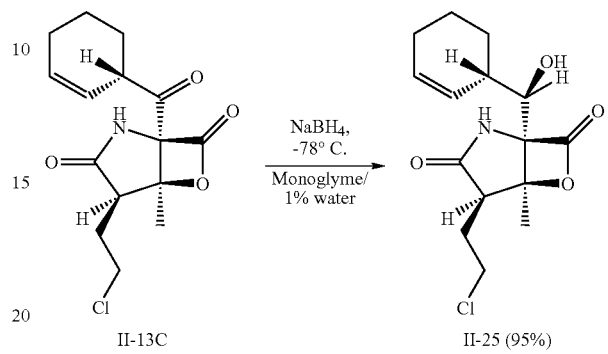

Example 13

Synthesis of the Compounds of Formulae II-31, II-32 and II-49 from II-13C, and Compounds of Formulae II-33, II-34, II-35 and II-36 from II-31 and II-32

A rotamer mixture of the Compound of Formula II-13C (20 mg) was dissolved in acetone (4 ml) in a scintillation vial (20 ml) to which a catalytic amount (3 mg) of 10% (w/w) Pd/C and a magnetic stir bar were added. The reaction mixture was stirred at room temperature for about 15 hours. The reaction mixture was filtered through a 0.2 μm Gelman Acrodisc to remove the catalyst. The solvent was evaporated from the filtrate to yield a mixture of diastereomers of hydroxy derivatives of Formulae II-31 and II-32 (1:1), and a minor compound II-49, which were separated by reversed phase HPLC using Ace 5u C18 column (150 mm×22 mm ID) with a solvent gradient of 90% to 30% H$_2$O/Acetonitrile over 15 min, 70 to 100% Acetonitrile over 5 min, holding at 100% Acetonitrile for 4 min, at a flow rate of 14.5 ml/min. A diode array detector was used to monitor the purification process. Compound II-31 (2 mg), II-32 (2 mg) and II-49 (0.2 mg) eluted at 10.6, 10.8 and 11.54 min, respectively, as pure compounds. II-31: UV (Acetonitrile/H$_2$O) $\lambda_{max}$ 250 (sh) nm; ESMS m/z 328.1 (M+H)$^+$ & 350.0 (M+Na)$^+$. II-32: UV (Acetonitrile/H$_2$O) $\lambda_{max}$ 250 (sh) nm; ESMS, m/z 328.1 (M+H)$^+$ & 350.0 (M+Na)$^+$. II-49: UV (Acetonitrile/H$_2$O) $\lambda_{max}$ 250 (sh) and 320 nm; ESMS, m/z 326.0 (M+H)$^+$, 343.1 (M+H$_2$O)$^+$ & 348.0 (M+Na)$^+$.

In an alternate method, compounds II-31, II-32 and II-49 were separated by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process.

The ketone of the compounds of formula II-31 and II-32 can be reduced by using sodium borohydride at 0 to −10° C. in monoglyme solvent for about 14 minutes. The reaction mixture can be acidified using 4% HCl solution in water and extracted with CH$_2$Cl$_2$. The organic layer can be evaporated to yield the mixtures of compounds of formulae II-33, II-34, II-35 and II-36 which can be separated by chromatographic methods.

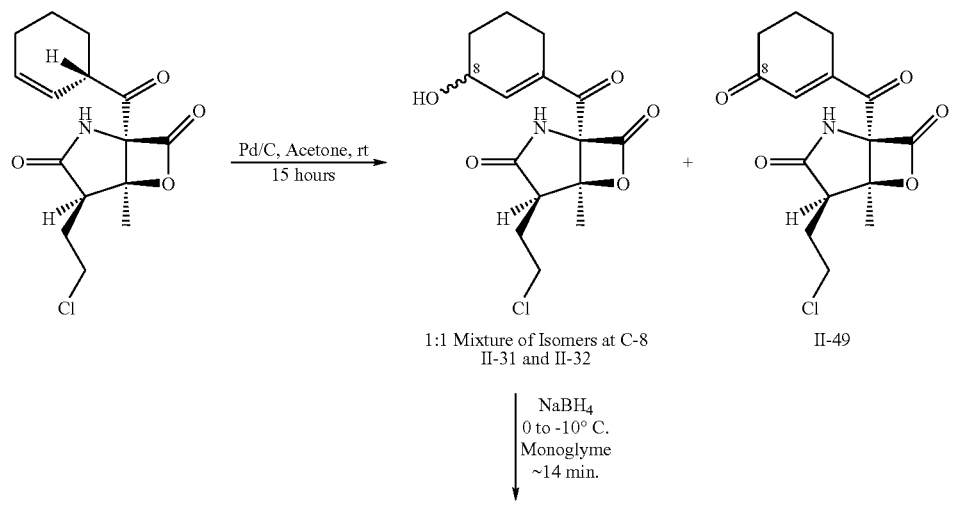

1:1 Mixture of Isomers at C-8
II-31 and II-32

II-49

NaBH₄
0 to -10° C.
Monoglyme
~14 min.

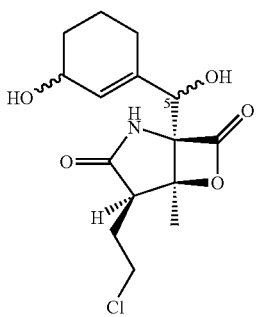

II-33, II-34, II-35 and II-36

Example 14

Synthesis of the Compound of Formula II-21 from II-19

Figure 17:
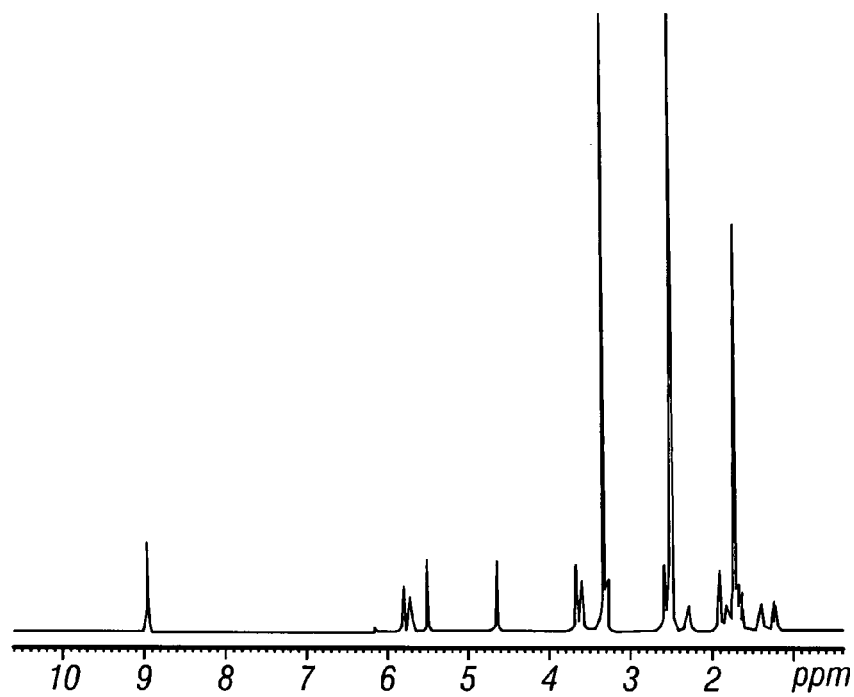
FIG. 17 depicts the $^1$H NMR spectrum of the compound of Formula II-21.

Acetone (7.5 ml) was vigorously mixed with 5 N NaOH (3 ml) and the resulting mixture evaporated to a minimum volume in vacuo. A sample of 100 μl of this solution was mixed with compound of Formula II-19 (6.2 mg) in acetone (1 ml) and the resulting biphasic mixture vortexed for 2 minutes. The reaction solution was immediately subjected to preparative C18 HPLC. Conditions for the purification involved a linear gradient if 10% acetonitrile/90% water to 90% acetonitrile/10% water over 17 minutes using an Ace 5μ C18 HPLC column of dimensions 22 mm id by 150 mm length. Compound of Formula II-21 eluted at 9.1 minutes under these conditions to yield 0.55 mg compound. Compound of Formula II-21: UV (Acetonitrile/H₂O) 225 (sh), ESMS, m/z 296.1 (M+H); ¹H NMR in DMSO-d₆ (see FIG. 17).

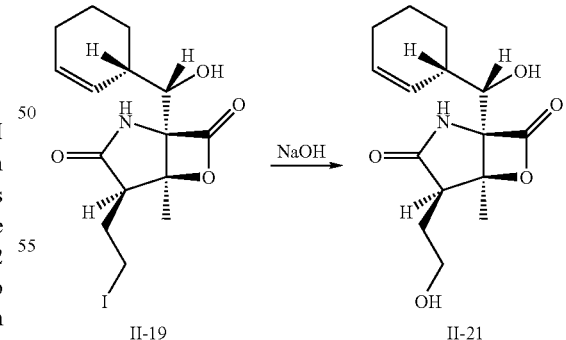

Example 15

Synthesis of the Compound of Formula II-22 from II-19

Figure 18:
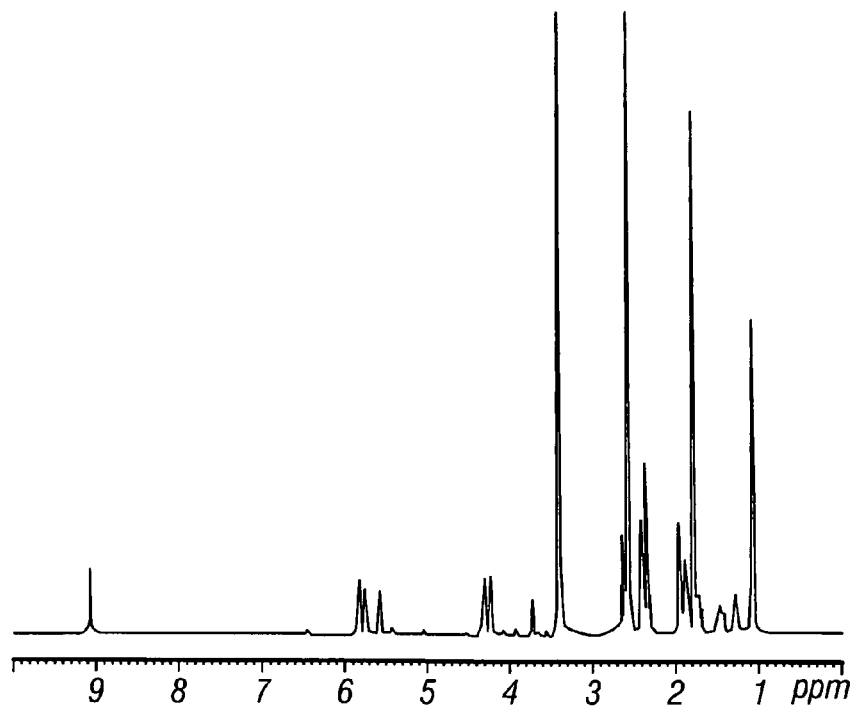
FIG. 18 depicts the $^1$H NMR spectrum of the compound of Formula II-22.

A sample of 60 mg sodium propionate was added to a solution of compound of Formula II-19 (5.3 mg) in DMSO (1 ml) and the mixture sonicated for 5 minutes, though the sodium propionate did not completely dissolve. After 45 minutes, the solution was filtered through a 0.45µ syringe filter and purified directly using HPLC. Conditions for the purification involved a linear gradient if 10% acetonitrile/ 90% water to 90% acetonitrile/10% water over 17 minutes using an Ace 5µ C18 HPLC column of dimensions 22 mm id by 150 mm length. Under these conditions, compound of Formula II-22 eluted at 12.3 minutes to yield 0.7 mg compound (15% isolated yield). UV (Acetonitrile/H$_2$O) 225 (sh), ESMS, m/z 352.2 (M+H); HRMS (ESI), m/z 352.1762 [M+H]$^+$, $\Delta_{calc}$=0.6 ppm, C$_{18}$H$_{26}$NO$_6$; $^1$H NMR in DMSO-d$_6$ (see FIG. 18).

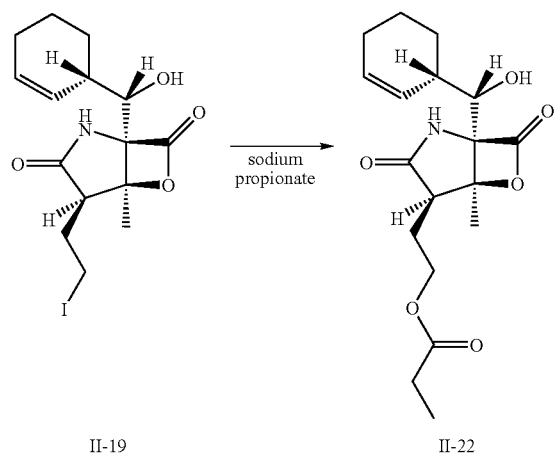

II-19    II-22

Example 16

Synthesis of the Compound of Formula II-29 from II-19

A sample of NaN$_3$ (80 mg) was dissolved in DMSO (1 ml) and transferred to a vial containing Compound II-19 (6.2 mg) which was contaminated with approximately 10% Compound II-16 contaminant at 12.5 minutes (4.2 mg, 85% yield). A 2.4 mg portion of compound II-29 was further purified using additional C18 HPLC chromatography (ACE 5µ C18-HL, 150 mm×21 mm ID) using an isocratic solvent gradient consisting of 35% acetonitrile/65% H$_2$O. Under these conditions compound II-29 eluted after 20 minutes, while Compound II-16 eluted after 21.5 minutes. The resulting sample consisted of 1.1 mg Compound II-29 was used for characterization in biological assays.

Figure 27:
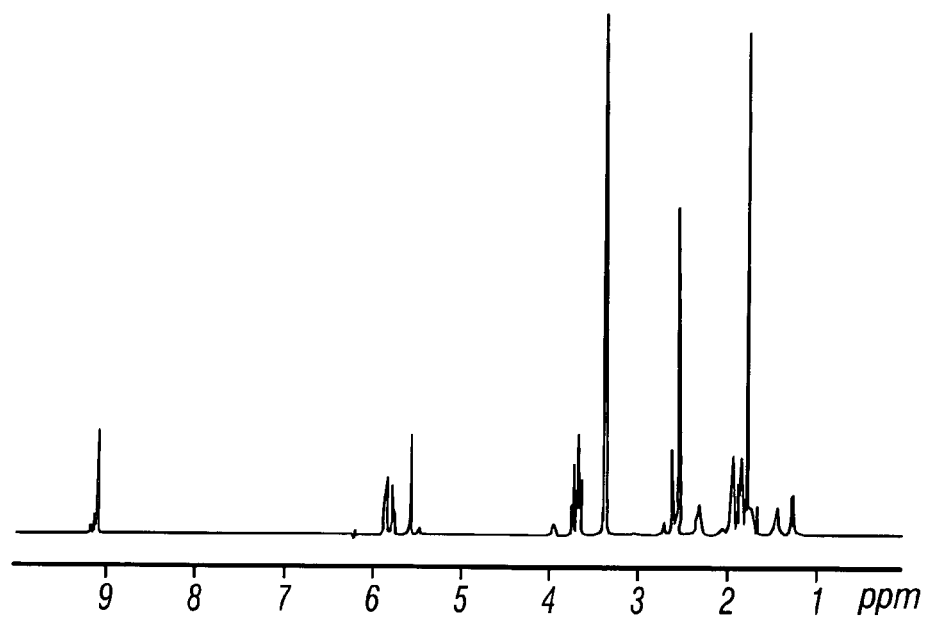
FIG. 27 depicts the $^1$H NMR spectrum of the compound of Formula II-29 in DMSO-$d_6$.

Compound II-29: UV (Acetonitrile/H$_2$O) 225 (sh), ESMS, m/z 321.1 (M+H); $^1$H NMR in DMSO-d$_6$ (see FIG. 27).

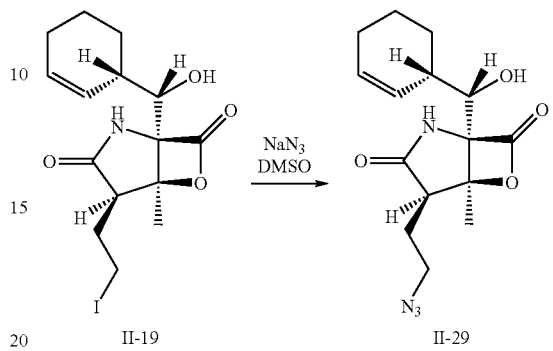

II-19    II-29

Example 17

Synthesis of the Compounds of Formulae II-37 and II-38 from II-19

The compounds of Formulae II-37 and II-38 can be prepared from the compound of Formula II-19 by cyano-de-halogenation or thiocyanato-de-halogenation, respectively. Compound II-19 can be treated with NaCN or KCN to obtain compound II-37. Alternatively, Compound II-19 can be treated with NaSCN or KSCN to obtain compound II-38.

Synthesis of the Compound of Formula II-38 from II-19:

The compound of formula II-19 (10.6 mg, 0.02616 mmol) was dissolved in 1.5 ml of acetone in a scintillation vial (20 ml) to which sodium thiocyanate (10.0 mg, 0.1234 mmol), triethylamine (5 µl, 0.03597 mmol) and a magnetic stir bar were added. The reaction mixture was stirred at room temperature for 72 hours. The reaction mixture was concentrated in vacuo to yield the compound II-38, which was purified by normal phase HPLC using a Phenomenex Luna 10µ Silica column (25 cm×21.2 mm ID) with a solvent gradient of 0 to 95% H$_2$O/Acetonitrile over 21 min, at a flow rate of 14.5 ml/min. Diode array detector was used to monitor the purification process. Compound II-38 (3.0 mg, 34% yield) eluted at 18.0 min as a pure compound. II-38: UV (Acetonitrile/H$_2$O) $\lambda_{max}$ 203 (sh) nm; ESMS m/z 337.1 (M+H)$^+$ & 359.1 (N+Na)$^+$.

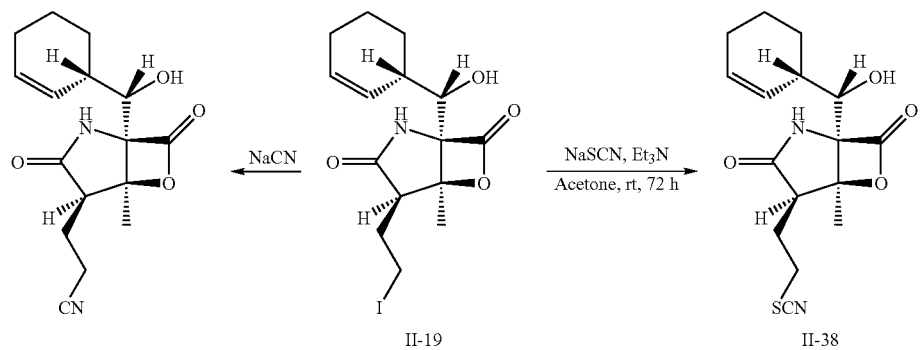

II-19    II-38

Example 18

Synthesis of the Compound of Formula II-39 from II-19

Thiols and thioethers of the Formula II-39 can be formed by dehalogenation of the compound of Formula II-19. Thiols (R=H) can be formed by treatment of Compound II-19 with NaSH, for example, while thioethers (R=alkyl) can be formed by treatment of Compound II-19 with salts of thiols, or alternatively, by treatment with thiols themselves by running the reaction in benzene in the presence of DBU.

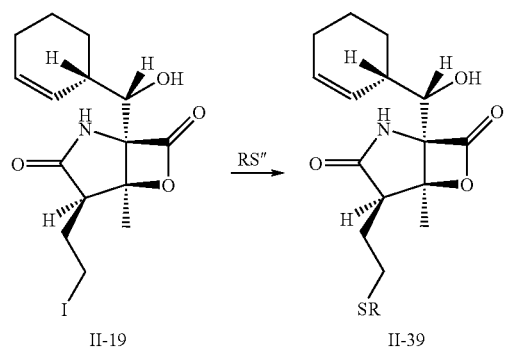

Example 19

Synthesis of the Compound of Formula II-40 from II-39

Sulfoxides (n=1) and sulfones (n=2) of the Formula II-40 can be formed by oxidation of thioethers of the Formula II-39, for example, with hydrogen peroxide or other oxidizing agents.

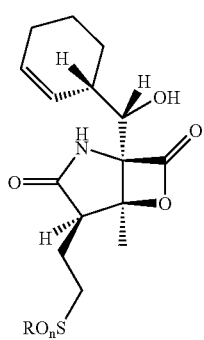

II-40

Example 20

Synthesis of the Compound of Formula II-41 from II-21

The compound of the Formula II-41 can be prepared by treatment of the compound of Formula II-21 (or a protected derivative of II-21, where the C-5 alcohol or lactam NH are protected, for example) with methyl sulfonyl chloride (mesyl chloride) in pyridine, for example, or by treatment with mesyl chloride in the presence of triethylaminde. Other sulfonate esters can be similarly prepared.

Example 21

Synthesis of the Compound of Formula II-46 from II-19 or II-41

The alkene of the Formula II-46 can be prepared by dehydroiodination of the compound of Formula II-19, or by hydro-mesyloxy elimination of the compound of Formula II-41, for example, by treatment with base.

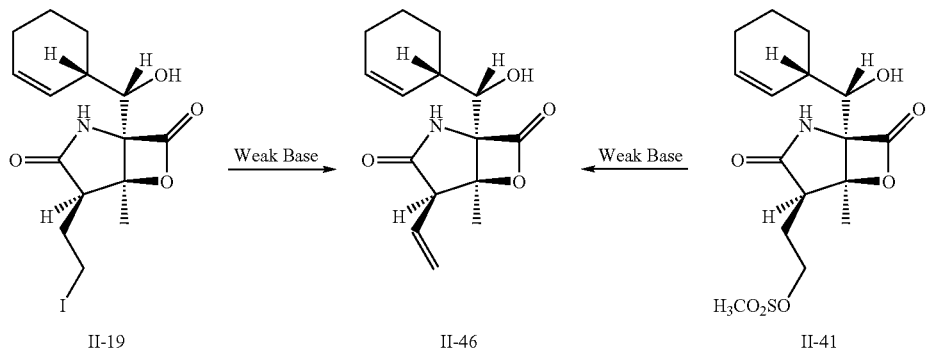

Example 22

Synthesis of the Compound of Formula II-42A

Synthesis of boronic acids or esters, for example, the compound of the Formula II-42A, can be achieved as outlined in the retrosynthetic scheme below. Hydroboration of the alkene of Formula II-46 gives the corresponding alkyl borane, which can be converted to the corresponding boronic acid or ester, for example, the compound of the Formula II-42A.

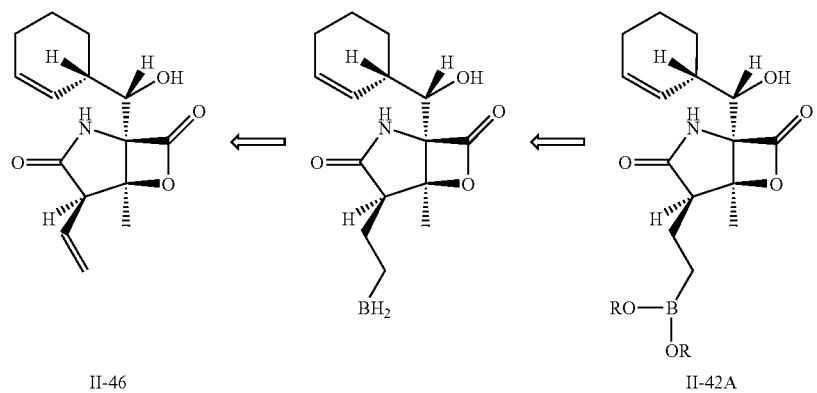

II-46                II-42A

Example 23

Synthesis of the Compound of Formula II-43A

The compound of the Formula II-43A can be prepared by treatment of the compound of Formula II-19 with triphenyl phosphine to make a phosphorus ylide, which can be treated with various aldehydes, for example, glyoxylic acid methyl ester, to make Formula II-43A.

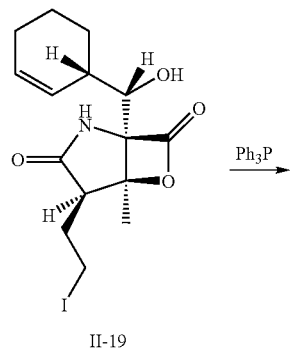

II-19

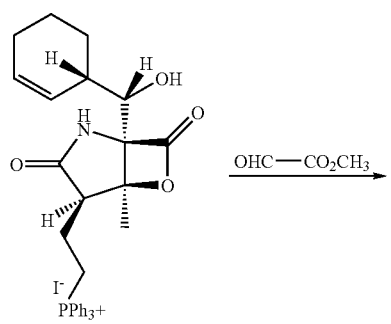

-continued

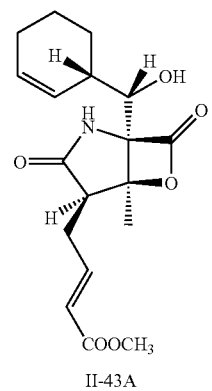

II-43A

Example 24

Synthesis of the Compound of Formula II-30 from II-19

A portion of CuI (100 mg) was placed in a 25 ml pear bottom flask and flushed with Ar gas for 30 minutes and Ar gas flow was maintained through the flask throughout the course of the reaction. The vessel was cooled to −78° C. prior to addition of dry THF (5 ml) followed by the immediate dropwise addition of a solution of methyllithium in dry THF (5.0 ml, 1.6 M) with vigorous stirring. A solution of Compound II-19 in dry THF (12 mg Compound II-19, 1 ml THF) was added slowly to the clear dialkylcuprate solution and the resulting mixture stirred at −78° C. for 1 hr. The reaction was quenched by washing the THF solution through a plug of silica gel (1 cm diameter by 2 cm length) along with further washing using a solution of 50% EtOAc/ 50% hexanes (50 ml). The combined silica plug washes were dried in vacuo and subjected to further C18 HPLC purification in 2 injections (ACE 5μ C18-HL, 150 mm×21 mm ID) using an isocratic solvent gradient consisting of 35% ACN/65% $H_2O$. Compound II-30 eluted under these conditions at 23.5 minutes and yielded 2.4 mg material (27% isolated yield) at 90.8% purity as measured by analytical HPLC. An alternative normal phase purification method can be utilized using a Phenomenex Luna 10μ Silica column (25 cm×21.2 mm ID) with a solvent gradient consisting of 100% hexanes/ethyl acetate to 0% hexanes over 20 minutes. Compound II-30 eluted under these conditions at 16.5 minutes and yielded 3.0 mg material (41% isolated yield) at 97.1% purity measured by analytical HPLC.

Figure 28:
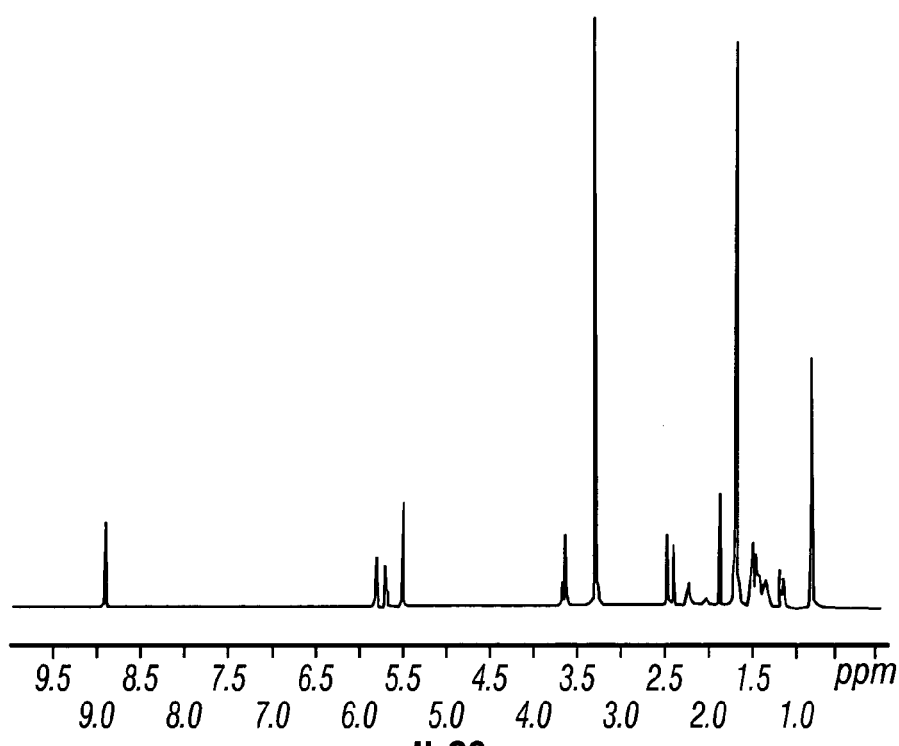
FIG. 28 depicts the $^1$H NMR spectrum of the compound of Formula II-30 in DMSO-$d_6$.
Figure 29:
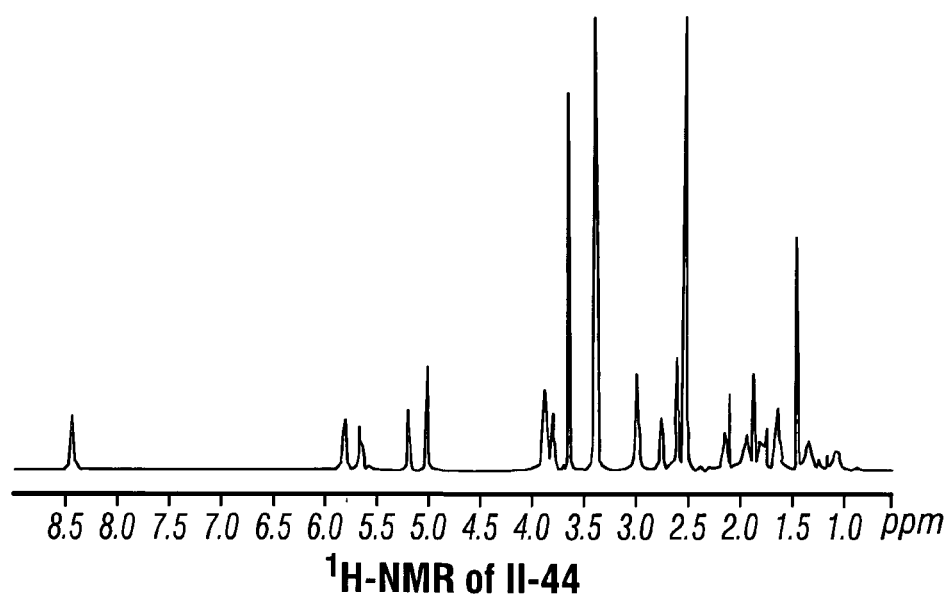
FIG. 29 depicts the $^1$H NMR spectrum of the compound of Formula II-44 in DMSO-$d_6$.

Compound II-30: UV (Acetonitrile/H$_2$O) 225 (sh), ESMS, m/z 294.1 (M+H); HRMS (ESI), m/z 294.1696 [M+H]$^+$, $\Delta_{calc}$=-3.2 ppm, C$_{16}$H$_{24}$NO$_4$; $^1$H NMR in DMSO-d$_6$ (see FIG. 28).

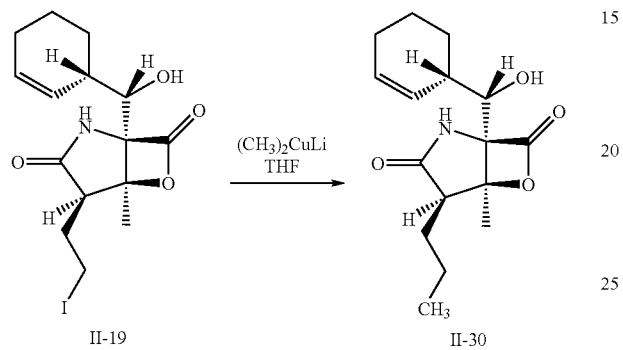

II-19      II-30

Example 25

Synthesis of the Compound of Formulae II-44 and VI-1A from II-16

The compound of Formula II-16 (30 mg, 0.096 mmol) was dissolved in CH$_2$Cl$_2$ (9 ml) in a scintillation vial (20 ml) to which triethylamine (40 μl, 0.29 mmol), methyl-3-mercapto propionate (thiol, 250 μl) and a magnetic stir bar were added. The reaction mixture was stirred at room temperature for about 4 hours. The solvent was evaporated from the reaction mixture to yield a mixture of compounds of Formulae II-44 and VI-1A (19:1), which were separated by reversed phase HPLC using Ace 5u C18 column (150 mm×22 mm ID) with a solvent gradient of 35% to 90% H$_2$O/Acetonitrile over 17 min, 90 to 100% Acetonitrile over1 min, holding at 100% Acetonitrile for 1 min, at a flow rate of 14.5 ml/min. Diode array detector was used to monitor the purification process. Compounds II-44 (20 mg) and VI-1A (1 mg) eluted at 11.68 and 10.88 min, respectively, as pure compounds. Compound II-44: UV (Acetonitrile/H$_2$O) $\lambda_{max}$ 240 (sh) nm; ESMS m/z 434.0 (M+H)$^+$ & 456.0 (M+Na)$^+$. Compound VI-1A: UV (Acetonitrile/H$_2$O) $\lambda_{max}$ 220 (sh) nm; ESMS, m/z 398.0 (M+H)$^+$ & 420.0 (M+Na)$^+$.

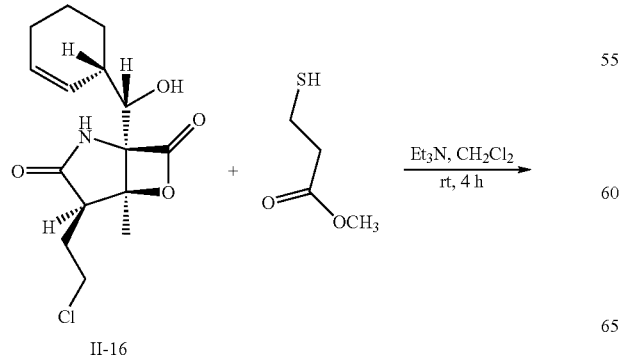

II-16

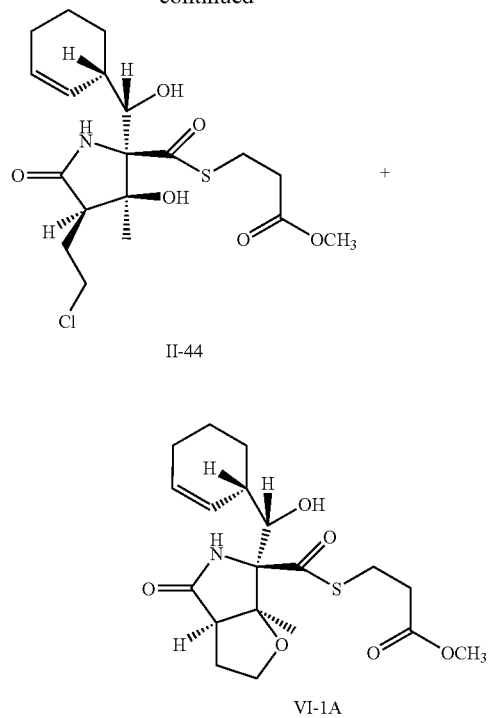

II-44

VI-1A

Example 26

Oxidation of Secondary Hydroxyl Group in Starting Compounds and Reaction with Hydroxy or Methoxy Amines The secondary hydroxyl group in the Starting Compounds is oxidized using either of the following reagents: pyridinium dichromate (PDC), pyridinium chlorochromate (PCC), Dess-Martin periodinane or oxalyl chloride (Swern oxidation) (Ref: Organic Syntheses, collective volumes I-VII). Preferably, Dess-Martin periodinane can be used as a reagent for this reaction. (Ref: Fenteany G. et al. Science, 1995, 268, 726-73). The resulting keto compound is treated with hydroxylamine or methoxy amine to generate oximes.

Examples

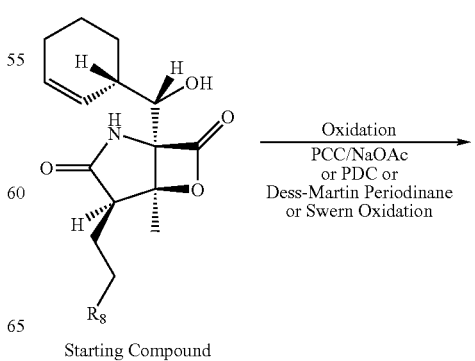

Starting Compound

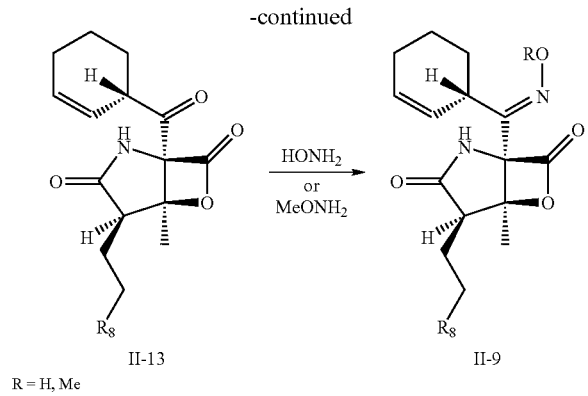

Example 27

Reductive Amination of Keto-derivative of Starting Compounds

The keto derivatives are treated with sodium cyanoborohydride (NaBH$_3$CN) in the presence of various bases to yield amine derivatives of the Starting Compounds, which are subsequently hydrogenated with 10% Pd/C, H$_2$ to reduce double bond in cyclohexene ring.

Example

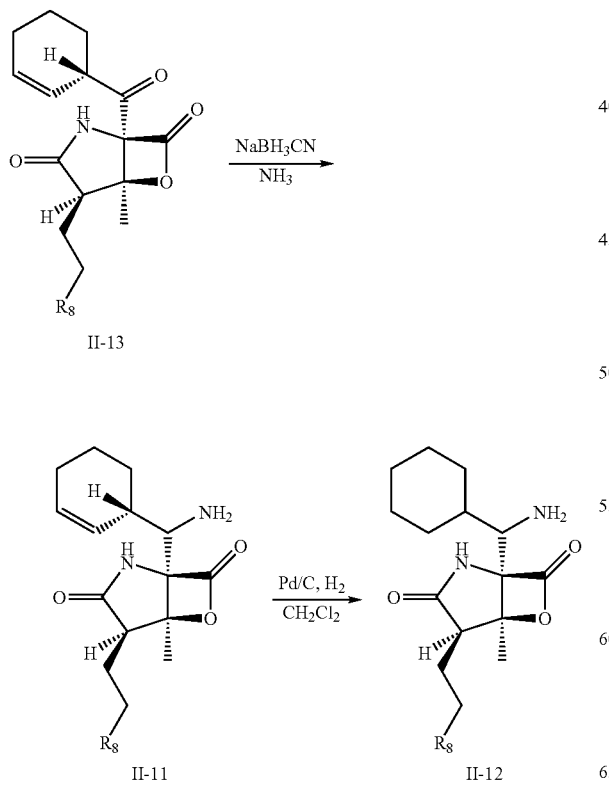

Example 28

Cyclohexene Ring Opening

The Starting Compounds can be protected, for example, at the alcohol and/or at the lactam nitrogen positions, and treated with OsO$_4$ and NaIO$_4$ in THF-H$_2$O solution to yield dial derivatives which are reduced to the alcohol with NaBH$_4$. The protecting groups can be removed at the appropriate stage of the reaction sequence to produce II-7 or II-6.

Example

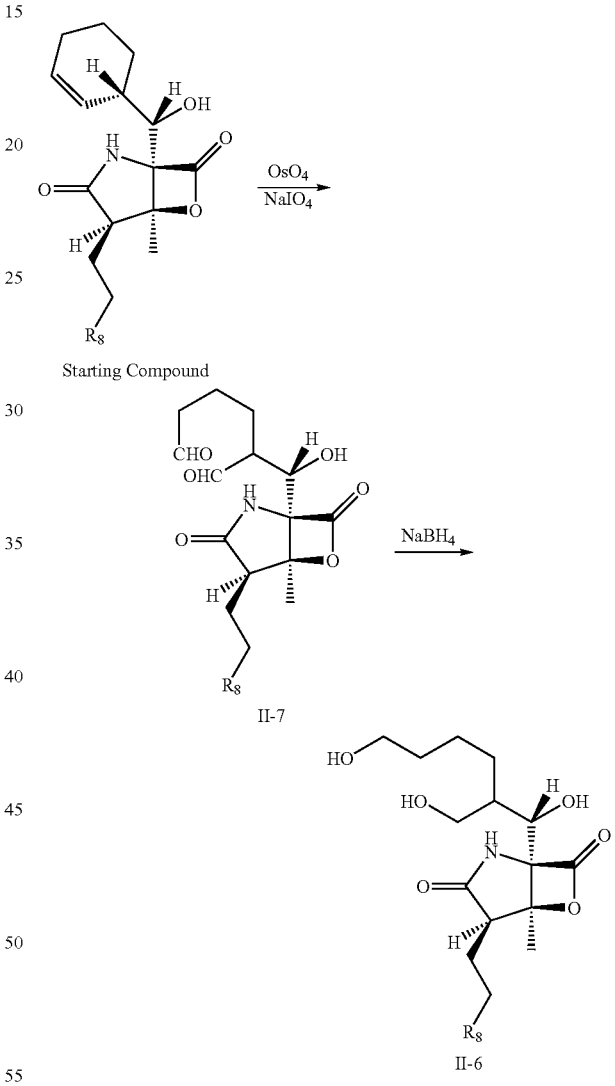

Example 29

Dehydration of Alcohol Followed by Aldehyde Formation at Lactone-lactam Ring Junction A Starting Compound is dehydrated, for example, by treatment with mesylchloride in the presence of base, or, for example, by treatment with Burgess reagent or other dehydrating agents,. The resulting dehydrated compound is treated with OsO$_4$, followed by NaIO$_4$, or alternatively by ozonolysis, to yield an aldehyde group at the lactone-lactam ring junction.

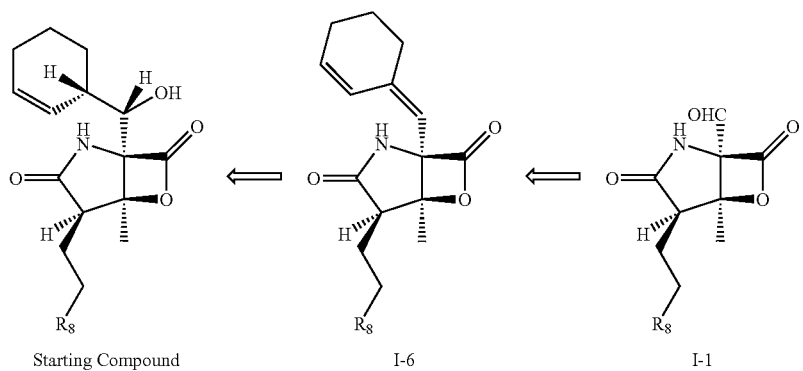

Example 30

Oxidation of the Cyclohexene Ring to Produce Cyclohexadienes or a Phenyl Ring A Starting Compound, such as the ketone of Formula II-13C, is treated with Pd/C to produce a cyclohexadiene derivative. The new double bond can be at any position of the cyclohexene ring. The ketone can be reduced, for example, with sodium borohydride, to obtain the corresponding secondary alcohol(s). Alternatively, the cyclohexadiene derivative can be further treated, for example with DDQ, to aromatize the ring to a phenyl group. Similarly, the ketone can be reduced, for example, with sodium borohydride, to obtain the corresponding secondary alcohol(s).

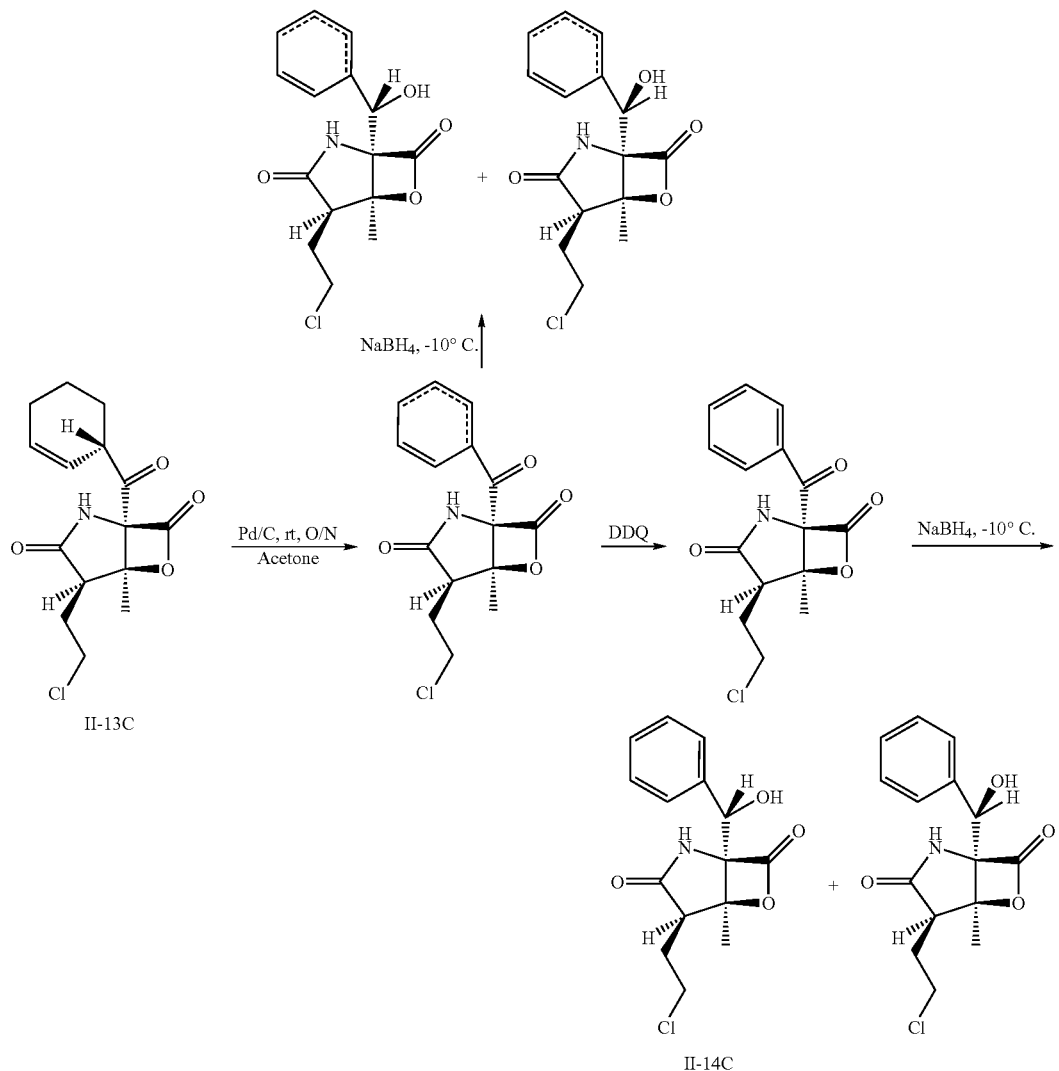

As an alternate method, the starting compound, such as the compound of Formula II-49, can be treated, for example with TMSCl to produce cyclohexadiene derivative. The cyclohexadiene derivative can be further treated, for example with DDQ, to aromatize the ring to a phenyl group. The OTMS on the phenyl group can be removed, for example, with acid or base. Similarly, the ketone can be reduced, for example, with sodium borohydride, to obtain the corresponding secondary alcohol(s).

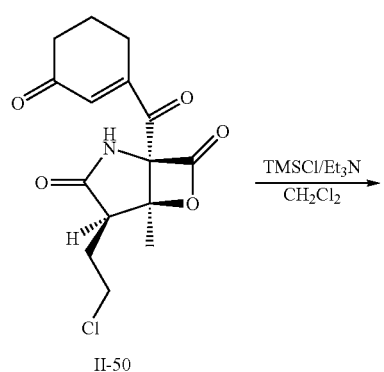

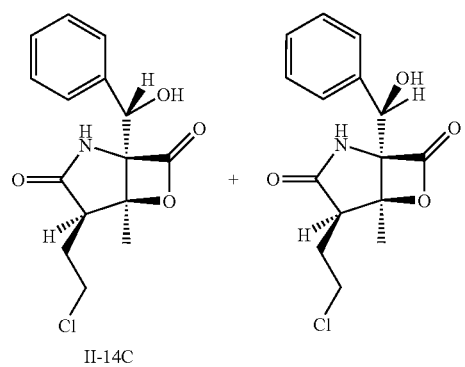

II-14C

Example 31

Various Reactions on Aldehyde Derivatives

Wittig reactions are performed on the aldehyde group of I-1 using various phosphorus ylides [e.g., (triphenylphosphoranylidene)ethane] to yield an olefin. The double bond in the side chain is reduced by catalytic hydrogenation.

Example

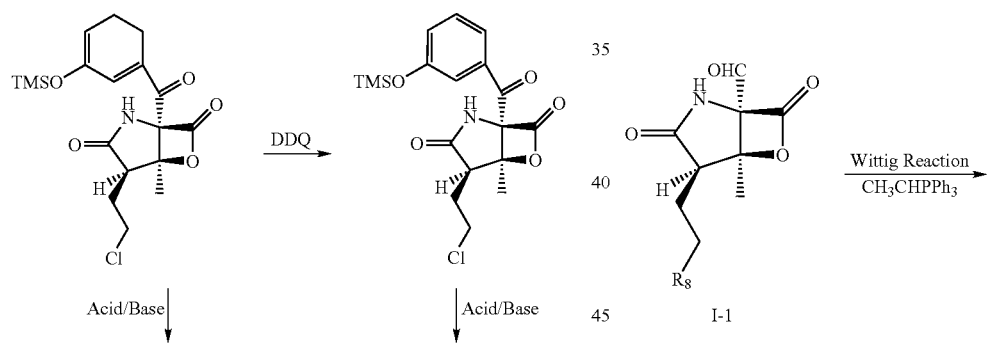

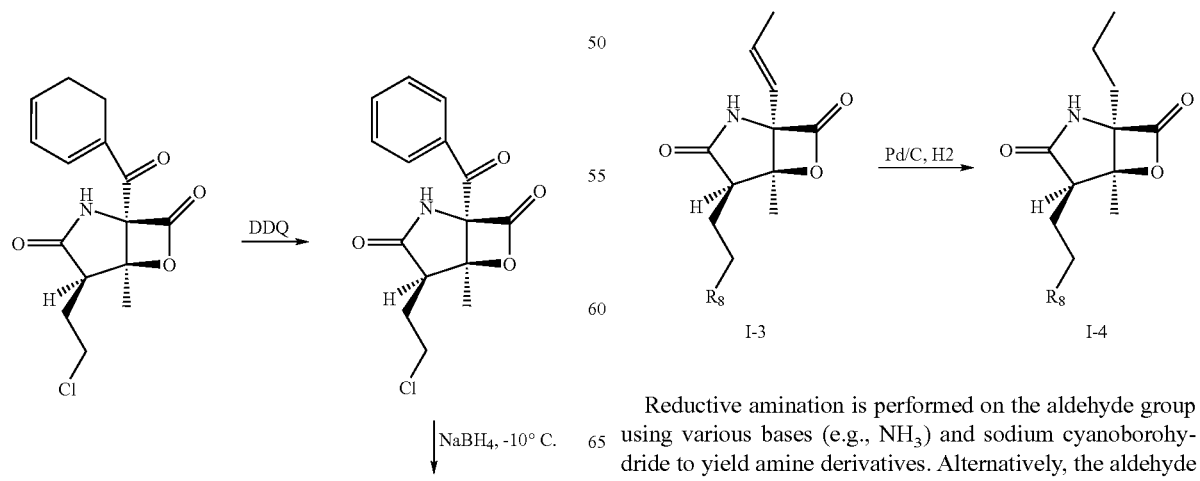

Reductive amination is performed on the aldehyde group using various bases (e.g., $NH_3$) and sodium cyanoborohydride to yield amine derivatives. Alternatively, the aldehyde is reduced with $NaBH_4$ to form alcohols in the side chain.

Example
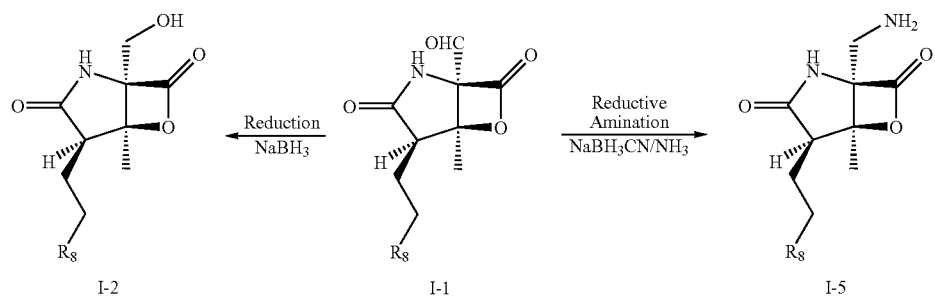
Organometallic addition reactions to the aldehyde carbonyl can be performed to yield various substituted secondary alcohols. Examples:
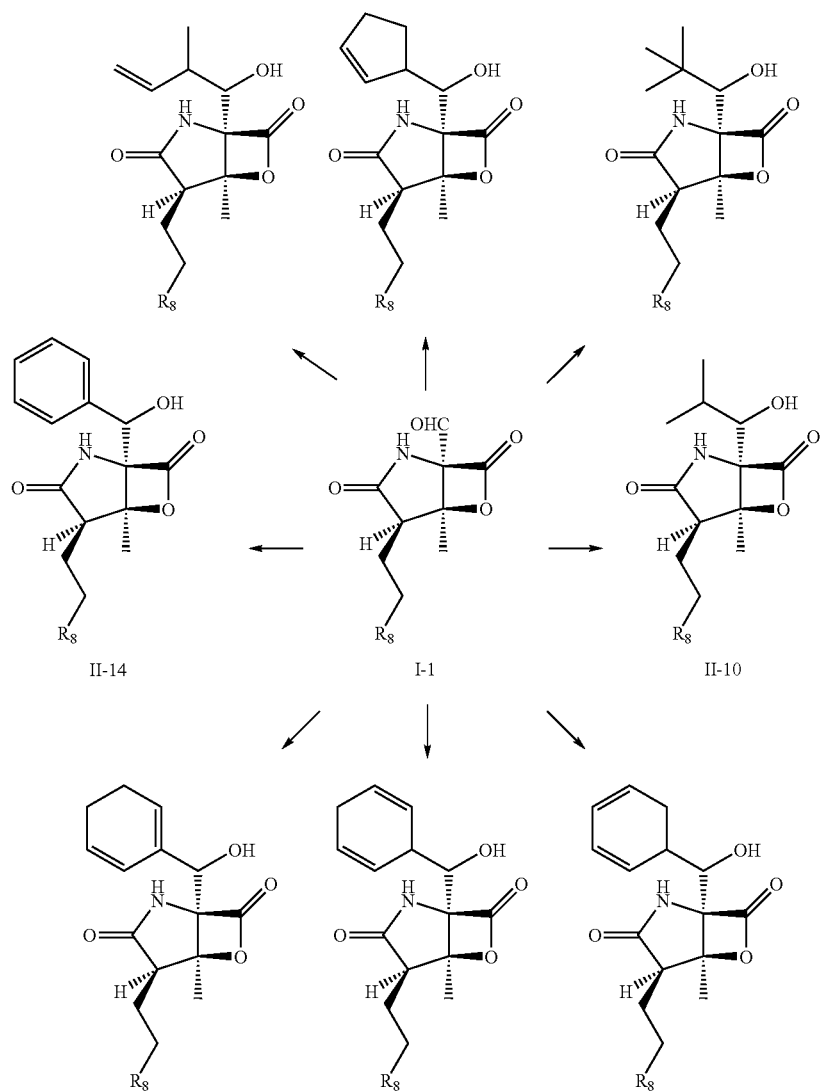

Example 32

Synthesis of the Compound of Formula II-47 from II17

The compound of Formula II-17 (25 mg, 0.0896 mmol) was dissolved in $CH_2Cl_2$ (9 ml) in a scintillation vial (20 ml) to which triethylamine (38 µl, 0.27 mmol), methyl-3-mercapto propionate (thiol, 250 µl) and a magnetic stir bar were added. The reaction mixture was stirred at room temperature for about 4 hours. The solvent was evaporated from the reaction mixture to yield the compound of Formulae II-47, which was further purified by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process. Compound II-47 (15 mg) eluted at 10.98 min as pure compound. Compound II-47: UV (Acetonitrile/$H_2O$) $\lambda_{max}$ 240 (sh) nm; ESMS m/z 400.1 $(M+H)^+$ & 422.1 $(M+Na)^+$.

Example 33

Synthesis of the Compound of Formulae II-48 and VI-1B from II-16

The compound of Formula II-16 (15 mg, 0.048 mmol) was dissolved in 1:1 ratio of ACN/DMSO (8 ml) in a scintillation vial (20 ml) to which triethylamine (40 µl, 0.29 mmol), Glutathione (44.2 mg, 0.144 mmol) and a magnetic stir bar were added. The reaction mixture was stirred at room temperature for about 3 hours. The solvent was evaporated from the reaction mixture to yield the compound of Formula II-48, which was purified by reversed phase HPLC using Ace 5u C18 column (150 mm×22 mm ID) with a solvent gradient of 10% to 70% $H_2O$/Acetonitrile over 15 min, 70 to 100% Acetonitrile over 5 min, holding at 100% Acetonitrile for 4 min, at a flow rate of 14.5 ml/min. Diode array detector was used to monitor the purification process. Compound II-48 (10 mg) eluted as a pure compound at 8.255 min. Compound II-48: UV (Acetonitrile/$H_2O$) $\lambda_{max}$ 235 (sh) nm; ESMS m/z 621.0 $(M+H)^+$. Compound II-48 was unstable in solution and converted to compound VI-1B which appeared as a mixture of II-48 and VI-1B in the ratio of 7:3. Compound VI-1B: WV (Acetonitrile/$H_2O$) $\lambda_{max}$ 235 (sh) nm; ESMS, m/z 585.2 $(M+H)^+$.

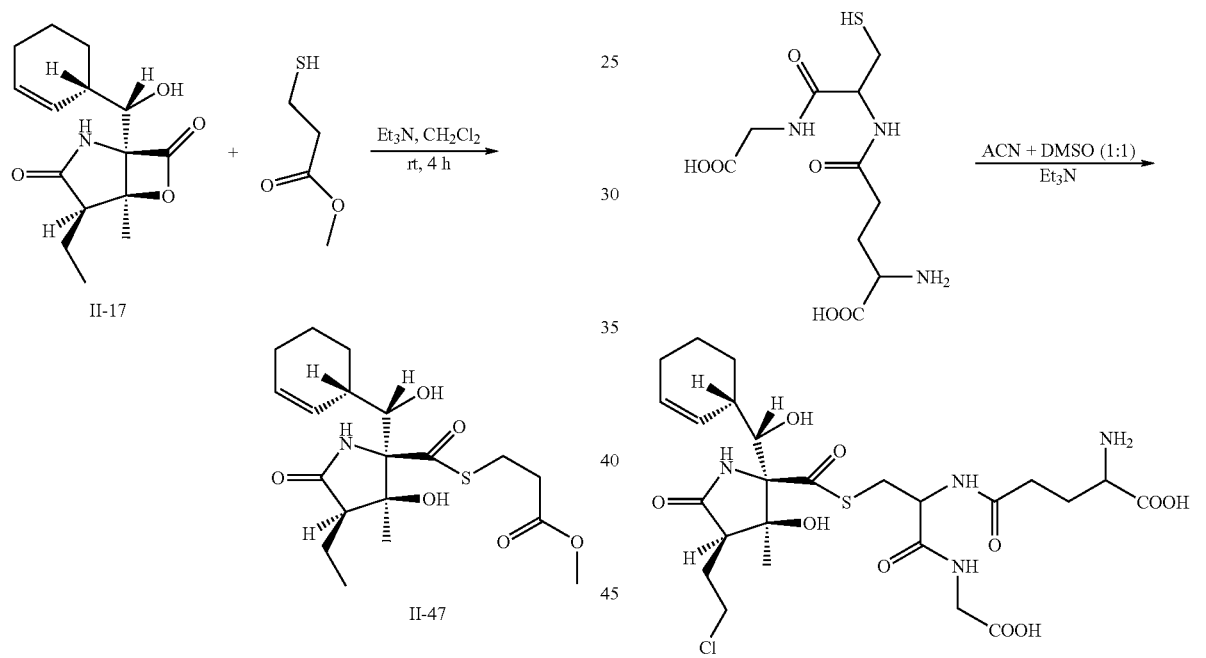
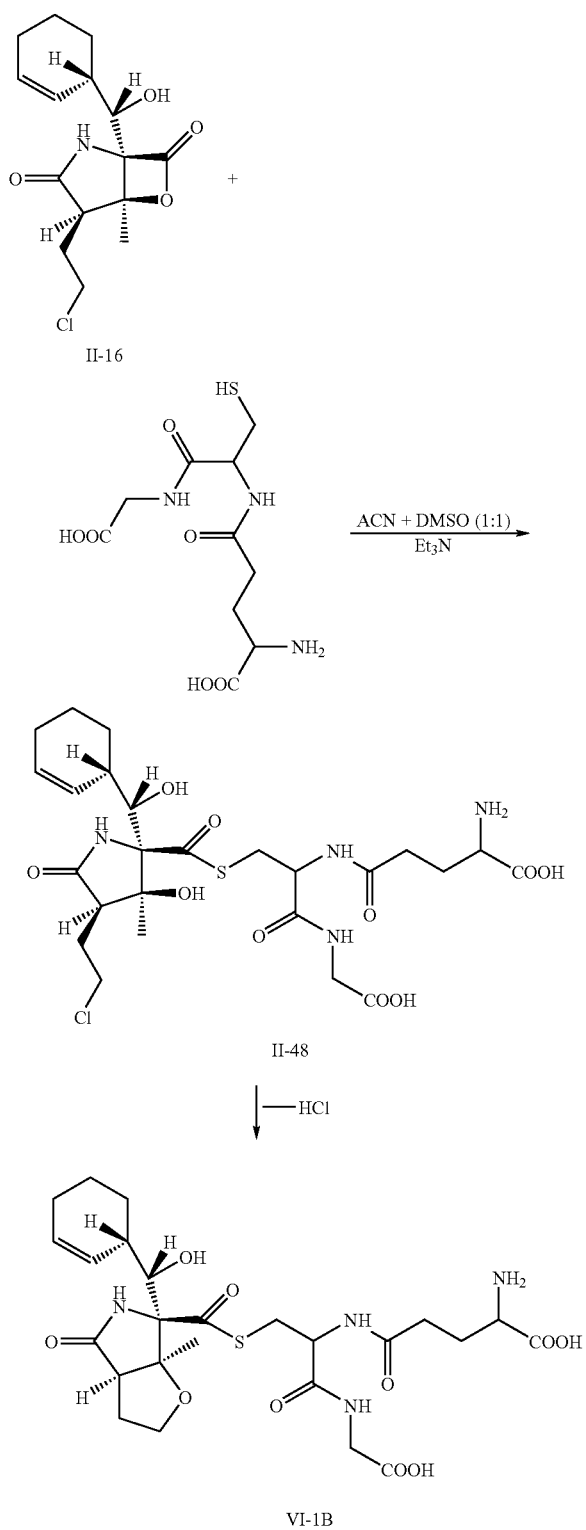

Example 34

Synthesis of the Compound of Formula II-50 and VI-1C from II-16

The compound of Formula II-16 (10 mg, 0.032 mmol) was dissolved in CH$_2$Cl$_2$ (9 ml) in scintillation vial (20 ml) to which triethylamine (26.5 µl, 0.192 mmol), N-Acetyl-L-Cysteine methyl ester (17 mg, 0.096 mmol) and a magnetic stir bar were added. The reaction mixture was stirred at room temperature for about 4 hours. The solvent was evaporated from the reaction mixture to yield the mixture of compounds of Formulae II-50 and VI-1C, which were further purified by normal phase HPLC using Phenomenex Luna 10u Silica column (25 cm×21.2 mm ID) with a solvent gradient of 10% to 100% Hexane/EtOAc over 24 min, holding at 100% EtOAc for 3 min, at a flow rate of 14.5 ml/min. ELSD was used to monitor the purification process. Compounds II-50 (2 mg) and VI-1C (0.2 mg) were eluted at 10.39 and 10.57 min, respectively as pure compounds. Compound II-50: UV (Acetonitrile/H$_2$O) $\lambda_{max}$ 230 (sh) nm; ESMS m/z 491.1 (M+H)$^+$ & 513.0 (M+Na)$^+$. Compound VI-1C: UV (Acetonitrile/H$_2$O) $\lambda_{max}$ 215 (sh) nm; ESMS m/z 455.1 (M+H)$^+$ & 577.0 (M+Na)$^+$

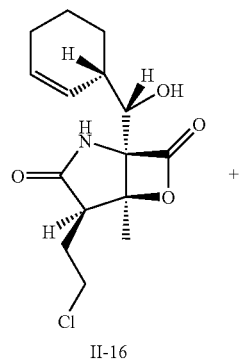

II-16

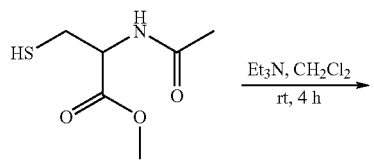

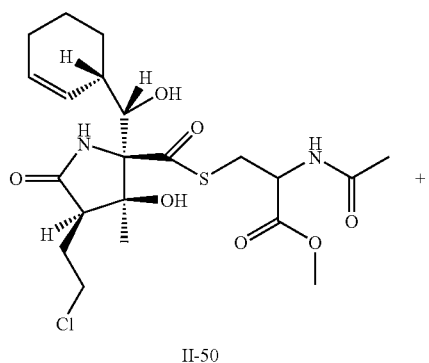

II-50

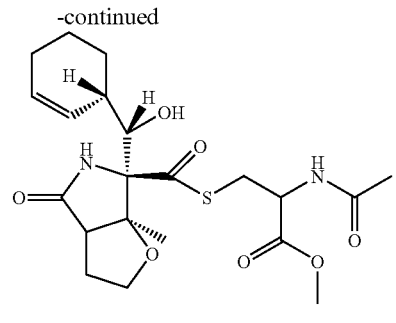

VI-1C

Example 35

Growth Inhibition of Colon, Prostate, Breast, Lung, Ovarian, Multiple Myeloma and Melanoma Human colon adenocarcinoma (HT-29; HTB-38), prostate adenocarcinoma (PC-3; CRL-1435), breast adenocarcinoma (MDA-MB-231; HTB-26), non-small cell lung carcinoma (NCI-H292; CRL-1848), ovarian adenocarcinoma (OVCAR-3; HTB-161), multiple myeloma (RPMI 8226; CCL-155), multiple myeloma (U266; TIB-196) and mouse melanoma (B16-F10; CRL-6475) cells were all purchased from ATCC and maintained in appropriate culture media. The cells were cultured in an incubator at 37° C. in 5% CO$_2$ and 95% humidified air.

For cell growth inhibition assays, HT-29, PC-3, MDA-MB-231, NCI-H292, OVCAR-3 and B16-F10 cells were seeded at 5×10$^3$, 5×10$^3$, 1×10$^4$, 4×10$^3$, 1×10$^4$ and 1.25×10$^3$ cells/well respectively in 90 µl complete media into 96 well (Corning; 3904) black-walled, clear-bottom tissue culture plates and the plates were incubated overnight to allow cells to establish and enter log phase growth. RPMI 8226 and U266 cells were seeded at 2×10$^4$ and 2.5×10$^4$ cells/well respectively in 90 µl complete media into 96 well plates on the day of the assay. 20 mM stock solutions of the compounds were prepared in 100% DMSO and stored at −80° C. The compounds were serially diluted and added in triplicate to the test wells. Concentrations ranging from 6.32 µM to 632 µM were tested for II-2 and II-4. II-3 was tested at concentrations ranging from 20 µM to 6.32 nM. Formulae II-18 and II-19 were tested at concentrations ranging from 2 µM to 200 pM. Formula II-5A and Formula II-5B were tested at final concentrations ranging from 2 µM to 632 µM and 20 µM to 6.32 nM respectively. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in Mg$^{2+}$, Ca$^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and EC$_{50}$ values (the drug concentration at which 50% of the maximal observed growth inhibition is established) were determined using a standard sigmoidal dose response curve fitting algorithm (XLfit 3.0, ID Business Solutions Ltd). Where the maximum inhibition of cell growth was less than 50%, an $EC_{50}$ value was not determined.

The data in Table 1 summarize the growth inhibitory effects of Formulae II-2, II-3, II-4, II-5A, II-5B, II-18 and II-19 against the human colorectal carcinoma, HT-29, human prostate carcinoma, PC-3, human breast adenocarcinoma, MDA-MB-231, human non-small cell lung carcinoma, NCI-H292, human ovarian carcinoma, OVCAR-3, human multiple rmyelomas, RPMI 8226 and U266 and murine melanoma B16-F10 cell lines.

II-19, II-44 and II-50 ranged from 632 nM to 200 pM. The final concentration range of Formula II-2, II-4 and II-5A were from 2 μM to 632 μM. The final concentration of DMSO was 0.25% in all samples.

Following 48 hours of drug exposure, 10 μl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the back-

TABLE 1

$EC_{50}$ values of Formulae II-2, II-3, II-4, II-5A, II-5B, II-18 and II-19 against various tumor cell lines

| Cell line | $EC_{50}$ (nM)* | | | | | | |
|---|---|---|---|---|---|---|---|
| | II-2 | II-3 | II-4 | II-5A | II-5B | II-18 | II-19 |
| HT-29 | 129 ± 21 | >20000 | 132 ± 36 | 67 ± 17 | 1070 | 18 ± 7.8 | 11 ± 1.6 |
| | | | | | 1210 | | |
| PC-3 | 284 ± 110 | >20000 | 204 ± 49 | 109 ± 15 | 1330 | 35 ± 5.6 | 29 ± 4.0 |
| | | | | | 1790 | | |
| MDA-MB-231 | 121 ± 23 | >20000 | 114 ± 4 | 61 ± 4.6 | 1040 | 16 ± 2.8 | 14 ± 3.2 |
| | | | | | 957 | | |
| NCI-H292 | 322 | >20000 | 192 | 102 ± 19 | 992 | 29 | 27 ± 3.8 |
| | 395 | >20000 | 213 | | 1250 | 41 | |
| OVCAR-3 | 188 | >20000 | >6320 | 80 | 1320 | >2000 | 24 |
| | 251 | | >6320 | 64 | | >2000 | 20 |
| RPMI 8226 | 49 | >20000 | 57 | 36 | 326 | 6.3 | 5.9 |
| | 45 | >20000 | 51 | 29 | 328 | 6.3 | 7.1 |
| U266 | 39 | >20000 | 39 | 10 | 118 | 4.2 | 3.2 |
| | 32 | >20000 | 34 | 9 | 111 | 4.2 | 3.4 |
| B16-F10 | 194 | >20000 | 163 | 78 ± 11 | 1270 | 19 | 13 ± 1.9 |
| | 180 | >20000 | 175 | | 1140 | 36 | |

*Where n ≥ 3, mean ± standard deviation is presented

The $EC_{50}$ values indicate that the Formulae II-2, II-4, II-5A, II-5B, II-18 and II-19 were cytotoxic against the HT-29, PC-3, MDA-MB-231, NCI-H292, RPMI 8226, U266 and B16-F10 tumor cell lines. II-2, II-5A, II-5B and II-19 were also cytotoxic against the OVCAR-3 tumor cells.

Example 36

Growth Inhibition of Human Multiple Myeloma by Formulae I-7, II-2, II-3, II-4, II-5A, II-5B, II-8C, II-13C, II-18, II-19, II-20, II-21, II-22, II-24C, II-25, II-26, II-28, II-29, II-30, II-31, II-32, II-38, IV-3C, II-44, VI-1A, II-47 and II-50; RPMI 8226 and U266 Cells The human multiple myeloma cell lines, RPMI 8226 (ATCC; CCL-155) and U266 (ATCC; TIB-196) were maintained in appropriate culture media. The cells were cultured in an incubator at 37° C. in 5% $CO_2$ and 95% humidified air.

For cell growth inhibition assays, RPMI 8226 cells and U266 were seeded at $2\times10^4$ and $2.5\times10^4$ cells/well respectively in 90 μl complete media into Corning 3904 black-walled, clear-bottom tissue culture plates. 20 mM stock solutions of the compounds were prepared in 100% DMSO, aliquoted and stored at −80° C. The compounds were serially diluted and added in triplicate to the test wells. The final concentration range of Formula I-7, II3, II-8C, II-5B, II-13C, II-20, II-21, II-22, II-24C, II-25, II-26, II-28, II-29, II-30, II-31, II-32, II-38, IV-3C, VI-1A and II-47 were from 20 μM to 6.32 nM. The final concentration of Formula II-18, ground, which was subtracted from the data for all experimental wells. The data were normalized to the average fluorescence of the cells treated with media +0.25% DMSO (100% cell growth) and $EC_{50}$ values (the drug concentration at which 50% of the maximal observed growth inhibition is established) were determined using a standard sigmoidal dose response curve fitting algorithm (generated by XLfit 3.0 or XLfit 4.0, ID Business Solutions Ltd).

The data in Table 2 summarize the growth inhibitory effects of Formulae I-7, II-2, II-3, II-4, II-5A, II-5B, II-8C, II-13C, II-18, II-19, II-20, II-21, II-22, II-24C, II-25, II-26, II-28, II-29, II-30, II-31, II-32, II-38, IV-3C, II-44, VI-1A, II-47, and II-50 against human multiple myeloma cell lines, RPMI 8226 and U266.

TABLE 2

$EC_{50}$ values of Formulae I-7, II-2, II-3, II-4, II-5A, II-5B, II-8C, II-13C, II-18, II-19, II-20, II-21, II-22, II-24C, II-25, II-26, II-28, II-29, II-30, II-31, II-32, II-38, IV-3C, II-44, VI-1A, II-47 and II-50 against RPMI 8226 and U266 cells

| Compound | RPMI 8226 $EC_{50}$ (nM) | U266 $EC_{50}$ (nM) |
|---|---|---|
| Formula I-7 | 250 | ND |
| | 240 | |
| Formula II-2 | 49 | 39 |
| | 45 | 32 |
| Formula II-3 | >20000 | >20000 |
| | >20000 | >20000 |

TABLE 2-continued

EC$_{50}$ values of Formulae I-7, II-2, II-3, II-4, II-5A, II-5B, II-8C, II-13C, II-18, II-19, II-20, II-21, II-22, II-24C, II-25, II-26, II-28, II-29, II-30, II-31, II-32, II-38, IV-3C, II-44, VI-1A, II-47 and II-50 against RPMI 8226 and U266 cells

| Compound | RPMI 8226 EC$_{50}$ (nM) | U266 EC$_{50}$ (nM) |
|---|---|---|
| Formula II-4 | 57 | 39 |
|  | 51 | 34 |
| Formula II-5A | 36 | 10 |
|  | 29 | 9 |
| Formula II-5B | 326 | 118 |
|  | 328 | 111 |
| Formula II-8C | >20000 | >20000 |
|  | >20000 | >20000 |
| Formula II-13C | >20000 | >20000 |
|  | >20000 | >20000 |
| Formula II-18 | 6.3 | 4.2 |
|  | 6.3 | 4.2 |
| Formula II-19 | 5.9 | 3.2 |
|  | 7.1 | 3.4 |
| Formula II-20 | 8510 ± 3260 | 310 |
|  |  | 442 |
| Formula II-21 | >20000 | 6090 |
|  | >20000 | 9670 |
| Formula II-22 | 9720 | 2860 |
|  | 11200 | 903 |
| Formula II-24C | 2320 | 1150 |
|  | 1640 | 825 |
| Formula II-25 | >20000 | >20000 |
|  | >20000 | >20000 |
| Formula II-26 | 2230 | 1300 |
|  | 1610 | 829 |
| Formula II-28 | >20000 | >20000 |
|  | >20000 | >20000 |
| Formula II-29 | 4280 | 624 |
|  | 6940 | 1420 |
| Formula II-30 | 4900 | 889 |
|  | 4160 | 1240 |
| Formula II-31 | >20000 | ND |
|  | >20000 |  |
| Formula II-32 | >20000 | ND |
|  | >20000 |  |
| Formula II-38 | 2600 | ND |
|  | 1800 |  |
| Formula IV-3C | >20000* | 7760 |
|  |  | 8290 |
| Formula II-44 | 12 | ND |
|  | 8.8 |  |
| Formula VI-1A | 8400 | ND |
|  | 7800 |  |
| Formula II-47 | 8000 ± 3400 | ND |
| Formula II-50 | 10 | ND |

Where n ≧ 3, mean EC$_{50}$ value ± standard deviation is presented;
*n = 3, standard deviation not applicable;
ND = not determined The EC$_{50}$ values indicate that Formulae II-2, II-4, II-5A, II-5B, II-18, II-19, II-20, II-22, II-24C, II-26, II-29 and II-30 were cytotoxic against RPMI 8226 and U266 cells. Formulae I-7, II-38, II-44, VI-1A, II-47, and II-50 were cytotoxic against RPMI 8226 cells. Formula II-21 and IV-3C were cytotoxic against U266 cells.

Example 37

Growth Inhibition of MES-SA, MES-SA/Dx5, HL-60 and HL-60/MX2 Tumor Cell Lines

Human uterine sarcoma (MES-SA; CRL-1976), its multidrug resistant derivative (MES-SA/Dx5; CRL-1977), human acute promyelocytic leukemia cells (HL-60; CCL-240) and its multidrug resistant derivative (HL-60/MX2; CRL-2257) were purchased from ATCC and maintained in appropriate culture media. The cells were cultured in an incubator at 37° C. in 5% CO$_2$ and 95% humidified air.

For cell growth inhibition assays, MES-SA and MES-SA/Dx5 cells were both seeded at 3×10$^3$ cells/well in 90 µl complete media into 96 well (Corning; 3904) black-walled, clear-bottom tissue culture plates and the plates were incubated overnight to allow cells to establish and enter log phase growth. HL-60 and HL-60/MX2 cells were both seeded at 5×10$^4$ cells/well in 90 µl complete media into 96 well plates on the day of compound addition. 20 mM stock solutions of the compounds were prepared in 100% DMSO and stored at −80° C. The compounds were serially diluted and added in triplicate to the test wells. Concentrations ranging from 6.32 µM to 2 nM were tested for II-2 and II-4. II-3 was tested at concentrations ranging from 20 µM to 6.32 nM. Compound II-18 was tested at concentrations ranging from 2 µM to 632 pM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in Mg$^{2+}$, Ca$^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and EC$_{50}$ values (the drug concentration at which 50% of the maximal observed growth inhibition is established) were determined using a standard sigmoidal dose response curve fitting algorithm (XLfit 3.0, ID Business Solutions Ltd). Where the maximum inhibition of cell growth was less than 50%, an EC$_{50}$ value was not determined.

The multidrug resistant MES-SA/Dx5 tumor cell line was derived from the human uterine sarcoma MES-SA tumor cell line and expresses elevated P-Glycoprotein (P-gp), an ATP dependent efflux pump. The data in Table 3 summarize the growth inhibitory effects of Formulae II-2, II-3, II-4 and II-18 against MES-SA and its multidrug resistant derivative MES-SA/Dx5. Paclitaxel, a known substrate of the P-gp pump was included as a control.

TABLE 3

EC$_{50}$ values of Formulae II-2, II-3, II-4 and II-18 against MES-SA and MES-SA/Dx5 tumor cell lines

| Compound | EC$_{50}$ (nM) MES-SA | EC$_{50}$ (nM) MES-SA/Dx5 | Fold change* |
|---|---|---|---|
| II-2 | 193 | 220 | 1.0 |
|  | 155 | 138 |  |
| II-3 | >20000 | >20000 | NA |
|  | >20000 | >20000 |  |
| II-4 | 163 | 178 | 0.9 |
|  | 140 | 93 |  |
| II-18 | 22 | 32 | 1.2 |
|  | 17 | 14 |  |
| Paclitaxel | 5.6 | 2930 | 798 |
|  | 4.6 | 5210 |  |

*Fold change = the ratio of EC$_{50}$ values (MES-SA/Dx5:MES-SA)

The EC$_{50}$ values indicate that II-2, II-4 and II-18 have cytotoxic activity against both MES-SA and MES-SA/Dx5 tumor cell lines. The multidrug resistant phenotype was confirmed by the observation that Paclitaxel was ~800 times less active against the resistant MES-SA/Dx5 cells.

HL-60/MX2 is a multidrug resistant tumor cell line derived from the human promyelocytic leukemia cell line, HL-60 and expresses reduced topoisomerase II activity. The data presented in Table 4 summarize the growth inhibitory effects of Formulae II-2, II-3, II-4 and II-18 against HL-60 and its multidrug resistant derivative HL-60/MX2. Mitoxantrone, the topoisomerase II targeting agent was included as a control.

TABLE 4

$EC_{50}$ values of Formulae II-2, II-3, II-4 and II-18 against HL-60 and HL-60/MX2 tumor cell lines

| Compound | $EC_{50}$ (nM) | | Fold change* |
|---|---|---|---|
| | HL-60 | HL-60/MX2 | |
| II-2 | 237 | 142 | 0.7 |
| | 176 | 133 | |
| II-3 | >20000 | >20000 | NA |
| | >20000 | >20000 | |
| II-4 | 143 | 103 | 0.8 |
| | 111 | 97 | |
| II-18 | 27 | 19 | 0.7 |
| | 23 | 18 | |
| Mitoxantrone | 42 | 1340 | 30.6 |
| | 40 | 1170 | |

*Fold change = the ratio of $EC_{50}$ values (HL-60/MX2:HL-60)

The $EC_{50}$ values indicate that II-2, II-4 and II-18 retained cytotoxic activity against both HL-60 and HL-60/MX2 tumor cell lines. The multidrug resistant phenotype was confirmed by the observation that Mitoxantrone was ~30 times less active against the resistant HL-60/MX2 cells.

The compounds disclosed herein have activity against drug resistant multiple myeloma cell lines. For example, the compounds are active against MM.1R and Doxorubicin-resistant Dox-40 cell lines. Furthermore, the compounds are active against cell lines obtained from human multiple myeloma patients that have relapsed after multiple prior therapies with Dexamethasone, Bortezomib, and thalidomide. Thus, the compounds are active against drug resistant multiple myeloma including multiple myeloma exhibiting resistance to doxorubicin, dexamethasone, bortezomib, and thalidomide.

Example 38

Inhibition of NF-κB-mediated Luciferase Activity by Formulae II-2, II-3, II-4, II-5A, II-5B, II8C, II-13C, II-18, II-19, II-20, II-21, II-22, II-24C, II-25, II-26, II-27, II-28, II-29, II-30, II-44, VI-1A and IV-3C; HEK293 NF-κB/Luciferase Reporter Cell Line The HEK293 NF-κB/luciferase reporter cell line is a derivative of the human embryonic kidney cell line (ATCC; CRL-1573) and carries a luciferase reporter gene under the regulation of 5×NF-κB binding sites. The reporter cell line was routinely maintained in complete DMEM medium (DMEM plus 10%(v/v) Fetal bovine serum, 2 mM L-glutamine, 10 mM HEPES and Penicillin/Streptomycin at 100 IU/ml and 100 µg/ml, respectively) supplemented with 250 µg/ml G418. When performing the luciferase assay, the DMEM basal medium was replaced with phenol-red free DMEM basal medium and the G418 was omitted. The cells were cultured in an incubator at 37° C. in 5% CO2 and 95% humidified air.

For NF-κB-mediated luciferase assays, HEK293 NF-κB/luciferase cells were seeded at $1.5\times10^4$ cells/well in 90 µl phenol-red free DMEM complete medium into Corning 3917 white opaque-bottom tissue culture plates. For Formula II-2, Formula II-4, Formula II-5A, and Formula II-18, a 400 µM starting dilution was made in 100% DMSO and this dilution was used to generate a 8-point half log dilution series. This dilution series was further diluted 40× in appropriate culture medium and ten µl aliquots were added to the test wells in triplicate resulting in final test concentrations ranging from 1 µM to 320 µM. For Formulae II-3, II-5B, II-8C, II-13C, II-20, II-21, II-22, II-24C, II-25, II-26, II-27, II-28, II-29, II-30, VI-1A and IV-3C, a 8 mM starting dilution was made in 100% DMSO and the same procedure was followed as described above resulting in final test concentrations ranging from 20 µM to 6.3 nM. For Formula I-19 and II-44, a 127 µM starting dilution was made in 100% DMSO and the final test concentrations ranged from 0.1 nM to 317 nM. For Formula II-20, a 2.5 mM or 8 mM starting solution was made in 100% DMSO and the final test concentrations ranged from 6.3 µM to 2.0 nM or 20 µM to 6.3 nM, respectively. The plates were returned to the incubator for 1 hour. After 1 hr pretreatment, 10 µl of a 50 ng/ml TNF-α solution, prepared in the phenol-red free DMEM medium was added, and the plates were incubated for an additional 6 hr. The final concentration of DMSO was 0.25% in all samples At the end of the TNF-α stimulation, 100 µl of Steady Lite HTS luciferase reagent (Packard Bioscience) was added to each well and the plates were left undisturbed for 10 min at room temperature before measuring the luciferase activity. The relative luciferase units (RLU) were measured by using a Fusion microplate fluorometer (Packard Bioscience). The $EC_{50}$ values (the drug concentration at which 50% of the maximal relative luciferase activity is inhibited) were calculated in Prism (GraphPad Software) using a sigmoidal dose response, variable slope model.

NF-κB regulates the expression of a large number of genes important in inflammation, apoptosis, tumorigenesis, and autoimmune diseases. In its inactive form, NF-κB complexes with IκB in the cytosol and upon stimulation, IκB is phosphorylated, ubiquitinated and subsequently degraded by the proteasome. The degradation of IκB leads to the activation of NF-κB and its translocation to the nucleus. The effects of Formulae II-2, II-3, II-4, II-5A, II-5B, II-8C, II-13C, II-18, II-19, II-20, II-21, II-22, II-24C, II-25, II-26, II-27, II-28, II-29, II-30, II-44, VI-1A and IV-3C on the activation of NF-κB were evaluated by assessing the NF-κB-mediated luciferase activity in HEK293 NF-κB/Luc cells upon TNF-α stimulation.

Pretreatment of NF-κB/Luc 293 cells with Formulae II-2, II-4, II-5A, II-5B, II-18, II-19, II-20, II-21, II-22, II-24C, II-26, II-29, II-30 and II-44 resulted in a dose-dependent decrease of luciferase activity upon TNF-α stimulation. The $EC_{50}$ values to inhibit NF-κB-mediated luciferase activity are shown in Table 5 and demonstrate that Compounds of Formulae II-2, II-4, II-5A, II-5B, II-18, II-19, II-20, II-21, II-22, II-24C, II-26, II-29, II-30 and II-44 inhibited NF-κB activity in this cell-based assay.

TABLE 5

EC$_{50}$ values of Formulae II-2, II-3, II-4, II-5A, II-5B, II-8C, II-13C,
II-18, II-19, II-20, II-21, II-22, II-24C, II-25, II-26, II-27, II-28, II-29,
II-30, II-44, VI-1A and IV-3C from NF-κB-mediated luciferase
reporter gene assay

| Compound | EC$_{50}$* |
|---|---|
| Formula II-2 | 71 ± 20 nM |
| Formula II-3 | >20 μM |
|  | >20 μM |
| Formula II-4 | 67 nM |
|  | 88 nM |
| Formula II-5A | 33 nM |
|  | 30 nM |
| Formula II-5B | 279 nM |
|  | 261 nM |
| Formula II-8C | >20 μM |
|  | >20 μM |
| Formula II-13C | >20 μM |
|  | >20 μM |
| Formula II-18 | 9 nM |
|  | 11 nM |
| Formula II-19 | 7 nM |
|  | 10 nM |
| Formula II-20 | 849 ± 225 nM** |
| Formula II-21 | 3.2 μM |
|  | 2.7 μM |
| Formula II-22 | 1 μM |
|  | 728 nM |
| Formula II-24C | 5.3 μM |
|  | 3.2 μM |
| Formula II-25 | >20 μM |
|  | >20 μM |
| Formula II-26 | 4.3 μM |
|  | 4.1 μM |
| Formula II-27 | >20 μM |
|  | >20 μM |
| Formula II-28 | >20 μM |
|  | >20 μM |
| Formula II-29 | 1.2 μM |
|  | 1.4 μM |
| Formula II-30 | 2.2 μM |
|  | 2.2 μM |
| Formula II-44 | 17 ± 4 nM |
| Formula VI-1A | >20 μM |
|  | >20 μM |
| Formula IV-3C | >20 μM |
|  | >20 μM |

*EC$_{50}$ values of two independent experiments are shown. Where n ≧ 3 the mean EC$_{50}$ value ± standard deviation is represented.
**The assay also was performed with compound II-20, and resulted in an EC$_{50}$ value of 154 nM, which value was not included in the calculation of the mean EC$_{50}$ value.

Example 39

In Vitro Inhibition of Proteasome Activity by Formulae I-7, II-2, II-3, II-4, II-5A, II-5B, II-8C, II-13C, II-18, II-19, II-20, II-21, II-22, II-24C, II-25, II-26, II-27, II-28, II-29, II-30, II-31, II-32, II-38, IV-3C, II-44, VI-1A and II-47

All the compounds were prepared as 20 mM stock solution in DMSO and stored in small aliquots at −80° C. Purified rabbit muscle 20S proteasome was obtained from CalBiochem or Boston Biochem. To enhance the chymotrypsin-like activity of the proteasome, the assay buffer (20 mM HEPES, pH7.3, 0.5 mM EDTA, and 0.05% Triton X100) was supplemented with SDS resulting in a final SDS concentration of 0.035%. The substrate used was suc-LLVY-AMC, a fluorogenic peptide substrate specifically cleaved by the chymotrypsin-like activity of the proteasome. Assays were performed at a proteasome concentration of 1 μg/ml in a final volume of 200 μl in 96-well Costar microtiter plates. Formulae II-2, II-4, II-18, II-19, II-21, II-22 and II-44 were tested as eight-point dose response curves with final concentrations ranging from 500 nM to 158 μM. Formulae I-7, II-5A, II-5B, II-20, II-29, II-30 and II-38 were tested at concentrations ranging from 1 μM to 0.32 nM. Formulae II-3 and VI-1A were tested as an eight-dose response curve with final concentrations ranging from 10 μM to 3.2 nM. Formula II-47 was tested at concentrations ranging from 5 μM to 1.6 nM, while Formulae II-8C, II-13C, II-24C, II-25, II-26, II-27, II-28, II-31, II-32 and IV-3C were tested with final concentrations ranging from 20 μM to 6.3 nM. The samples were incubated at 37° C. for five minutes in a temperature controlled Fluoroskan Ascent 96-well microplate reader (Thermo Electron, Waltham, Mass.). During the preincubation step, the substrate was diluted 25-fold in SDS-containing assay buffer. After the preincubation period, the reactions were initiated by the addition of 10 μl of the diluted substrate and the plates were returned to the plate reader. The final concentration of substrate in the reactions was 20 μM. Fluorescence of the cleaved peptide substrate was measured at $\lambda_{ex}$=390 nm and $\lambda_{em}$=460 nm. All data were collected every five minutes for more than 1.5 hour and plotted as the mean of triplicate data points. The EC$_{50}$ values (the drug concentration at which 50% of the maximal relative fluorescence is inhibited) were calculated by Prism (GraphPad Software) using a sigmoidal dose-response, variable slope model. To evaluate the activity of the compounds against the caspase-like activity of the 20S proteasomes, reactions were performed as described above except that Z-LLE-AMC was used as the peptide substrate. Formulae II-3, II-4, II-5A, II-5B, II-8C, II-13C, II-18, II-20, II-21, II-22, II-24C, II-25, II-26, II-27, II-28, II-29, II-30, IV-3C, II-44 and VI-1A were tested at concentrations ranging from 20 μM to 6.3 nM. Formula II-2 was tested at concentrations ranging from 10 μM to 3.2 nM, while Formula II-19 was tested at concentrations ranging from 5 μM to 1.58 nM. For the evaluation of the compounds against the trypsin-like activity of the proteasome, the SDS was omitted from the assay buffer and Boc-LRR-AMC was used as the peptide substrate. Formula II-20 was tested at concentrations ranging from 1.6 nM to 5 μM. Formulae II-3, II-8C, II-13C, II-21, II-22, II-24C, II-25, II-26, II-27, II-28, II-29, II-30, IV-3C and VI-1A were tested at concentrations ranging from 20 μM to 6.3 nM. For Formulae II-2 and II-5B the concentrations tested ranged from 10 μM to 3.2 nM, while Formulae II-4, II-5A, II-18 and II-19 were tested at concentrations ranging from 1 μM to 0.32 nM. Formula II-44 was tested at concentrations ranging from 2 μM to 632 μM.

Results (EC$_{50}$ values) are shown in Table 6 and illustrate that among the tested compounds, Formulae II-5A, II-18, II-19, II-20, II-21, II-22, II-29, II-38 and II-44 are the most potent inhibitors of the chymotrypsin-like activity of the 20S proteasome with EC$_{50}$ values ranging from 2 nM to 11 nM. Formulae II-7, II-2, II-4, I-5B, II-30 and II-47 inhibit the proteasomal chymotrypsin-like activity with EC$_{50}$ values ranging from 13 nM to 88 nM, while the EC$_{50}$ values of Formulae II-3, II-26 and VI-1A ranged from 207 nM to 964 nM. Formula II-13C, II-24C, II-27, II-28 and IV-3C inhibited the chymotrypsin-like activity with EC$_{50}$ values ranging from 1.4 μM to 10.6 μM. EC$_{50}$ values for Formulae II-8C, II-25, II-31 and II-32 were greater than 20 μM. Under the conditions tested, Formulae II-2, II-3, II-4, II-5A, II-5B, II-13C, II-18, II-19, II-20, II-21, II-22, II-24C, II-26, II-29, II-30, II-44 and VI-1A were able to inhibit the trypsin-like activity of the 20S proteasome. Formulae II-4, II-5A, II-18, II-19 and II-29 inhibited the caspase-like activity with EC$_{50}$ values ranging from 213 nM to 850 nM, while Formulae II-2, II-5B, II-20, II-21, II-22, II-30, II-44 and VI-1A had $EC_{50}$ values ranging from 956 nM to 8.7 μM.

TABLE 6

Effects of Formulae I-7, II-2, II-3, II-4, II-5A, II-5B, II-8C, II-13C, II-18, II-19, II-20, II-21, II-22, II-24C, II-25, II-26, II-27, II-28, II-29, II-30, II-31, II-32, II-38, IV-3C, II-44, VI-1A and II-47 on the various enzymatic activities of purified rabbit 20S proteasomes

| Analog | $EC_{50}$ Values* | | |
|---|---|---|---|
| | Chymotrypsin-like | Trypsin-like | Caspase-like |
| Formula I-7 | 52 ± 2 nM | ND | ND |
| Formula II-2 | 18 nM | 230 nM | 1.3 μM |
| | 19 nM | 230 nM | 1.7 μM |
| Formula II-3 | 964 nM | 5.5 μM | >20 μM |
| | 890 nM | 7.7 μM | >20 μM |
| Formula II-4 | 13 nM | 107 nM | 850 nM |
| | 15 nM | 110 nM | 637 nM |
| Formula II-5A | 6 nM | 87 nM | 535 nM |
| | 7 nM | 90 nM | 438 nM |
| Formula II-5B | 88 nM | 762 nM | 3.8 μM |
| | 85 nM | 716 nM | 2.9 μM |
| Formula II-8C | >20 μM | >20 μM | >20 μM |
| | >20 μM | >20 μM | >20 μM |
| Formula II-13C | 7.6 μM | 8.6 μM | >20 μM |
| | 8.8 μM | 12.8 μM | >20 μM |
| Formula II-18 | 2.3 nM | 14 nM | 286 nM |
| | 2 nM | 14 nM | 213 nM |
| Formula II-19 | 3 nM | 13 nM | 573 nM |
| | 3 nM | 15 nM | 739 nM |
| Formula II-20 | 7.7 ± 3.0 nM | 318 nM | 1.4 μM |
| | | 321 nM | 1.4 μM |
| Formula II-21 | 7 nM | 720 nM | 2.6 μM |
| | 8 nM | 879 nM | 2.3 μM |
| Formula II-22 | 7 nM | 308 nM | 1.3 μM |
| | 3 nM | 289 nM | 1.4 μM |
| Formula II-24C | 2.2 μM | 3.3 μM | >20 μM |
| | 2.0 μM | 3.1 μM | >20 μM |
| Formula II-25 | >20 μM | >20 μM | >20 μM |
| | >20 μM | >20 μM | >20 μM |
| Formula II-26 | 349 nM | 2.0 μM | >20 μM |
| | 319 nM | 3.0 μM | >20 μM |
| Formula II-27 | 1.4 μM | >20 μM | >20 μM |
| Formula II-28 | 3.2 μM | >20 μM | >20 μM |
| | 3.3 μM | >20 μM | >20 μM |
| Formula II-29 | 6 nM | 175 nM | 535 nM |
| | 8 nM | 254 nM | 520 nM |
| Formula II-30 | 21 nM | 905 nM | 956 nM |
| | 21 nM | 1.2 μM | 1.3 μM |
| Formula II-31 | >20 μM** | ND | ND |
| Formula II-32 | >20 μM** | ND | ND |
| Formula II-38 | 3.4 ± 0.2 nM | ND | ND |
| Formula IV-3C | 4.9 μM | >20 μM | >20 μM |
| | 10.6 μM | >20 μM | >20 μM |
| Formula II-44 | 11 nM | 55 nM | 1.4 μM |
| | 8.7 nM | 54 nM | 1.4 μM |
| Formula VI-1A | 274 nM | 3.1 μM | 7.9 μM |
| | 207 nM | 3.0 μM | 8.7 μM |
| Formula II-47 | 50 ± 10 nM | ND | ND |

*$EC_{50}$ values of one or two independent experiments are shown.
Where n ≥ 3 the mean $EC_{50}$ value ± standard deviation is presented,
**n = 3, standard deviation not applicable.
ND = not determined Example 40

The Effects of Formula II-16, Formula II-17, Formula II-20 and Omuralide on the Chymotrypsin-like Activity of 20S Proteasomes in RPMI 8226 Cells RPMI 8226 (ATCC, CCL-155), the human multiple myeloma cell line, was cultured in RPMI 1640 medium supplemented with 2 mM L-glutamine, 100 units/ml penicillin, 100 μg/ml streptomycin, 1 mM sodium pyruvate and 10% heat inactivated fetal bovine serum at 37° C., 5% $CO_2$ and 95% humidified air. To evaluate the inhibitory effects on the chymotrypsin-like activity of the 20S proteasome, test compounds prepared in DMSO were appropriately diluted in culture medium and added to $2.5 \times 10^5$/ml RMPI 8226 cells. For Formula II-16, the final test concentrations ranged from 1 nM to 100 nM. For Formula II-17, Formula II-20 and Omuralide (Calbiochem, San Diego, Calif.), the final test concentrations ranged from 1 nM to 10 μM. DMSO was used as the vehicle control at a final concentration of 0.1%. Following 1 hr incubation of RMPI 8226 cells with the compounds, the cells were pelleted by centrifugation at 2,000 rpm for 10 sec at room temperature and washed 3× with ice-cold 1× Dulbecco's Phosphate-Buffered Saline (DPBS, Mediatech, Herndon, Va.). DPBS washed cells were lysed on ice for 15 min in lysis buffer (20 mM HEPES, 0.5 mM EDTA, 0.05% Triton X-100, pH 7.3) supplemented with protease inhibitor cocktail (Roche Diagnostics, Indianapolis, Ind.). Cell debris was pelleted by centrifugation at 14,000 rpm for 10 min, 4° C. and supernatants (=cell lysates) were transferred to a new tube. Protein concentration was determined by the BCA protein assay kit (Pierce Biotechnology, Rockford, Ill.). The chymotrypsin-like activity of the 20S proteasome was measured by using the Suc-LLVY-AMC fluorogenic peptide substrate (Boston Biochem, Cambridge, Mass.) in the proteasome assay buffer (20 mM HEPES, 0.5 mM EDTA, pH 8.0) containing a final concentration of 0.035% SDS. The reactions were initiated by the addition of 10 μL of 0.4 mM Suc-LLVY-AMC (prepared by diluting a 10 mM solution of the peptide in DMSO 1:25 with assay buffer) to 190 μL of the cell lysates and incubated in the Thermo Lab Systems Fluoroskan plate reader at 37° C. The released coumarin (AMC) was measured fluorometrically by using $\lambda_{ex}$=390 nm and $\lambda_{em}$=460 nm. The assay was performed in a microtiter plate (Corning 3904) and followed kinetically with measurements every five minutes for 2 hr. The total amount of protein used for each assay was 20 μg. The final concentration of Suc-LLVY-AMC and DMSO was 20 μM and 0.2%, respectively. Results are presented as the percent inhibition of the 20S proteasome chymotrypsin-like activity relative to the DMSO control.

Results in Table 7 show that exposure of RPMI 8226 cells to Formula II-16, Formula II-17, Formula II-20 and Omuralide resulted in inhibition of the chymotrypsin-like activity of the 20S proteasomes. Among them, Formula II-16 inhibits 85±7% of the chymotrypsin-like activity of the 20S proteasome at 5 nM. At 100 nM, Formula II-16 is able to completely inhibit the chymotrypsin-like activity of the 20S proteasome. At 100 nM, Formula II-17, Formula II-20 and Omuralide are only able to inhibit the chymotrypsin-like activity at 30±4%, 66±3% and 32±8%, respectively.

TABLE 7

Determination of the chymotrypsin-like activity of 20S proteasomes derived from RMPI 8226 cells treated with Formula II-16, Formula II-17, Formula II-20 and Omuralide % inhibition of the chymotrypsin-like activity of 20S proteasomes in RPMI 8226 cell lysates (mean ± SD, n = 3)

| Compound | 10,000 nM | 1,000 nM | 500 nM | 100 nM | 50 nM | 10 nM | 5 nM | 1 nM |
|---|---|---|---|---|---|---|---|---|
| II-16 | ND | ND | ND | 98 ± 1 | 97 ± 0 | 94 ± 3 | 85 ± 7 | 30 ± 7 |
| II-17 | 65 ± 5 | 46 ± 4 | 39 ± 3 | 30 ± 4 | 26 ± 5 | 6 ± 6 | 10 ± 5 | 6 ± 6 |
| II-20 | 87 ± 4 | 73 ± 2 | 71 ± 2 | 66 ± 3 | 64 ± 3 | 37 ± 3 | 31 ± 9 | 3 ± 10 |
| Omuralide | 93 ± 1 | 80 ± 8 | 68 ± 11 | 32 ± 8 | 17 ± 11 | 4 ± 9 | 8 ± 9 | 5 ± 9 |

ND: not determined

Example 41

The Effects of Formula II-16, Formula II-17, Formula II-20 and Omuralide on the Chymotrypsin-like Activity of 20S Proteasomes in PC-3 Cells PC-3 (ATCC, CRL-1435), the human prostate cancer cell line, was cultured in F12K medium supplemented with 2 mM L-glutamine, 100 units/ml penicillin, 100 μg/ml streptomycin and 10% heat inactivated fetal bovine serum at 37° C., 5% $CO_2$ and 95% humidified air. To evaluate the inhibitory effects on the chymotrypsin-like activity of the 20S proteasome, test compounds prepared in DMSO were appropriately diluted in culture medium and added to $1.25 \times 10^5$/ml PC-3 cells. For Formula II-16, the final test concentrations ranged from 1 nM to 50 nM. For Formula II-17, Formula II-20 and Omuralide (Calbiochem, San Diego, Calif.), the final test concentrations ranged from 1 nM to 10 μM. DMSO was used as the vehicle control at a final concentration of 0.1%. Following 1 hr incubation of PC-3 cells with the compounds, the cells were washed 3× with ice-cold 1× Dulbecco's Phosphate-Buffered Saline (DPBS, Mediatech, Herndon, Va.). DPBS washed cells were lysed on ice for 15 min in lysis buffer (20 mM HEPES, 0.5 mM EDTA, 0.05% Triton X-100, pH 7.3) supplemented with protease inhibitor cocktail (Roche Diagnostics, Indianapolis, Ind.). Cell debris was pelleted by centrifugation at 14,000 rpm for 10 min, 4° C. and supernatants (=cell lysates) were transferred to a new tube. Protein concentration was determined by the BCA protein assay kit (Pierce Biotechnology, Rockford, Ill.). The chymotrypsin-like activity of the 20S proteasome was measured by using the Suc-LLVY-AMC fluorogenic peptide substrate (Boston Biochem, Cambridge, Mass.) in the proteasome assay buffer (20 mM HEPES, 0.5 mM EDTA, pH 8.0) containing a final concentration of 0.035% SDS. The reactions were initiated by the addition of 10 μL of 0.4 mM Suc-LLVY-AMC (prepared by diluting a 10 mM solution of the peptide in DMSO 1:25 with assay buffer) to 190 μL of the cell lysates and incubated in the Thermo Lab Systems Fluoroskan plate reader at 37° C. The released coumarin (AMC) was measured fluorometrically by using $\lambda_{ex}$=390 nm and $\lambda_{em}$=460 nm. The assay was performed in a microtiter plate (Corning 3904) and followed kinetically with measurements every five minutes for 2 hr. The total amount of protein used for each assay was 20 μg. The final concentration of Suc-LLVY-AMC and DMSO was 20 μM and 0.2%, respectively. Results are presented as the percent inhibition of the 20S proteasome chymotrypsin-like activity relative to the DMSO control.

Results in Table 8 show that exposure of PC-3 cells to Formula II-16, Formula II-17, Formula II-20 and Omuralide resulted in inhibition of the chymotrypsin-like activity of the 20S proteasomes similar to results obtained from RPMI 8226 cell-based experiments. Formula II-16 inhibits 69% of the chymotrypsin-like activity of the 20S proteasome at 5 nM. At 50 nM, Formula II-16 is able to completely inhibit the chymotrypsin-like activity of the 20S proteasome. At 100 nM, Formula II-17, Formula II-20 and Omuralide inhibit the chymotrypsin-like activity at 26%, 57% and 36%, respectively.

TABLE 8

Determination of the chymotrypsin-like activity of 20S proteasomes derived from PC-3 cells treated with Formula II-16, Formula II-17, Formula II-20 and Omuralide % inhibition of the chymotrypsin-like activity of 20S proteasomes in PC-3 cell lysates

| Compound | 10,000 nM | 1,000 nM | 100 nM | 50 nM | 10 nM | 5 nM | 1 nM |
|---|---|---|---|---|---|---|---|
| II-16 | ND | ND | ND | 98 | ND | 69 | 19 |
| II-17 | 79 | 49 | 26 | ND | 16 | ND | ND |
| II-20 | 90 | 71 | 57 | ND | 38 | ND | ND |
| Omuralide | 90 | 80 | 36 | ND | 18 | ND | ND |

ND: not determined

Example 42

Growth Inhibition of Human Multiple Myeloma, RPMI 8226, Human Colon Adenocarcinoma, HT-29 and Murine Melanoma, B16-F10 Cells in Media Containing 1% or 10% Serum The growth inhibitory activity of Formulae II-16 and Formula II-18 against human multiple myeloma, RPMI 8226, human colon adenocarcinoma, HT-29 and mouse melanoma, B16-F10 cells in the presence of 1% or 10% fetal bovine serum (FBS) was determined.

RPMI 8226 (CCL-155), HT-29 (HTB-38), and B16-F10 (CRL-6475) cells were purchased from ATCC. RPMI 8226 cells were maintained in RPMI 1640 media supplemented with 10% (v/v) FBS, 2 mM L-glutamine, 1 mM sodium pyruvate and Penicillin/Streptomycin at 100 IU/ml and 100 µg/ml, respectively. HT-29 cells were maintained in McCoys 5A supplemented with 10% (v/v) FBS, 2 mM L-glutamine, 1 mM sodium pyruvate, 1% (v/v) non-essential amino acids, 10 mM HEPES and Penicillin/Streptomycin at 100 IU/ml and 100 µg/ml, respectively. B16-F10 cells were maintained in DMEM supplemented with 10% (v/v) FBS, 2 mM L-glutamine, 10 mM HEPES and Penicillin/Streptomycin at 100 IU/ml and 100 µg/ml, respectively. The cells were cultured in an incubator at 37° C. in 5% $CO_2$ and 95% humidified air.

For cell growth inhibition assays, HT-29 and B16-F10 cells were seeded $5 \times 10^3$, and $1.25 \times 10^3$ cells/well respectively in 90 µl media containing 10% (v/v) FBS or 1% (v/v) FBS into 96 well (Corning; 3904) black-walled, clear-bottom tissue culture plates. The plates were incubated overnight to allow cells to establish and enter log phase growth. RPMI 8226 cells were seeded at $2 \times 10^4$ cells/well in 90 µl RPMI media containing 10% (v/v) FBS or 1% (v/v) FBS into 96 well black-walled, clear-bottom tissue culture plates. 20 mM stock solutions of Formulae II-16, II-17 and Formula II-18 were prepared in 100% DMSO, aliquoted and stored at −80° C. Formulae II-16, II-17 and Formula II-18 were serially diluted in media containing 1% or 10% FBS and added in triplicate to the test wells. The final concentration of Formula II-16 ranged from 2 µM to 20 µM. The final concentration range of Formula II-17 was from 20 µM to 6.3 nM. The final concentration of Formula II-18 ranged from 2 µM to 630 µM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and $EC_{50}$ values (the drug concentration at which 50% of the maximal observed growth inhibition is established) were determined using a standard sigmoidal dose response curve fitting algorithm (generated by XLfit 3.0, ID Business Solutions Ltd).

The data in Table 9 summarize the growth inhibitory effects of Formulae II-16, II-17 and Formula II-18 against the human multiple myeloma cell line, RPMI 8226 in media containing 1% or 10% FBS.

TABLE 9

$EC_{50}$ values of Formulae II-16, II-17 and Formula II-18 against RPMI 8226 cells in media containing 1% or 10% FBS

| Compound | 1% FBS, $EC_{50}$ (nM) | 10% FBS, $EC_{50}$ (nM) |
|---|---|---|
| II-16 | 6.2 | 12 |
|  | 6.8 | 9.6 |
| Mean | 6.5 | 11 |
| II-17 | 1100 | 3000 |
|  | 1300 | 2300 |
| Mean | 1200 | 2700 |
| II-18 | 15 | 20 |
|  | 13 | 20 |
| Mean | 14 | 20 |

The $EC_{50}$ values indicate that Formulae II-16, II-17 and Formula II-18 were cytotoxic against RPMI 8226 cells in media containing 1% or 10% FBS. There was a less than three fold decrease in the mean $EC_{50}$ of Formulae II-16, II-17 and Formula II-18 when tested in media containing 10% FBS relative to media containing 1% FBS.

The data in Table 10 summarize the growth inhibitory effects of Formula II-16 against the human colon adenocarcinoma, HT-29 and the murine melanoma, B16-F10 cell lines in media containing 1% or 10% FBS.

TABLE 10

Mean $EC_{50}$ values of Formula II-16 against HT-29 and B16-F10 cells in media containing 1% or 10% FBS

| Compound | HT-29, $EC_{50}$ (nM) mean ± SD | | B16-F10, $EC_{50}$ (nM) mean ± SD | |
|---|---|---|---|---|
|  | 1% FBS | 10% FBS | 1% FBS | 10% FBS |
| II-16 | 16 ± 5 | 23 ± 10 | 18 ± 9 | 13 ± 1 |

The mean $EC_{50}$ values indicate that Formula II-16 was cytotoxic against HT-29 and B16-F10 cells in media containing 1% or 10% FBS. There was a less than two fold decrease in the mean $EC_{50}$ of Formula II-16 when tested in media containing 10% FBS relative to media containing 1% FBS. Taken together, these data show that with respect to the in vitro cytotoxic activity against tumor cell lines, Formulae II-16, II-17 and Formula II-18 maintain similar biological activity in the presence of 1% or 10% FBS.

Example 43

Anthrax toxin is responsible for the symptoms associated with anthrax. In this disease, *B. anthracis* spores are inhaled and lodge in the lungs where they are ingested by macrophages. Within the macrophage, spores germinate, replicate, resulting in killing of the cell. Before killing occurs, however, infected macrophages migrate to the lymph nodes where, upon death, they release their contents, allowing the organism to enter the bloodstream, further replicate, and secrete lethal toxins.

Two proteins called protective antigen (PA; 83 kDa) and lethal factor (LF; 90 kDa), play a key role in the pathogenesis of anthrax. These proteins are collectively known as lethal toxin (LeTx). When combined, PA and LF cause death when injected intravenously in animals. Lethal toxin is also active in a few cell culture lines of macrophages causing cell death within a few hours. LeTx can induce both necrosis and apoptosis in mouse macrophage-like RAW264.7 cells upon in vitro treatment.

In Vitro Cell-Based Assay for Inhibitors of Lethal Toxin-Mediated Cytotoxicity

RAW264.7 cells (obtained from the American Type Culture Collection) were adapted to and maintained in RPMI-1640 medium supplemented with 10% fetal bovine serum, 2 mM L-glutamine and 1% Penicillin/Streptomycin (complete medium) at 37° C. in a humidified 5% $CO_2$ incubator. For the assay, cells were plated overnight in complete medium at a concentration of 50,000 cells/well in a 96-well plate. Media was removed the following day and replaced with serum-free complete medium with or without varying concentrations of Formulae II-2, II-3, II-4, II-5A, II-5B, II-13C, II-18 and IV-3C starting at 330 nM and diluting at ½ log intervals for an 8-point dose-response. After a 45 minute preincubation, 1 μg/ml LF and 1 μg/ml PA alone or in combination (LF:PA, also termed lethal toxin (LeTx)) were added to cells. Recombinant LF and PA were obtained from List Biological Laboratories. Additional plates with no LeTx added were included as a control. Cells were then incubated for six hours followed by addition of 0.02 mg/ml resazurin dye (Molecular Probes, Eugene, Oreg.) prepared in Mg++, Ca++ free PBS (Mediatech, Herndon, Va.). Plates were then incubated an additional 1.5 hours prior to the assessment of cell viability. Since resazurin is metabolized by living cells, cytotoxicity or cell viability can be assessed by measuring fluorescence using 530 excitation and 590 emission filters. Data are expressed as the percent viability as compared to a DMSO alone control (high) and the LeTx alone control (low) using the following equation: Percent viability=100*((Measured OD-low control)/(high control-low control)).

Inhibition of Anthrax Lethal Toxin-mediated Cytotoxicity in RAW 264.7 Cells

Data in FIG. 11 summarize the effects of Formula II-2, Formula II-3 and Formula II-4 against LeTx-mediated cytotoxicity of the RAW 264.7 murine macrophage-like cell line. Treatment of RAW 264.7 cells with Formula II-2 and Formula II-4 resulted in an increase in the viability of LeTx treated cells with $EC_{50}$ values of 14 nM (FIG. 11). The $EC_{50}$ values for Formula II-3 for LeTx protection was not be determined at the concentrations tested ($EC_{50}$>330 nM, the maximum concentration evaluated). Data in Table 11 show the effects of Formulae II-5A, II-5B, II-13C, II-18 and IV-3C against LeTx-mediated cytotoxicity of the RAW 264.7 murine macrophage-like cell line. Treatment of RAW 264.7 cells with Formula II-5A and II-18 showed an increase in the viability of LeTx treated RAW 264.7 cells with $EC_{50}$ values of 3 nM and 4 nM respectively. Treatment with Formula II-5B resulted in an increase in the viability of LeTx treated cells with an $EC_{50}$ value of 45 nM. The $EC_{50}$ values for Formulae U-13C and IV-3C for LeTx protection could not be determined at the concentrations tested ($EC_{50}$>330 nM, the maximum concentration evaluated).

TABLE 11

$EC_{50}$ values for inhibition of RAW 264.7 cell cytotoxicity mediated by anthrax lethal toxin

| Compound | $EC_{50}$ (nM) |
|---|---|
| Formula II-18 | 4 |
| Formula II-5A | 3 |
| Formula II-5B | 45 |
| Formula II-13C | >330nM |
| Formula IV-3C | >330nM |

Example 44

Structure-Activity Relationship of the $R_1$ Side Chain

A structure-activity relationship for the $R_1$ side chain of the disclosed compounds and specifically the compounds of Formulas (I), (II), (EH), (IV), and (V) was inferred by analyzing the relative activity of various compounds having the formula:

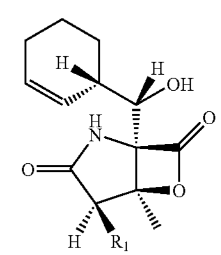

These compounds were assayed for cytotoxicity of RPMI cells and for inhibition of NF-κB and the chymotrypsin-, trypsin-, and caspase-like activities of the 20S proteasome. The results of 6 representative compounds are presented in Table 12.

TABLE 12

$EC_{50}$ values for compounds having varying $R_1$ groups

| Compound | $R_1$ | Cytotoxicity RPMI $EC_{50}$ (nM) | NF-κB $EC_{50}$ (nM) | Proteasome Chymotrypsin-like $EC_{50}$ (nM) | Proteasome Trypsin-like $EC_{50}$ (nM) | Proteasome Caspase-like $EC_{50}$ (nM) |
|---|---|---|---|---|---|---|
| II-16 | $CH_2CH_2Cl$ | 7 ± 0.4 | 11 ± 3 | 2.6 ± 0.2 | 21 ± 2.6 | 401 ± 93 |
| II-18 | $CH_2CH_2Br$ | 6.3, 6.3 | 11, 9 | 2.3, 2 | 14, 14 | 286, 213 |
| II-19 | $CH_2CH_2I$ | 6, 7 | 10, 7 | 3, 3 | 13, 15 | 573, 739 |
| II-17 | $CH_2CH_3$ | 6150, 3460 | 960 ± 210 | 26 ± 6.7 | 573, 602 | 1247, 1206 |
| II-20 | $CH_3$ | 8510 ± 3260 | 849 ± 225 | 7.7 ± 3.0 | 318, 321 | 1425, 1420 |
| II-21 | $CH_2CH_2OH$ | >20000, >20000 | 3172, 2707 | 7, 8 | 720, 879 | 2585, 2328 |

The results of the above assays can be interpreted to suggest that compounds having $R_1$ groups of chloroethyl, bromoethyl, or iodoethyl are potent inhibitors of proteasome and exhibit very potent cytotoxicity. In contrast, compounds having $R_1$ groups of methyl, ethyl, or hydroxyethyl exhibited relatively lower cytotoxicity (3-log decrease in potency), lower NF-κB inhibition (3-log decrease in potency), and a lower caspase-like (2 to 10 fold less potent) and trypsin-like (20 to 50 fold less potent) proteasome inhibition.

Without being bound to any particular theory, the Applicants note that the above results support the hypothesis that the increased activity of compounds containing Cl, Br, or I in the $R_1$ group can be due to the halogen's property of being a good leaving group. This hypothesis is supported by the fact that lactone ring opening of compound II-16 is observed to form a cyclic ether through nucleophilic substitution where chlorine is displaced according to the following reaction:

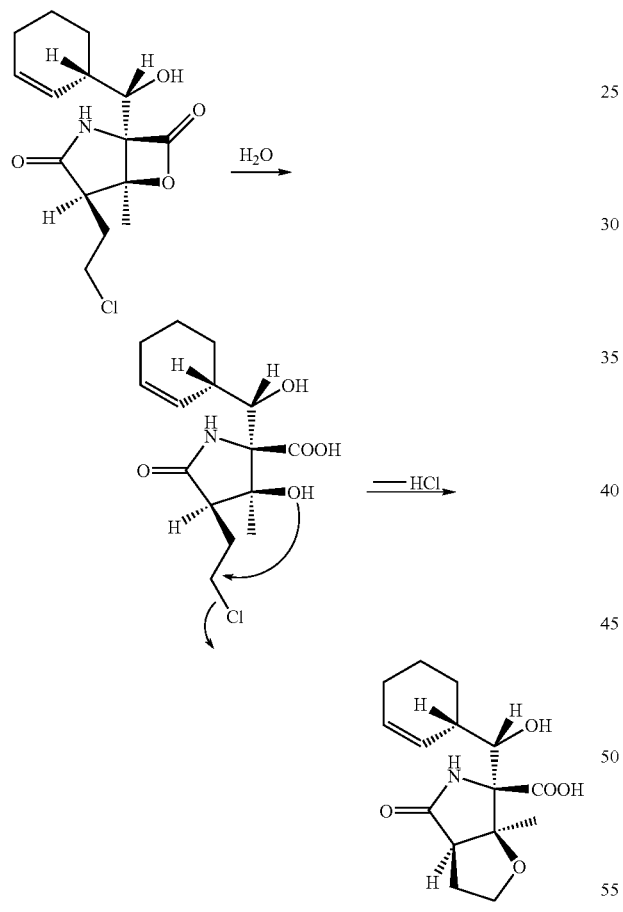

It is hypothesized that in compounds having a good leaving group in the $R_1$ side chain, such as compounds II-16, II-18, and II-19, nucleophilic addition of the proteasome to the β-lactone ring forms a cyclic ether in a manner similar to the above reaction. The cyclic ether, or formation thereof, is hypothesized to interact favorably with the proteasome.

Without being bound to any particular theory, the Applicants note that the above results also support the alternative hypothesis that a second nucleophile on the proteasome displaces the leaving group, thus forming a 2-point covalent adduct between the compound and the enzyme. In either case, leaving group functionality on the $R_1$ side chain promotes increased interaction between the compound and the enzyme and thus promotes increased activity. Therefore, compounds having other leaving groups on the $R_1$ side chain can be expected to exhibit high activity.

Without being bound to any particular theory, the Applicants note that the above results also support the hypothesis of a single-point leaving group. As one example, the presence of a halogen or other leaving group in the $R_1$ side chain promotes the delivery of the compound to its target, such as an intracellular or other biological target, thereby enhancing its therapeutic effect. An example of a single-point leaving group is illustrated in the diagram shown below.

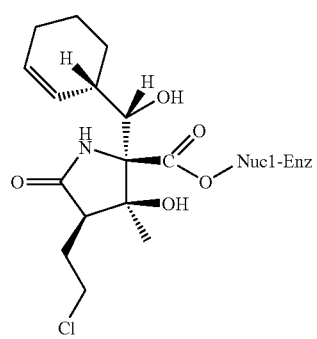

Single point covalent drug-enzyme adduct

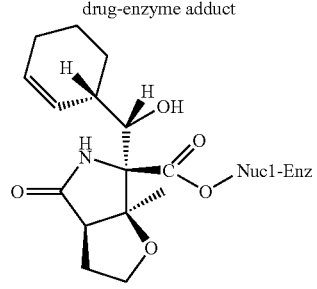

Single point covalent drug enzyme adduct with intramolecular Cl displacement

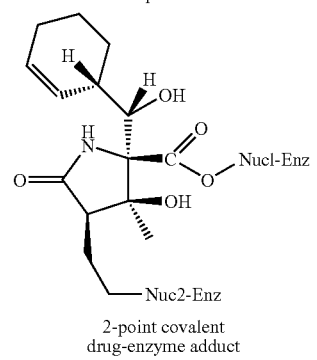

2-point covalent drug-enzyme adduct

"Leaving groups" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of a strong acid. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference in their entirety.

Example 45

Structure Activity Relationships

The data set forth in the above-listed Tables illustrate a number of preferred embodiments. With regard to Formula II, compounds having a halogenated substituent at $R_1$ are preferred and such compounds are generally equipotent across the above-described assays. Most preferred are n-halogenated ethyl at $R_1$.

Also, most preferred are compounds with a hydroxy group at $E_5$ and the attached carbon is in an S configuration (compounds having the stereochemistry of compound II-18, for example). Oxidation from a hydroxy group to a ketone is less preferred.

In one preferred embodiment, the preferred substituent at $R_4$ is cyclohexene. In another preferred embodiment, the cyclohexene is oxidized to an epoxide. Less preferred are compounds with hydrogenation of the double bond of the cyclohexene substituent.

Furthermore in some embodiments, preferably, $R_3$ is methyl, with ethyl being less preferred.

Example 46

Inhibition of Angiogenesis

Angiogenesis is an important physiological process, without which embryonic development and wound healing would not occur. However, excessive or inappropriate angiogenesis is associated with a number of diseases, conditions, and adverse treatment results. Examples of disease types and conditions associated with excessive angiogenesis include inflammatory disorders such as immune and non-immune inflammation, rheumatoid arthritis, chronic articular rheumatism and psoriasis; disorders associated with inappropriate or inopportune invasion of vessels such as diabetic retinopathy, neovascular glaucoma, retinopathy of prematurity, macular degeneration, corneal graft rejection, retrolental fibroplasia, rubeosis, capillary proliferation in atherosclerotic plaques and osteoporosis; and cancer associated disorders, including for example, solid tumors, tumor metastases, blood born tumors such as leukemias, angiofibromas, Kaposi sarcoma, benign tumors such as hemangiomas, acoustic neuromas, neurofibromas, trachomas, and pyogenic granulomas, as well as other cancers which require neovascularization to support tumor growth. Additional examples of angiogenesis-dependent diseases include, for example, Osler-Webber Syndrome; myocardial angiogenesis; plaque neovascularization; telangiectasia; hemophiliac joints and wound granulation. Furthermore, excessive angiogenesis is also associated with clinical problems as part of biological and mechanical implants (tissue/organ implants, stents, etc.). The instant compositions can be used to inhibit angiogenesis, and thus in the treatment of such conditions. Other diseases in which angiogenesis plays a role, and to which the instant compounds and compositions can be used, are known by those of skill in the art.

Particular discussion of angiogenesis in a number of pathophysiological conditions. such as cancer, rheumatoid arthritis, diabetic retinopathy, age related macular degeneration, endometriosis and obesity is found in Folkman J.(1985) Tumor angiogenesis. Adv Cancer Res. 1985;43:175-203.; Folkman, J. (2001). Angiogenesis-dependent diseases. *Semin Oncol*, 28, 536-42.; Grosios, K., Wood, J., Esser, R., Raychaudhuri, A. & Dawson, J. (2004). Angiogenesis inhibition by the novel VEGF receptor tyrosine kinase inhibitor, PTK787/ZK222584, causes significant anti-arthritic effects in models of rheumatoid arthritis. *Inflamm Res*, 53, 133-42; Hull, M. L., Charnock-Jones, D. S., Chan, C. L., Bruner-Tran, K. L., Osteen, K. G., Tom, B. D., Fan, T. P. & Smith, S. K. (2003). Antiangiogenic agents are effective inhibitors of endometriosis. *J Clin Endocrinol Metab*, 88, 2889-99; Liu, L. & Meydani, M. (2003). Angiogenesis inhibitors may regulate adiposity. *Nutr Rev*, 61, 384-7; Mousa, S. A. & Mousa, A. S. (2004). Angiogenesis inhibitors: current & future directions. *Curr Pharm Des*, 10, 1-9. Each of the above-described references is incorporated herein by reference in its entirety.

The compounds disclosed herein inhibit angiogenesis. The other compounds disclosed herein are tested in a transwell migration assay and inhibit migration. The compounds block vascular endothelial growth-factor (VEGF)-induced migration of multiple myeloma cells in a transwell migration assay.

The compounds disclosed herein show angiogenesis inhibitory activity in any of various other angiogenesis tests and assays, including one or more of the following.

The compounds disclosed herein show anti-angiogenic activity in various other in vitro and in vivo assays. Some examples include: in vitro assays for the evaluation of anti-angiogenesis compounds include,1) the modified Boyden chamber assay which assesses the migration of endothelial cells in response to pro-angiogenic factors (Alessandri G, Raju K, Gullino P M. (1983) "Mobilization of capillary endothelium in vitro induced by effectors of angiogenesis in vivo" Cancer Res. 43(4):1790-7.), 2) differentiation assays such as the Matrigel assay in which the attachment, migration and differentiation of endothelial cells into tubules is analyzed (Lawley T J, Kubota Y. (1989). Induction of morphologic differentiation of endothelial cells in culture. J Invest Dermatol.August;93(2 Suppl):59S-61S) and 3) organ culture assays in which the outgrowth of endothelial (and other cells) is monitored (Nicosia R F, Ottinetti A.(1990). Growth of microvessels in serum-free matrix culture of rat aorta. A quantitative assay of angiogenesis in vitro. Lab Invest. July;63(1):115-22.). Some in vivo assays for the evaluation of angiogenesis inhibitors are 1) sponge implantation assays, during which sponges containing cells and/or angiogenic factors and the test substance are implanted subcutaneously in animals for study of in vivo angiogenesis (Plunkett M L, Hailey J A. (1990). An in vivo quantitative angiogenesis model using tumor cells entrapped in alginate. Lab Invest. 1990 April;62(4):510-7), 2) the chick chorioallantoic membrane assay in which test compounds are inserted through a window, cut in the eggshell. The lack of a mature, immune system in the 7-8 day old chick embryo allows for the study of tumor-induced angiogenesis (Folkman J.(1985) Tumor angiogenesis. Adv Cancer Res. 1985; 43:175-203.) and 3) various tumor models in which specific histological analyses can be used to examine the effect on blood vessels, such as vascular density (CD31/CD34 staining), blood flow and concomitant tumor necrosis/apoptosis (TUNEL staining). In vitro assay examples include endothelial cell tests (HUVEC (human umbilical vein endothelial cell), aortic, capillary); endothelial cell proliferation assays; endothelial cell DNA synthesis assays; endothelial cell outgrowth assays (Aortic ring); endothelial cell migration assays (mentioned above; chemokinesis (colloidal gold), chemotaxis (Boyden chamber)); endothelial cell tube formation assays; endothelial apoptosis assays; endothelial cell viability assays (trypan blue); angiogenesis factor-transfected endothelial cell lines; and magnetized microbeads on endothelial cells. Each of the references in this paragraph is incorporated herein by reference in its entirety.

Examples of in vivo assays include transparent chamber tests (e.g., rabbit ear, hamster cheek, cranial window, and dorsal skin); matrix implants (e.g., subcutaneous injection using sodium alginate, subcutaneous disc (polyvinyl foam implant), rat dorsal air sac, sponge implant); cornea micropocket assays, for example in rabbits and other rodents; anterior eye/iris chamber implant assays, mice and knockout assays; ameroid constriction (heart) in pig and dog; rabbit hindlimb ischemia tests; vascularization into tissue (intradermal inoculation, peritoneal cavity/omentum with implant; tumor implants, for example in rabbits, mice or rats.

Also, ex vivo assays are performed using the disclosed compounds. Examples include CAM (chick chorioallantoic membrane assay) and vertical CAM with polymer gel. hmmunoassays such as serum assays, urine assays cerebrospinal fluid assays and tissue immunohistochemical assays.

Some of the above assays are described in the following papers, each of which is incorporated herein by reference in its entirety. Grant et al., In Vitro Cell Dev. Biol. 27A:327-336 (1991); Min et al., *Cancer Res*. 56:2428-2433 (1996); Schnaper et al., J. Cell. Physiol. 165:107-118 (1995); Schnaper et al., J. Cell. Physiol. 165:107-118 (1995); Oikawa et al., *Cancer Lett*. 59:57-66 (1991).

Embodiments relate to methods of using the compounds and compositions described herein, alone or in combination with other agents, to inhibit angiogenesis and to treat or alleviate diseases and conditions associated with excessive or inappropriate angiogenesis. Preferably, the inhibition occurs in connection with vascularization in connection with a disease associated with angiogenesis, such as cancer or any of the other diseases described above, and those that are known by those of skill in the art. The compounds and compositions can be delivered in an appropriate inhibitory amount. Inhibitory amount is intended to mean an amount of a compound or composition required to effect a decrease in the extent, amount or rate of neovascularization when administered to a tissue, animal or individual. The dosage of compound or composition required to be therapeutically effective will depend, for example, on the angiogenesis-dependent disease to be treated, the route and form of administration, the potency and big-active half-life of the molecule being administered, the weight and condition of the tissue, animal or individual, and previous or concurrent therapies. The appropriate amount application of the method can be determined by those skilled in the art, using the guidance provided herein. For example, the amount can be extrapolated from in vitro or in vivo angiogenesis assays described above. One skilled in the art will recognize that the condition of the patient needs to be monitored throughout the course of therapy and that the amount of the composition administered can be adjusted accordingly.

The present compounds and compositions can be and are used as well in conjunction with other angiogenesis inhibitors. Angiogenic inhibitors are known in the art and can be prepared by known methods. For example, angiogenic inhibitors include integrin inhibitory compounds such as .alpha.-V-beta-3 ($\alpha$V$\beta$3) integrin inhibitory antibodies, cell adhesion proteins or functional fragments thereof which contain a cell adhesion binding sequence. Additional angiogenic inhibitors include, for example, angiostatin, functional fragments of angiostatin, endostatin, fibroblast growth factor (FGF) inhibitors, FGF receptor inhibitors, VEGF inhibitors, VEGF receptor inhibitors, vascular permeability factor (VPF) inhibitors, VPF receptor inhibitors, thrombospondin, platelet factor 4, interferon-alpha, interferon-gamma, interferon-inducible protein 10, interleukin 12, gro-beta, and the 16 kDa N-terminal fragment of prolactin, thalidomide, and other mechanisms for the inhibition of angiogenesis.

Thus, the methods can include the step of administering a compound or composition to an animal suffering from a condition associated with excessive angiogenesis. The methods can further include administering the instant compound or composition along with another anti-angiogenesis drug or along with other therapies for the condition be treated (e.g., with a chemotherapeutic or immunotherapeutic to treat cancer).

The compounds or compositions can be delivered in any disease and/or patient appropriate manner. Examples include, intravenous, oral, intramuscular, intraocular, intranasal, intraperatoneal, and the like.

The following references provide additional teaching regarding methods of using, administering and assaying for angiogenesis inhibition: Angiogenesis Protocols (Methods in Molecular Medicine) by *J. Clifford Murray*, Humana Press (Mar. 15, 2001) ISBN: 0896036987; Tumour Angiogenesis, by *R. J. Bicknell, Claire E. Lewis, Napoleone Fe*, Oxford University Press (Sep. 1, 1997) ISBN: 0198549377; and Angiogenesis in Health and Disease: Basic Mechanisms and Clinical Applications, by *Gabor M. Rubanvi*, Marcel Dekker (Nov. 1, 1999) ISBN: 0824781023. Each book is incorporated herein by reference in its entirety. In particular the protocols and methods are incorporated herein.

Example 47

Formulation to be Administered Orally or the Like

A mixture obtained by thoroughly blending 1 g of a compound obtained and purified by the method of the embodiment, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

The examples described above are set forth solely to assist in the understanding of the embodiments. Thus, those skilled in the art will appreciate that the methods may provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications can be made to the embodiments disclosed herein without departing from the scope and spirit of the invention.

All patents and publications mentioned in the specification are indicative of the. levels of those skilled in the art to which the invention pertains. All patents and publications are herein incorporated by reference to the same extent as if each individual publication was specifically and individually indicated to be incorporated by reference.

The invention illustratively described herein suitably can be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed can be resorted to by those skilled in the art, and that such modifications and variations are considered to be falling within the scope of the embodiments of the invention.

What is claimed is:

1. A compound having the structure of Formula I, and pharmaceutically acceptable salts and pro-drug esters thereof:

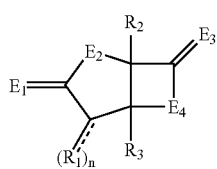

Formula I wherein the dashed line indicates that the designated bond is either a single bond or a double bond, and wherein $R_1$ is separately selected from the group consisting of a hydrogen, a halogen, a mono-substituted or poly-substituted saturated $C_1$-$C_{24}$ alkyl, mono-substituted, poly-substituted or unsubstituted variants of the following residues: unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, wherein the mono-substituted or poly-substituted saturated $C_1$-$C_{24}$ alkyl in $R_1$ is substituted with one or more substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyloxy, oxyacylamino, cyano, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

wherein the halogenated alkyl in $R_1$ is a $C_{1\text{-}24}$-alkyl poly-halogenated with fluorine, bromine, chlorine or iodine;

the halogenated alkyl is methyl or $C_{3\text{-}24}$-alkyl mono-or poly-halogenated with fluorine, bromine, chlorine, or iodine; or the halogenated alkyl is a ethyl mono-halogenated with fluorine, bromine, or iodine;

where n is equal to 1 or 2, and if n is equal to 2, then $R_1$ can be the same or different, and at least one $R_1$ is not hydrogen;

wherein $R_2$ is selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl;

wherein $R_3$ is selected from the group consisting of a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acid, boronic ester, and halogenated alkyl including polyhalogenated alkyl;

wherein each of $E_1$ and $E_3$ is a substituted or unsubstituted heteroatom selected from the group consisting of O and S, $E_2$ is a substituted or unsubstituted N, and $E_4$ is a substituted or unsubstituted heteroatom selected from the group consisting of O, S, and N; and with the proviso that Formula I is not Compound II-16 wherein Compound II-16 has the structure:

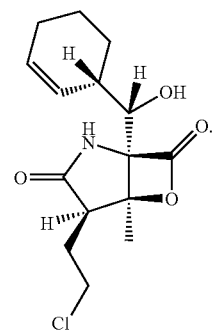

2. The compound of claim 1, wherein $R_2$ is a formyl.

3. A compound having the structure:

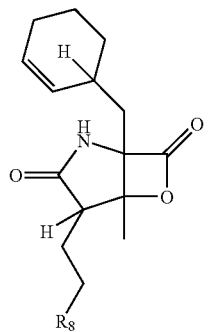

wherein $R_8$ is selected from the group consisting of H, F, Cl, Br, and I.

4. A compound having the structure of Formula II, and pharmaceutically acceptable salts and pro-drug esters thereof:

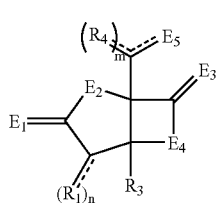

Formula II wherein the dashed lines indicates that the designated bond is either a single bond or a double bond, and wherein $R_1$ is separately selected from the group consisting of a hydrogen, a halogen, a mono-substituted or poly-substituted saturated $C_1$-$C_{24}$ alkyl, mono-substituted, poly-substituted or unsubstituted variants of the following residues: unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, wherein the mono-substituted or poly-substituted saturated $C_1$-$C_{24}$ alkyl in $R_1$ is substituted with one or more substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyloxy, oxyacylamino, cyano, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

wherein the halogenated alkyl in $R_1$ is a $C_{1-24}$-alkyl poly-halogenated with fluorine, bromine, chlorine or iodine;

the halogenated alkyl is methyl or $C_{3-24}$-alkyl mono-or poly-halogenated with fluorine, bromine, chlorine, or iodine; or the halogenated alkyl is a ethyl mono-halogenated with fluorine, bromine, or iodine;

where n is equal to 1 or 2, and if n is equal to 2, then $R_1$ can be the same or different, and at least one $R_1$ is not hydrogen;

wherein $R_3$ is selected from the group consisting of a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl;

wherein $R_4$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, and m is equal to 1 or 2, and if m is equal to 2, then $R_4$ can be the same or different;

wherein each of $E_1$ and $E_3$ is a substituted or unsubstituted heteroatom selected from the group consisting of O and S, $E_2$ is a substituted or unsubstituted N, and each $E_4$ and $E_5$ are a substituted or unsubstituted heteroatom selected from the group consisting of O, S, and N; and with the proviso that Formula II is not Compound II-16 wherein Compound II-16 has the structure:

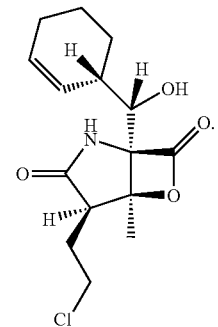

5. The compound of claim 4, wherein $E_5$ is selected from the group consisting of OH, O, S, N, NH, NH$_2$, NOH, NHOH, OR$_{10}$, SR$_{11}$, NR$_{12}$, and NHOR$_{13}$, wherein $R_{10}$, $R_{11}$, $R_{12}$, and $R_{13}$ each is separately selected from the group consisting of hydrogen, and a substituted or unsubstituted alkyl, acyl, aryl, and heteroaryl.

6. The compound of claim 4, wherein $R_3$ is methyl.

7. The compound of claim 4, wherein $E_5$ is OH.

8. The compound of claim 4, wherein each of $E_1$, $E_3$ and $E_4$ is O and $E_2$ is NH.

9. The compound of claim 4, wherein at least one $R_4$ is a cycloalkane.

10. A compound having the structure:

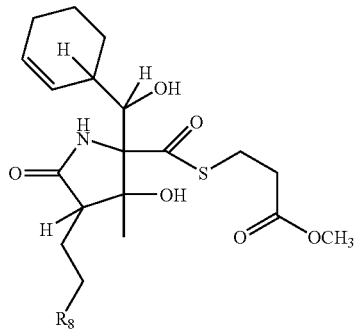

wherein $R_8$ is selected from the group consisting of H, F, Cl, Br and I.

11. A compound having the structure:

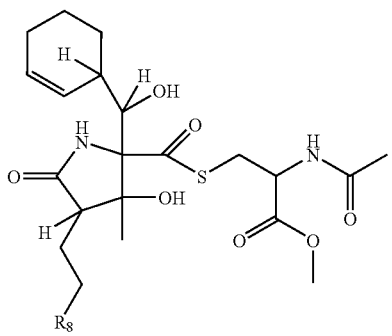

wherein $R_8$ is selected from the group consisting of H, F, Cl, Br and I.

12. The compound of claim 4, wherein at least one $R_4$ is a di-substituted cyclohexane.

13. The compound of claim 4, wherein at least one $R_4$ is a 7-oxa-bicyclo[4.1.0]hept-2-yl.

14. The compound of claim 4, wherein at least one $R_4$ is a substituted or an unsubstituted branched alkyl.

15. The compound of claim 4, wherein at least one $R_4$ is a cycloalkyl and $E_5$ is an oxygen.

16. The compound of claim 4, wherein $R_1$ is a substituted $C_1$ to $C_5$ alkyl.

17. The compound of claim 16, wherein the alkyl is selected from the group consisting of methyl, ethyl, propyl, isopropyl, butyl, isobutyl, tert-butyl, and pentyl.

18. A compound having the structure of Formula III, and pharmaceutically acceptable salts and pro-drug esters thereof:

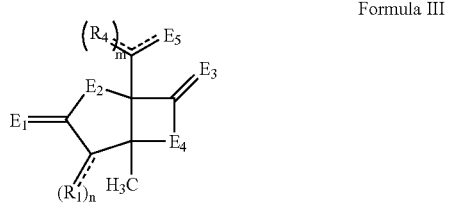

Formula III wherein the dashed lines indicates that the designated bond is either a single bond or a double bond, and wherein $R_1$ is separately selected from the group consisting of a hydrogen, a halogen, a mono-substituted or poly-substituted saturated $C_1$-$C_{24}$ alkyl, mono-substituted, poly-substituted or unsubstituted variants of the following residues: unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, wherein the mono-substituted or poly-substituted saturated $C_1$-$C_{24}$ alkyl in $R_1$ is substituted with one or more substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyloxy, oxyacylamino, cyano, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

wherein the halogenated alkyl in $R_1$ is a $C_{1-24}$-alkyl poly-halogenated with fluorine, bromine, chlorine or iodine;

the halogenated alkyl is methyl or $C_{3-24}$-alkyl mono-or poly-halogenated with fluorine, bromine, chlorine, or iodine; or the halogenated alkyl is a ethyl mono-halogenated with fluorine, bromine, or iodine;

where n is equal to 1 or 2, and if n is equal to 2, then $R_1$ can be the same or different, and at least one $R_1$ is not hydrogen;

wherein $R_4$ is separately selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, and m is equal to 1 or 2, and if m is equal to 2, then $R_4$ can be the same or different;

wherein each of $E_1$ and $E_3$ is a substituted or unsubstituted heteroatom selected from the group consisting of O and S, $E_2$ is a substituted or unsubstituted N, and each $E_4$ and $E_5$ are a substituted or unsubstituted heteroatom selected from the group consisting of O, S, and N; and with the proviso that Formula III is not Compound II-16, wherein Compound II-16 has the structure:

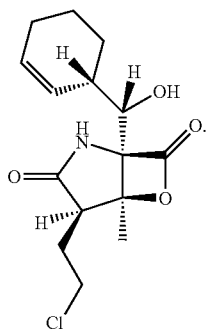

19. The compound of claim 18, wherein $R_1$ is a substituted $C_1$ to $C_5$ alkyl.

20. The compound of claim 19, wherein the alkyl is selected from the group consisting of methyl, ethyl, propyl, isopropyl, butyl, isobutyl, tert-butyl, and pentyl.

21. A compound having the structure of Formula IV, and pharmaceutically acceptable salts and pro-drug esters thereof:

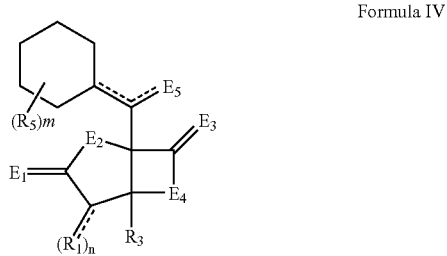

Formula IV wherein the dashed lines indicate that the designated bond is either a single bond or a double bond, and wherein $R_1$ is separately selected from the group consisting of a hydrogen, a halogen, a mono-substituted or poly-substituted saturated $C_1$-$C_{24}$ alkyl, mono-substituted, poly-substituted or unsubstituted variants of the following residues: unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, wherein the mono-substituted or poly-substituted saturated $C_1$-$C_{24}$ alkyl in $R_1$ is substituted with one or more substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyloxy, oxyacylamino, cyano, halogen, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

where n is equal to 1 or 2, and if n is equal to 2, then $R_1$ can be the same or different, and at least one $R_1$ is not hydrogen;

wherein $R_3$ is selected from the group consisting of a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl;

wherein $R_5$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, wherein m is 0, 1, 2, 3, 4, 5, 6, 7, 8, 9, 10, or 11 and if m is more than 1, then $R_5$ can be the same or different; and where the substituents $R_5$ can form a ring; and wherein each of $E_1$ and $E_3$ is a substituted or unsubstituted heteroatom selected from the group consisting of O and S, $E_2$ is substituted or unsubstituted N, and each $E_4$ and $E_5$ are a substituted or unsubstituted heteroatom selected from the group consisting of O, S, and N.

22. The compound of claim 18, wherein $R_1$ is a substituted $C_1$ to $C_5$ alkyl.

23. The compound of claim 22, wherein the alkyl is selected from the group consisting of methyl, ethyl, propyl, isopropyl, butyl, isobutyl, tert-butyl, and pentyl.

24. A compound having the structure of Formula V, and pharmaceutically acceptable salts and pro-drug esters thereof:

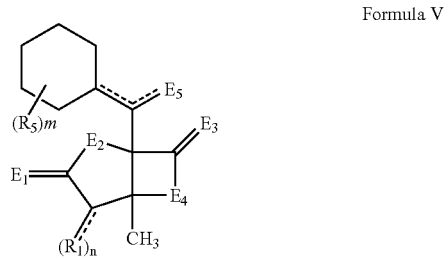

Formula V wherein the dashed line indicates that the designated bond is either a single bond or a double bond, and wherein $R_1$ is selected from the group consisting of a hydrogen, a halogen, a mono-substituted or poly-substituted saturated $C_1$-$C_{24}$ alkyl, mono-substituted, poly-substituted or unsubstituted variants of the following residues: unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, wherein the mono-substituted or poly-substituted saturated $C_1$-$C_{24}$ alkyl in $R_1$ is substituted with one or more substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyloxy, oxyacylamino, cyano, halogen, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl;

where n is equal to 1 or 2, and if n is equal to 2, then $R_1$ can be the same or different, and at least one $R_1$ is not hydrogen;

wherein $R_5$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, wherein m is 0, 1, 2, 3, 4, 5, 6, 7, 8, 9, 10, or 11, and if m is more than 1, then $R_5$ can be the same or different; and where the substituents $R_5$ can form a ring; and wherein each of $E_1$ and $E_3$ is a substituted or unsubstituted heteroatom selected from the group consisting of O and S, $E_2$ is a substituted or unsubstituted N, and each $E_4$ and $E_5$ are a substituted or unsubstituted heteroatom selected from the group consisting of O, S, and N.

25. The compound of claim 24, wherein $R_1$ is a substituted or an unsubstituted $C_1$ to $C_5$ alkyl.

26. The compound of claim 25, wherein the alkyl is selected from the group consisting of methyl, ethyl, propyl, isopropyl, butyl, isobutyl, tert-butyl, and pentyl.

27. A compound having the structure of Formula VI, and pharmaceutically acceptable salts and pro-drug esters thereof:

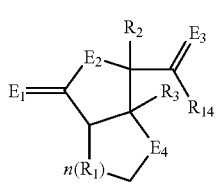

Formula VI wherein $R_1$ is separately selected from the group consisting of a mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, phenyl, cycloalkylacyl, hydroxy, alkylthio, arylthio, oxysulfonyl, carboxy, thio, sulfoxide, sulfone, sulfonate ester, thiocyano, boronic acid, boronic ester, and halogenated alkyl including polyhalogenated alkyl;

where n is equal to 1 or 2, and if n is equal to 2, then $R_1$ can be the same or different;

wherein $R_2$, is selected from the group consisting of hydrogen, a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate ester, thiocyano, boronic acid and boronic ester, and halogenated alkyl including polyhalogenated alkyl;

wherein $R_3$ is selected from the group consisting of a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate ester, thiocyano, boronic acid and boronic ester, and halogenated alkyl including polyhalogenated alkyl; wherein each of $E_1$ and $E_3$ can be a substituted or unsubstituted heteroatom selected from the group consisting of O and S, $E_2$ is a substituted or unsubstituted N, and $E_4$ is a substituted or unsubstituted heteroatom selected from the group consisting of O, S, and N; and wherein $R_{14}$ is selected from the group consisting of a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, thioesters, sulfoxide, sulfone, sulfonate esters, thiocyano, and halogenated alkyl including polyhalogenated alkyl.

28. The compound of claim 27, wherein the compound is:

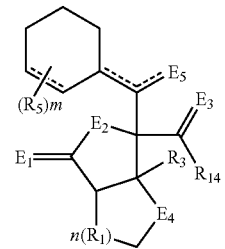

wherein $R_1$ can be separately selected from the group consisting of a mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, phenyl, cycloalkylacyl, alkylthio, arylthio, oxysulfonyl, carboxy, thio, sulfoxide, sulfone, sulfonate ester, thiocyano, boronic acid, boronic ester, and halogenated alkyl including polyhalogenated alkyl;

where n is equal to 1 or 2, and if n is equal to 2, then $R_1$ can be the same or different;

wherein $R_3$ can be selected from the group consisting of a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate ester, thiocyano, boronic acid boronic ester, and halogenated alkyl including polyhalogenated alkyl;

wherein $R_5$ can be separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, oxy, hydroxy, alkylthio, arylthio, oxysulfonyl, carboxy, cyano, thio, sulfoxide, sulfone, sulfonate ester, thiocyano, boronic acid boronic ester, and halogenated alkyl including polyhalogenated alkyl, wherein m is 0, 1, 2, 3, 4, 5, 6, 7, 8, 9, 10, or 11 and if m is more than 1, then $R_5$ can be the same or different; and where the substituents $R_5$ can form a ring; and wherein each of $E_1$ and $E_3$ is a substituted or unsubstituted heteroatom selected from the group consisting of O and S, $E_2$ is a substituted or unsubstituted N, and each $E_4$ and $E_5$ are a substituted or unsubstituted heteroatom selected from the group consisting of O, S, and N.

29. The compound of claim 27, wherein the compound is:

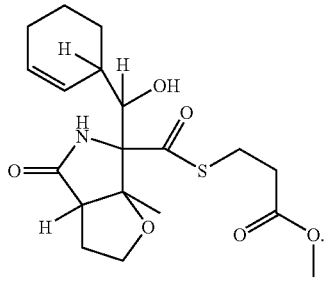

30. A pharmaceutical composition comprising at least one compound of claims 1, 4, 18, 19, 24 or 27.

31. The pharmaceutical composition of claim 30, further comprising an anti-microbial agent.

32. A compound having the structure of Formula I, and pharmaceutically acceptable salts and pro-drug esters thereof:

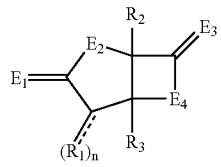

Formula I wherein the dashed line indicates that the designated bond is either a single bond or a double bond, and wherein $R_1$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl, $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, where n is equal to 1 or 2, and if n is equal to 2, then $R_1$ can be the same or different, and at least one $R_1$ is not hydrogen;

wherein $R_2$ is selected from the group consisting of a halogen, mono-substituted, poly-substituted or unsubstituted variants of the following residues: unsaturated $C_2$-$C_{24}$ alkenyl, $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl;

wherein $R_3$ is selected from the group consisting of a halogen, mono-substituted, poly-substituted or unsubstituted variants of the following residues: saturated $C_1$-$C_{24}$ alkyl, unsaturated $C_2$-$C_{24}$ alkenyl, $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl; and wherein each of $E_1$, and $E_3$ is a substituted or unsubstituted heteroatom selected from the group consisting of O and S, $E_2$ is a substituted or unsubstituted N, and $E_4$ is a substituted or unsubstituted heteroatom selected from the group consisting of O, S, and N.

33. The compound of claim 32, wherein $R_2$ is a formyl.

34. The compound of claim 33, wherein $E_2$ is a substituted N.

35. A compound having the structure of Formula II, and pharmaceutically acceptable salts and pro-drug esters thereof:

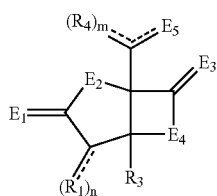

Formula II wherein the dashed lines indicates that the designated bond is either a single bond or a double bond, and wherein $R_1$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl, $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, where n is equal to 1 or 2, and if n is equal to 2, then $R_1$ can be the same or different, and at least one $R_1$ is not hydrogen;

wherein $R_3$ is selected from the group consisting of a halogen, mono-substituted, poly-substituted or unsubstituted variants of the following residues: saturated $C_1$-$C_{24}$ alkyl, unsaturated $C_2$-$C_{24}$ alkenyl, $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl;

wherein $R_4$ is separately selected from the group consisting of a hydrogen, a halogen, a mono-substituted or poly-substituted $C_1$-$C_{24}$ saturated alkyl, a mono-substituted, poly-substituted or unsubstituted variants of the following residues: unsaturated $C_2$-$C_{24}$ alkenyl, $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, and m is equal to 1 or 2, and if m is equal to 2, then $R_4$ can be the same or different;

wherein the mono-substituted or poly-substituted saturated $C_1$-$C_{24}$ alkyl in $R_4$ is substituted with one or more substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl;

wherein each of $E_1$ and $E_3$ is a substituted or unsubstituted heteroatom selected from the group consisting of O and S, $E_2$ is a substituted or unsubstituted N, and each $E_4$ and $E_5$ are a substituted or unsubstituted heteroatom selected from the group consisting of O, S, and N; and with the proviso that Formula II is not Compound II-16, wherein Compound II-16 has the structure:

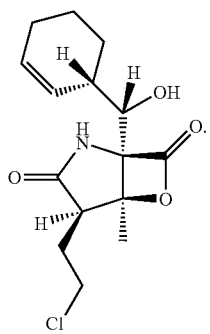

36. The compound of claim 35, wherein at least one $R_4$ is a cycloalkane.

37. The compound of claim 35, wherein at least one $R_4$ is a 7-oxa-bicyclo[4.1.0]hept-2-yl.

38. A compound having the structure of Formula III, and pharmaceutically acceptable salts and pro-drug esters thereof:

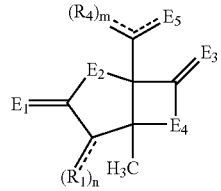

Formula III wherein the dashed lines indicates that the designated bond is either a single bond or a double bond, and wherein $R_1$ is separately selected from the group consisting of a hydrogen, a halogen, mono-substituted, poly-substituted or unsubstituted variants of the following residues: saturated $C_1$-$C_{24}$ alkyl, unsaturated $C_2$-$C_{24}$ alkenyl, $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, where n is equal to 1 or 2, and if n is equal to 2, then $R_1$ can be the same or different, and at least one $R_1$ is not hydrogen;

wherein $R_4$ is separately selected from the group consisting of hydrogen, a halogen, a mono-substituted or poly-substituted saturated $C_1$-$C_{24}$ alkyl, mono-substituted, poly-substituted or unsubstituted variants of the following residues: unsaturated $C_2$-$C_{24}$ alkenyl, $C_2$-$C_{24}$ alkynyl, acyl, acyloxy, alkyloxycarbonyloxy, aryloxycarbonyloxy, cycloalkyl, cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, hydroxy, alkylthio, arylthio, oxysulfonyl, carboxy, cyano, thio, sulfoxide, sulfone, sulfonate ester, thiocyano, boronic acid, boronic ester, and halogenated alkyl including polyhalogenated alkyl, and m is equal to 1 or 2, and if m is equal to 2, then $R_4$ can be the same or different;

wherein the mono-substituted or poly-substituted saturated $C_1$-$C_{24}$ alkyl in $R_4$ is substituted with one or more substituents selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl;

wherein each of $E_1$ and $E_3$ is a substituted or unsubstituted heteroatom selected from the group consisting of O and S, $E_2$ is a substituted or unsubstituted N, and each $E_4$ and $E_5$ are a substituted or unsubstituted heteroatom selected from the group consisting of O, S, and N; and with the proviso that Formula III is not Compound II-16, wherein Compound II-16 has the structure:

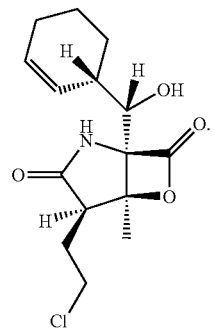

39. The compound of claim 1, wherein the halogenated alkyl is methyl or $C_{3-24}$-alkyl mono-or poly-halogenated with fluorine, bromine, chlorine, or iodine; and further substituted with an alkyl.

40. A compound having the structure:

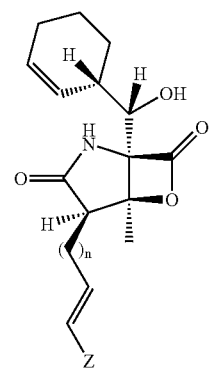

wherein n is an integer selected from the group consisting of 0, 1, 2, 3, 4, 5, and 6; and Z is an electron withdrawing group.

41. The compound of claim 40, wherein Z is selected from the group consisting of CHO, COR, COOR, $CONH_2$, CN, $NO_2$, SOR and $SO_2R$; and R is selected from the group consisting of H, substituted and unsubstituted alkyl, and substituted and unsubstituted aryl.

42. The compound of claim 41, wherein Z is selected from the group consisting of CHO, $COOCH_3$, $CONH_2$, CN, and $NO_2$.

43. The compound of claim 33, wherein the compound is:

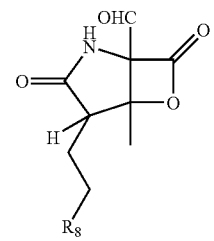

wherein $R_8$ is selected from the group consisting of H, F, Cl, Br, and I.

44. The compound of claim 35, wherein n is equal to 1 or 2, and where n is equal to 2, at least one $R_1$ is $CH_2CH_2X$, wherein X is selected from the group consisting of H, F, Cl, Br, and I.

45. The compound of claim 36, wherein n is equal to 2 and at least one of the $R_1$ substituents is hydrogen and the other $R_1$ substituent is $CH_2CH_2X$, wherein X is selected from the group consisting of H, F, Cl Br, and I; wherein at least one $R_4$ is cyclohexane; wherein $E_5$ is OH; wherein $R_3$ is methyl; and wherein each of $E_1$, $E_3$ and $E_4$ is O and $E_2$ is NH.

46. The compound of claim 45, wherein the structure is:

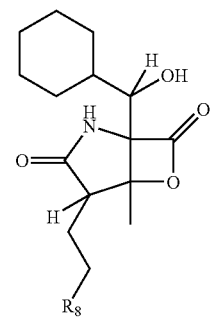

wherein $R_8$ is selected from the group consisting of H, F, Cl, Br and I.

47. The compound of claim 35, wherein the structure is:
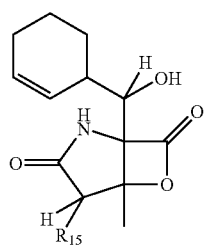
wherein $R_{15}$ is selected from the group consisting of hydroxyethyl, azidoethyl, and thiocyanoethyl.
48. The compound of claim 37, wherein the compound is:
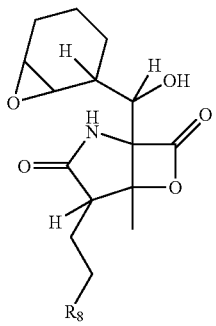
wherein $R_8$ is selected from the group consisting of H, F, Cl, Br, and I.
* * * * *